US010011590B2

(12) United States Patent
Iqbal et al.

(10) Patent No.: US 10,011,590 B2
(45) Date of Patent: Jul. 3, 2018

(54) CRYSTALLINE FORMS OF VILAZODONE HYDROCHLORIDE AND VILAZODONE FREE BASE

(71) Applicant: DR. REDDY'S LABORATORIES LIMITED, Hyderabad (IN)

(72) Inventors: Javed Iqbal, Hyderabad (IN); Srinivas Oruganti, Hyderabad (IN); Rajesh Kumar Rapolu, Hyderabad (IN); Vishweshwar Peddy, Hyderabad (IN); Rajesham Boge, Hyderabad (IN); Deepika Pathivada, Hyderabad (IN); Dharma Jagannadha Rao Velaga, Visakhapatnam (IN); Sesha Reddy Yarraguntla, Hyderabad (IN); Sudhakar Reddy Baddam, Hyderabad (IN); Anitha Naredla, Hyderabad (IN); Kiran Kumar Doniparthi, Nellore (IN); Srividya Ramakrishnan, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 15/487,090

(22) Filed: Apr. 13, 2017

(65) Prior Publication Data

US 2017/0217939 A1 Aug. 3, 2017

Related U.S. Application Data

(63) Continuation of application No. 14/400,144, filed as application No. PCT/IB2013/053785 on May 10, 2013, now abandoned.

(30) Foreign Application Priority Data

| | | |
|---|---|---|
| May 11, 2012 | (IN) | 1885/CHE/2012 |
| Jul. 23, 2012 | (IN) | 3013/CHE/2012 |
| Sep. 18, 2012 | (IN) | 3889/CHE/2012 |
| Nov. 6, 2012 | (IN) | 4655/CHE/2012 |
| Dec. 19, 2012 | (IN) | 5301/CHE/2012 |
| Dec. 19, 2012 | (IN) | 5319/CHE/2012 |

(51) Int. Cl.
*C07D 405/12* (2006.01)
*A61K 31/496* (2006.01)

(52) U.S. Cl.
CPC ........ *C07D 405/12* (2013.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 6,509,475 | B1 | 1/2003 | Bathe et al. | |
| 6,762,300 | B2 | 7/2004 | Bathe et al. | |
| 7,799,916 | B2 | 9/2010 | Bathe | |
| 7,834,020 | B2 | 11/2010 | Bathe et al. | |
| 2014/0057925 | A1 | 2/2014 | Dwived et al. | |
| 2014/0303185 | A1* | 10/2014 | Reguri | C07D 405/12 514/254.09 |
| 2014/0323498 | A1 | 10/2014 | Leksic et al. | |

FOREIGN PATENT DOCUMENTS

| | | |
|---|---|---|
| CN | 102249979 A | 11/2011 |
| CN | 102267985 A | 12/2011 |

OTHER PUBLICATIONS

Kakkar et el. Drug Development and Industrial Pharmacy, vol. 23(11), pp. 1063-1067 (1997).*
International Search Report dated Oct. 17, 2013, for corresponding International Patent Application No. PCT/IB2013/053785.
Written Opinion dated Oct. 17, 2013, for corresponding International Patent Application No. PCT/IB2013/053785.
International Preliminary Report on Patentability dated Nov. 11, 2014, for corresponding International Patent Application No. PCT/IB2013/053785.
Heinrich et al., "Synthesis and Structure-Activity Relationship in a Class of Indolebutylpiperazines as Dual 5-HT1A Receptor Agonists and Serotonin Reuptake Inhibitors", Journal of Medicinal Chemistry, 2004, pp. 4684 to 4692, vol. 47—issue No. 19, American Chemical Society.
Hu et al., "Scale-Up Synthesis of Antidepressant Drug Vilazodone", Organic Process Research and Development, 2012, pp. 1552 to 1557, vol. 16, American Chemical Society.
Non-Final Office Action dated Mar. 8, 2016, mailed by the USPTO, for corresponding U.S. Appl. No. 14/400,144.
Final Office Action dated Oct. 13, 2016, mailed by the USPTO, for corresponding U.S. Appl. No. 14/400,144.

* cited by examiner

*Primary Examiner* — Emily Bernhardt
(74) *Attorney, Agent, or Firm* — Pergament & Cepeda LLP; Milagros A. Cepeda; Edward D. Pergament

(57) ABSTRACT

The present application relates to crystalline and amorphous Vilazodone hydrochloride. The present application further relates to amorphous solid dispersions of vilazodone hydrochloride with pharmaceutically acceptable carriers. The present application also relates to a process for the preparation of form I of vilazodone free base.

5 Claims, 23 Drawing Sheets

CRYSTALLINE FORMS OF VILAZODONE HYDROCHLORIDE AND VILAZODONE FREE BASE

This application is a Continuation of U.S. patent application Ser. No. 14/400,144, filed Nov. 10, 2014, which is a National Stage Application under 35 U.S.C. § 371 of PCT International Application No. PCT/IB2013/053785, filed May 10, 2013, which claims the benefit of Indian Provisional Application Nos. 1885/CHE/2012, filed May 11, 2012, 3013/CHE/2012, filed Jul. 23, 2012, 3889/CHE/2012, filed Sep. 18, 2012, 4655/CHE/2012, filed Nov. 6, 2012, 5301/CHE/2012, filed Dec. 19, 2012, and 5319/CHE/2012, filed Dec. 19, 2012, all of which are hereby incorporated by reference in their entireties.

INTRODUCTION

One aspect of the present application relates to crystalline forms B, C, D, E, F, G and H of Vilazodone hydrochloride. Another aspect of the present application relates to amorphous vilazodone hydrochloride and a process for preparation thereof. Yet another aspect of the present application relates to amorphous solid dispersions of vilazodone hydrochloride. Still another aspect of the present application relates to a process for the preparation of vilazodone free base. Another aspect of the present application relates to crystalline form I of vilazodone free base.

Vilazodone hydrochloride is selective serotonin reuptake inhibitor, which also acts as partial agonist at serotonergic 5-$HT_{1A}$ receptors. It is mainly used for the treatment of major depressive disorder (MDD) and marketed as Viibryd™ in tablet dosage forms. The vilazodone hydrochloride is chemically known as 2-benzofurancarboxamide, 5-[4-[4-(5-cyano-1H-indol-3-yl)butyl]-1-piperazinyl]-, hydrochloride (1:1) and has structural formula I.

Formula I

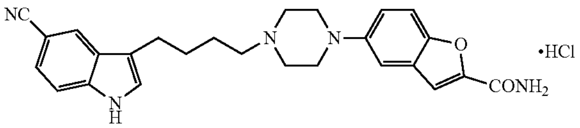

U.S. Pat. No. 7,834,020 covers vilazodone hydrochloride anhydrate form IV and its process of preparation thereof. The marketed form of vilazodone hydrochloride in USA is crystalline anhydrate form IV.

PCT publication No. WO2002102794 (hereinafter WO'794 application) discloses many other crystalline forms including hydrates and solvates of vilazodone hydrochloride. WO'794 discloses vilazodone hydrochloride solvates in its crystalline modification such as vilazodone hydrochloride monoacetonate as form I, vilazodone hydrochloride monosolvate with THF as form II and form XV, vilazodone hydrochloride hemisolvate with THF as form X, vilazodone hydrochloride monomethanolate as form XI, and vilazodone hydrochloride monosolvate with n-heptane as form XIV, furthermore vilazodone hydrochloride hydrate forms are disclosed as monohydrate form V, sesquihydrate form VI and hemihydrate form VIII.

WO'794 application also discloses three anhydrous crystalline forms of vilazodone hydrochloride namely form III, VII and IX.

All these crystalline forms are characterized by IR absorption spectra, X-ray powder diffraction pattern and differential scanning calorimetry.

PCT publication No. WO2012131706 (hereinafter WO'706 application) discloses amorphous vilazodone hydrochloride and process for its preparation.

U.S. Pat. No. 7,799,916 B2 (the US'916 patent) discloses a process for preparation of vilazodone hydrochloride by condensing 5-bromo-benzofuran-2-carboxamide with 3-(4-piperazin-1-ylbutyl)-indole-5-carbonitrile in presence of tris (dibenzylideneacetone)-dipalladium. The US'916 patent also discloses a process for preparation of vilazodone hydrochloride by condensation of 5-(piperazin-1-yl)benzofuran-2-carboxamide with 3-(4-oxobutyl)-1H-indole-5-carbonitrile in presence of sodium cyanoborohydride. The vilazodone free base thus obtained is converted to its hydrochloride salt by treating with aqueous 1N hydrochloric acid.

Heinrich et al. (J. Med. Chem., 2004, 47, 4684-92) discloses a process for preparation of vilazodone hydrochloride by condensing ethyl 5-(piperazin-1-yl)benzofuran-2-carboxylate hydrochloride with 3-(4-chlorobutyl)-1H-indole-5-carbonitrile in acetonitrile in presence of triethylamine and potassium carbonate. The product, ethyl 5-{4-[4-(5-cyano-3-indolyl)butyl]-1-piperazinyl}benzofuran-2-carboxylate is hydrolyzed in basic medium to afford the corresponding acid. The acid is reacted with ammonia in presence of 1-methyl-2-chloropyridinium iodide and ethyldiisopropylamine in N-methyl pyrrolidine to obtain vilazodone free base which is treated with HCl-saturated-2-propanol.

U.S. Pat. No. 6,509,475 B1 discloses a process for preparing 3-(4-chlorobutanoyl)-1H-indole-5-carbonitrile by treating 5-cyano indole with 4-chlorobuyryl chloride in presence of isobutylaluminium dichloride. It also discloses the preparation of 3-(4-chlorobutyl)-1H-indole-5-carbonitrile by reducing 3-(4-chlorobutanoyl)-1H-indole-5-carbonitrile by sodium borohydride in presence of isobutylaluminium dichloride.

CN Patent No. 102249979 A discloses a process for preparing 3-(4-chlorobutanoyl)-1H-indole-5-carbonitrile by treating 5-cyano indole with 4-chlorobutyryl chloride in presence of tin(IV)chloride.

Hu et al. (Organic Process Research & Development; Vol. 16; pp 1552-57; 2012) discloses a process for the preparation of 3-(4-chlorobutyl)-1-tosyl-1H-indole-5-carbonitrile which involves Friedel-Craft acylation of 1-tosyl-1H-indole-5-carbonitrile with 4-chlorobutyryl chloride and reducing the product, of 3-(4-chlorobutanoyl)-1-tosyl-1H-indole-5-carbonitrile, with sodium borohydride in presence of trifluoroacetic acid.

U.S. Pat. No. 6,762,300 B2 (the US '300 patent) teaches a process for the preparation of 5-(1-piperazinyl)benzofuran-2-carboxamide by a one pot reaction between 5-bromo-salicyaldehyde, ethyl bromoacetate and formamide to produce 5-bromobenzofuran-2-carboxylate; reacting the product of the earlier step with 1-benzyl piperazine in presence of transition metal catalyst to produce 5-(4-benzyl-1-piperazinyl)-benzofuran-2-carboxamide and deprotecting the benzyl group from the product.

The US'300 patent also teaches a process for the preparation of 5-(1-piperazinyl)benzofuran-2-carboxamide by reacting 1-benzyl piperazine with 5-bromo-salicyaldehyde in presence of a transition metal catalyst to produce 5-(4-benzyl-piperazin-1-yl)-2-hydroxybenzaldehyde; reacting the product of the earlier step with ethyl bromo-acetate to produce 5-(4-benzyl-piperazin-1-yl)-benzofuran-2-carboxamide and deprotecting the benzyl group from the product.

In general, polymorphism refers to the ability of a substance to exist as two or more crystalline phases that have different spatial arrangements and/or conformations of molecules in their crystal lattices. Thus, "polymorphs" refer to different crystalline forms of the same pure substance in which the molecules have different spatial arrangements of the molecules, atoms, and/or ions forming the crystal. Different polymorphs may have different physical properties such as melting points, solubilities, X-ray diffraction patterns, etc. The variation in solid forms may appreciably influence the pharmaceutical properties, such as bioavailability, handling properties, dissolution rate, and stability, and in turn such properties can significantly influence the processing, shelf life, and commercial acceptance of a polymorphic form. For these reasons, regulatory authorities require drug manufacturing companies to put efforts into identifying all polymorphic forms, e.g., crystalline, amorphous, solvates, stable dispersions with a pharmaceutically acceptable carriers, etc., of new drug substances.

The existence and possible numbers of polymorphic forms for a given compound cannot be predicted, and there are no "standard" procedures that can be used to prepare polymorphic forms of a substance. This is well-known in the art, as reported, for example, by A. Goho, "Tricky Business," *Science News*, Vol. 166(8), August 2004.

Hence, there remains a need for alternate polymorphic forms of vilazodone hydrochloride and processes for preparing them.

SUMMARY

The first aspect of the present application relates to crystalline forms B, C, D, E, F, G, H and amorphous solid dispersions of vilazodone hydrochloride; and processes for their preparation.

The second aspect of the present application relates to crystalline form B of vilazodone hydrochloride characterized by its powder X-ray diffraction (PXRD) pattern having peaks at about 7.10, 14.96, 17.31 and 21.64±0.2 degrees 2θ. In embodiments, the present application relates to crystalline form B of vilazodone hydrochloride characterized by its PXRD pattern having additional peaks located at about 19.63, 22.40, 22.99, 25.91 and 26.72±0.2 degrees 2θ. Still in other embodiments, the present application relates to crystalline form B of vilazodone hydrochloride characterized by its PXRD pattern having additional peaks located at about 12.10 and 12.66±0.2 degrees 2θ.

The third aspect of the present application relates to crystalline form B of vilazodone hydrochloride that can be characterized by a PXRD pattern having peaks located substantially as illustrated in the pattern of FIG. 1 or FIG. 2 or FIG. 3 or FIG. 4 or FIG. 5.

The fourth aspect of the present application relates to crystalline form B of vilazodone hydrochloride that can be characterized by a DSC thermogram substantially as illustrated in the pattern of FIG. 17.

The fifth aspect the present application relates to crystalline form B of vilazodone hydrochloride that can be characterized by a TGA thermogram substantially as illustrated in the pattern of FIG. 18.

The sixth aspect of the present application relates to crystalline form B of vilazodone hydrochloride that can be characterized by an IR spectrum substantially as illustrated in the pattern of FIG. 19.

The seventh aspect of the present application relates to crystalline form B of vilazodone hydrochloride that can be characterized by a scanning electron microscopic pattern substantially as illustrated in FIG. 23.

The eighth aspect of the present application relates to a process for preparing crystalline form B of vilazodone hydrochloride, which comprises:

a) providing a mixture of vilazodone free base in suitable solvent or mixtures thereof;
b) combining hydrochloric acid with the mixture of step a); and
c) isolating crystalline form B of vilazodone hydrochloride.

The ninth aspect of the present application relates to a process for packaging and storing of crystalline form B of vilazodone hydrochloride comprises the following steps:

a) placing crystalline form B of vilazodone hydrochloride in a clear polyethylene bag tied with a thread,
b) placing the primary packing containing crystalline form B of vilazodone hydrochloride inside a black colour polyethylene bag containing silica gel and sealing it,
c) placing the above double polyethylene bag inside a triple laminated bag containing silica gel and
d) placing the sealed triple laminated bag inside a closed high density polyethylene (HDPE) container and storing at room temperature.

The tenth aspect of the present application relates to a pharmaceutically acceptable dosage form comprising crystalline form B of vilazodone hydrochloride and one or more pharmaceutically acceptable excipients.

The eleventh aspect of the present application relates to crystalline form C of vilazodone hydrochloride characterized by its powder X-ray diffraction (PXRD) pattern having peaks at about 10.50, 14.20 and 20.20±0.2 degrees 2θ. In embodiments, the present application relates to crystalline form C of vilazodone hydrochloride characterized by its PXRD pattern having an additional peak located at about 9.06±0.2 degrees 2θ.

The twelfth aspect of the present application relates to crystalline form C of vilazodone hydrochloride that can be characterized by a PXRD pattern having peaks located substantially as illustrated in the pattern of FIG. 6 or FIG. 7 or FIG. 8.

The thirteenth aspect of the present application relates to process for preparing crystalline form C of vilazodone hydrochloride by drying the crystalline form B of vilazodone hydrochloride with a suitable drying technique.

The fourteenth aspect of the present application relates to a pharmaceutically acceptable dosage form comprising crystalline form C of vilazodone hydrochloride and one or more pharmaceutically acceptable excipients.

The fifteenth aspect of the present application relates to solvates of vilazodone hydrochloride with solvents selected from the group consisting of halogenated hydrocarbons, aliphatic esters, aliphatic amides, dimethyl sulfoxide, N-methyl-2-pyrrolidone and mixtures thereof.

The sixteenth aspect of the present application relates to crystalline vilazodone hydrochloride form D characterized by its powder X-ray diffraction (PXRD) pattern having at about 13.39, 13.67, 16.00, 21.22 and 24.61±0.2 degrees 2θ. In embodiments, the present application relates to crystalline vilazodone hydrochloride form D characterized by its PXRD pattern having one or more additional peaks located at about 5.53, 9.60, 10.54 and 11.09±0.2 degrees 2θ.

The seventeenth aspect of the present application relates to crystalline vilazodone hydrochloride form D that can be characterized by a PXRD pattern having peaks located substantially as illustrated in the pattern of FIG. 9.

The eighteenth aspect of the present application relates to process for preparing crystalline vilazodone hydrochloride form D, which comprises:

a) providing a solution of vilazodone hydrochloride in dimethyl sulfoxide solvent;

b) combining ethyl acetate with the solution of step a); and c) isolating crystalline vilazodone hydrochloride form D.

The nineteenth aspect of the present application relates to a pharmaceutically acceptable dosage form comprising crystalline form D of vilazodone hydrochloride and one or more pharmaceutically acceptable excipients.

The twentieth aspect of the present application relates to crystalline vilazodone hydrochloride form E characterized by its powder X-ray diffraction (PXRD) pattern having peaks at about 10.62, 16.18 and 21.42±0.2 degrees 2θ. In embodiments, the present application relates to crystalline vilazodone hydrochloride form E characterized by its PXRD pattern having one or more additional peaks located at about 5.55, 9.54 and 11.06±0.2 degrees 2θ.

The twenty first aspect of the present application relates to crystalline vilazodone hydrochloride form E that can be characterized by a PXRD pattern having peaks located substantially as illustrated in the pattern of FIG. 10.

The twenty second aspect of the present application relates to process for preparing crystalline vilazodone hydrochloride form E, which comprises:

a) providing a solution of vilazodone hydrochloride in N-methyl-2-pyrrolidone solvent;

b) combining dichloromethane with the solution of step a); and c) isolating crystalline vilazodone hydrochloride form E.

The twenty third aspect of the present application relates to a pharmaceutically acceptable dosage form comprising crystalline form E of vilazodone hydrochloride and one or more pharmaceutically acceptable excipients.

The twenty fourth aspect of the present application relates to crystalline vilazodone hydrochloride form F characterized by its powder X-ray diffraction (PXRD) pattern having peaks at about 13.45, 13.73, 21.24 and 24.85±0.2 degrees 2θ. In embodiments, the present application relates to crystalline vilazodone hydrochloride form F characterized by its PXRD pattern having one or more additional peaks located at about 10.65, 11.07 and 16.07±0.2 degrees 2θ. Still in other embodiments, the present application relates to crystalline vilazodone hydrochloride form F characterized by its PXRD pattern having one or more additional peaks located at about 5.55, 9.61 and 15.31±0.2 degrees 2θ.

The twenty fifth aspect of the present application relates to crystalline vilazodone hydrochloride form F that can be characterized by a PXRD pattern having peaks located substantially as illustrated in the pattern of FIG. 11.

The twenty sixth aspect of the present application relates to process for preparing crystalline vilazodone hydrochloride form F, which comprises:

a) providing a solution of vilazodone hydrochloride in N,N-dimethylformamide solvent;

b) combining ethyl acetate with the solution of step a); and c) isolating crystalline vilazodone hydrochloride form F.

The twenty seventh aspect of the present application relates to a pharmaceutically acceptable dosage form comprising crystalline form F of vilazodone hydrochloride and one or more pharmaceutically acceptable excipients.

The twenty eighth aspect of the present application relates to crystalline form G of vilazodone hydrochloride characterized by its powder X-ray diffraction (PXRD) pattern having peaks at about 10.71, 16.59, 20.58 and 22.27 and ±0.2 degrees 2θ. In embodiments, the present application relates to crystalline form G of vilazodone hydrochloride characterized by its PXRD pattern having additional peaks located at about 8.61, 21.33, 24.30 and 25.01±0.2 degrees 2θ. Still in other embodiments, the present application relates to crystalline form G of vilazodone hydrochloride characterized by its PXRD pattern having additional peaks located at about 15.41 and 19.40±0.2 degrees 2θ.

The twenty ninth aspect of the present application relates to crystalline form G of vilazodone hydrochloride that can be characterized by a PXRD pattern having peaks located substantially as illustrated in the pattern of FIG. 13.

The thirtieth aspect of the present application relates to a process for preparing crystalline form G of vilazodone hydrochloride, which comprises:

a) providing a mixture of vilazodone free base in suitable solvent or mixtures thereof;

b) combining hydrochloric acid with the mixture of step a); and c) isolating crystalline form G of vilazodone hydrochloride.

The thirty first aspect of the present application relates to a pharmaceutically acceptable dosage form comprising crystalline form G of vilazodone hydrochloride and one or more pharmaceutically acceptable excipients.

The thirty second aspect of the present application relates to conversion of crystalline form G of vilazodone hydrochloride to crystalline form B of vilazodone hydrochloride by suitable technique.

The thirty third aspect of the present application relates to crystalline form H of vilazodone hydrochloride characterized by its powder X-ray diffraction (PXRD) pattern having peaks at about 19.72, 20.92, 25.25 and 26.26±0.2 degrees 2θ. In embodiments, the present application relates to crystalline form H of vilazodone hydrochloride characterized by its PXRD pattern having additional peaks located at about 8.45, 12.46, 18.54 and 19.18±0.2 degrees 2θ. Still in other embodiments, the present application relates to crystalline form H of vilazodone hydrochloride characterized by its PXRD pattern having additional peaks located at about 13.08 and 16.25±0.2 degrees 2θ.

The thirty fourth aspect of the present application relates to crystalline form H of vilazodone hydrochloride that can be characterized by a PXRD pattern having peaks located substantially as illustrated in the pattern of FIG. 14.

The thirty fifth aspect of the present application relates to crystalline form H of vilazodone hydrochloride that can be characterized by a DSC thermogram substantially as illustrated in the pattern of FIG. 15.

The thirty sixth aspect of the present application relates to crystalline form H of vilazodone hydrochloride that can be characterized by a TGA thermogram substantially as illustrated in the pattern of FIG. 16.

The thirty seventh aspect of the present application relates to a process for preparing crystalline form H of vilazodone hydrochloride, which comprises:

a) providing a mixture of vilazodone free base in suitable solvent or mixtures thereof;

b) combining hydrochloric acid with the mixture of step a);

c) isolating crystalline vilazodone hydrochloride; and d) stirring crystalline vilazodone hydrochloride as obtained in step c) in water; and e) isolating crystalline form H of vilazodone hydrochloride.

The thirty eighth aspect of the present application relates to a pharmaceutically acceptable dosage form comprising crystalline form H of vilazodone hydrochloride and one or more pharmaceutically acceptable excipients.

The thirty ninth aspect of the present application relates to amorphous solid dispersion of vilazodone hydrochloride with a pharmaceutically acceptable carrier.

The fortieth aspect of the present application relates to amorphous solid dispersion of vilazodone hydrochloride with a pharmaceutically acceptable carrier such as polyvinylpyrrolidone (PVP) or hydroxypropyl methylcellulose (HPMC) that can be characterized by a PXRD pattern substantially as illustrated in the pattern of FIG. 12.

The forty first aspect of the present application relates to process for preparing amorphous solid dispersion of vilazodone hydrochloride with a pharmaceutically acceptable carrier, which comprises:

a) providing a mixture of vilazodone hydrochloride and pharmaceutically acceptable carrier in suitable solvent or mixtures thereof;
b) heating the mixture to obtain a clear solution; and
c) isolating amorphous solid dispersion of vilazodone hydrochloride with a pharmaceutically acceptable carrier.

The forty second aspect of the present application relates to a pharmaceutically acceptable dosage form comprising amorphous solid dispersion of vilazodone hydrochloride and one or more pharmaceutically acceptable excipients.

The forty third aspect of the present application relates to amorphous solid dispersion of vilazodone hydrochloride with a polyvinylpyrrolidone (PVP).

The forty fourth aspect of the present application relates to process for preparing amorphous solid dispersion of vilazodone hydrochloride with polyvinylpyrrolidone (PVP), which comprises:

a) providing a mixture of vilazodone hydrochloride and polyvinylpyrrolidone (PVP) in suitable solvent or mixtures thereof;
b) heating the mixture to obtain a clear solution; and
c) isolating amorphous solid dispersion of vilazodone hydrochloride with polyvinylpyrrolidone (PVP).

The forty fifth aspect of the present application relates to a pharmaceutically acceptable dosage form comprising amorphous solid dispersion of vilazodone hydrochloride with PVP and one or more pharmaceutically acceptable excipients.

The forty sixth aspect of the present application relates to amorphous solid dispersion of vilazodone hydrochloride with hydroxypropyl methylcellulose (HPMC).

The forty seventh aspect of the present application relates to process for preparing amorphous solid dispersion of vilazodone hydrochloride with hydroxypropyl methylcellulose (HPMC), which comprises:

a) providing a mixture of vilazodone hydrochloride and hydroxypropyl methylcellulose (HPMC) in suitable solvent or mixtures thereof;
b) heating the mixture to obtain a clear solution; and
c) isolating amorphous solid dispersion of vilazodone hydrochloride with hydroxypropyl methylcellulose (HPMC).

The forty eighth aspect of the present application relates to a pharmaceutically acceptable dosage form comprising amorphous solid dispersion of vilazodone hydrochloride with HPMC and one or more pharmaceutically acceptable excipients.

The forty ninth aspect of the present application relates to pure amorphous form of vilazodone hydrochloride.

The fiftieth aspect of the present application relates to pure amorphous form of vilazodone hydrochloride which may be characterized by a PXRD pattern substantially as illustrated in FIG. 20.

The fifty first aspect of the present application relates to a process for preparing pure amorphous form of vilazodone hydrochloride comprising:

a) subjecting known crystalline form of vilazodone hydrochloride to ball milling; and
b) isolating pure amorphous form of vilazodone hydrochloride.

The fifty second aspect of the present application relates to a process for preparing pure amorphous form of vilazodone hydrochloride comprising:

a) dissolving crystalline vilazodone hydrochloride in a suitable solvent or mixture thereof;
b) optionally filtering the undissolved particles;
c) removing the solvent from the filtrate of step b) by any suitable technique; and
d) drying the product at suitable temperature.

The fifty third aspect of the present application relates to a pharmaceutically acceptable dosage form comprising pure amorphous vilazodone hydrochloride and one or more pharmaceutically acceptable excipients.

The fifty fourth aspect of the present application relates to a process for preparing vilazodone free base comprising the condensation of 5-(piperazin-1-yl)benzofuran-2-carboxamide with 3-(4-chlorobutyl)-1H-indole-5-carbonitrile in a suitable solvent in presence of a base and an additive selected from a group of an ionic additive, a phase transfer catalyst and mixture thereof.

The fifty fifth aspect of the present application relates to a crystalline form of vilazodone free base (hereinafter designated as form I) which may be characterized by X-ray powder diffraction (PXRD) pattern having peaks at about 5.8, 18.6 and 20.8±0.2 degrees 2θ. The form I of vilazodone free base may be characterized by PXRD pattern substantially as illustrated in FIG. 21.

The fifty sixth aspect of the present application relates to the use of crystalline form I of vilazodone free base as an intermediate for the preparation of vilazodone hydrochloride.

The fifty seventh aspect of the present application relates to a process for preparing 3-(4-chlorobutanoyl)-1H-indole-5-carbonitrile by treating 5-cyano indole with 4-chlorobuyryl chloride in presence of titanium tetrachloride.

The fifty eighth aspect of the present application relates to a process for preparing 3-(4-chlorobutyl)-1H-indole-5-carbonitrile by reducing 3-(4-chlorobutanoyl)-1H-indole-5-carbonitrile in presence of sodium borohydride and boron trifluoride etherate.

The fifty ninth aspect of the present application relates to pharmaceutical compositions comprising crystalline form B or C or D or E or F or G or H or amorphous solid dispersion with a pharmaceutically acceptable carrier such as polyvinylpyrrolidone (PVP) or hydroxypropyl methylcellulose (HPMC) of vilazodone hydrochloride or pure amorphous vilazodone hydrochloride or mixtures thereof, together with one or more pharmaceutically acceptable excipients.

BRIEF DESCRIPTION OF THE DRAWING

FIG. 1 is an illustration of a PXRD pattern of crystalline form B of vilazodone hydrochloride as obtained from example 1a.

FIG. 6 is an illustration of a PXRD pattern of crystalline form C of vilazodone hydrochloride as obtained from example 2a.

DETAILED DESCRIPTION

The first aspect of the present application relates to crystalline forms B, C, D, E, F, G, H and amorphous solid dispersions of vilazodone hydrochloride; and processes for their preparation.

The second aspect of the present application relates to crystalline form B of vilazodone hydrochloride characterized by its powder X-ray diffraction (PXRD) pattern having peaks at about 7.10, 14.96, 17.31 and 21.64±0.2 degrees 2θ. In embodiments, the present application relates to crystalline form B of vilazodone hydrochloride characterized by its PXRD pattern having additional peaks located at about 19.63, 22.40, 22.99, 25.91 and 26.72±0.2 degrees 2θ. Still in other embodiments, the present application relates to crystalline form B of vilazodone hydrochloride characterized by its PXRD pattern having additional peaks located at about 12.10 and 12.66±0.2 degrees 2θ.

The third aspect of the present application relates to crystalline form B of vilazodone hydrochloride that can be characterized by a PXRD pattern having peaks located substantially as illustrated in the pattern of FIG. 1 or FIG. 2 or FIG. 3 or FIG. 4 or FIG. 5.

Figure 17:
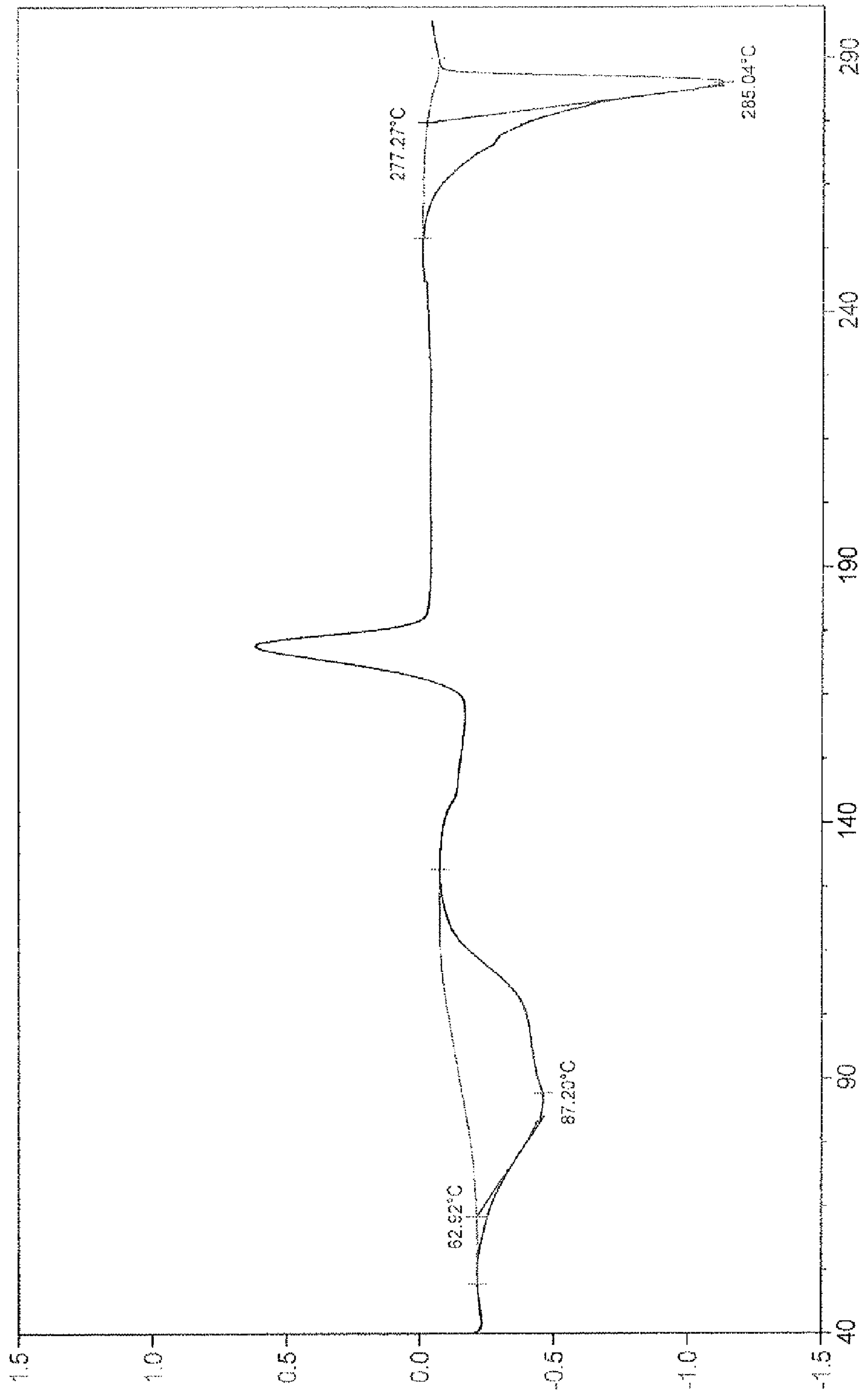
FIG. 17 is an illustration of a DSC thermogram of crystalline form B of vilazodone hydrochloride.

The fourth aspect of the present application relates to crystalline form B of vilazodone hydrochloride that can be characterized by a DSC thermogram substantially as illustrated in the pattern of FIG. 17.

The DSC measurement gives a phase transition between about 140° C. and about 200° C. which ultimately melts from about 270° C. to about 290° C.

Figure 18:
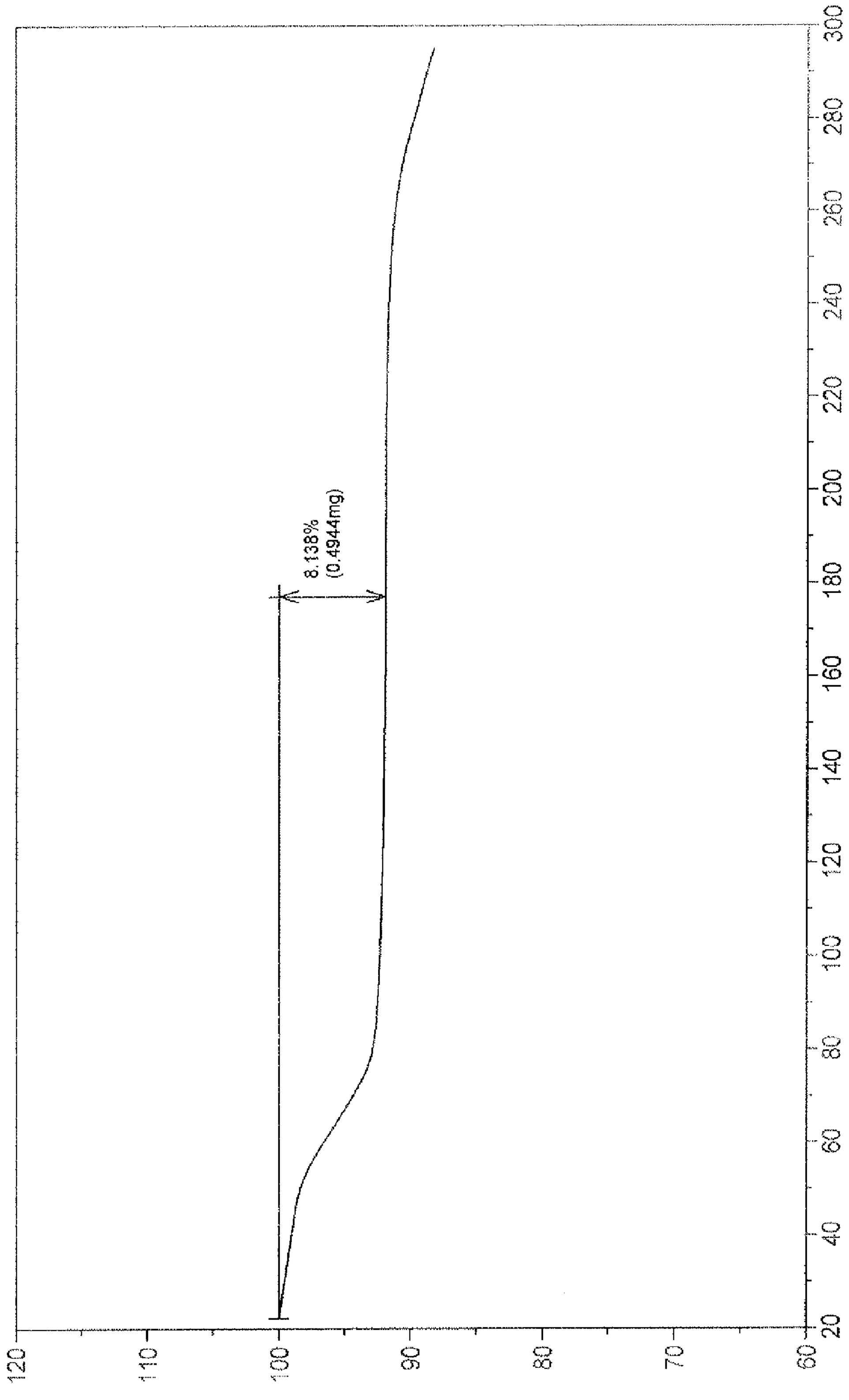
FIG. 18 is an illustration of a TGA thermogram of crystalline form B of vilazodone hydrochloride.

The fifth aspect the present application relates to crystalline form B of vilazodone hydrochloride that can be characterized by a TGA thermogram substantially as illustrated in the pattern of FIG. 18.

Figure 19:
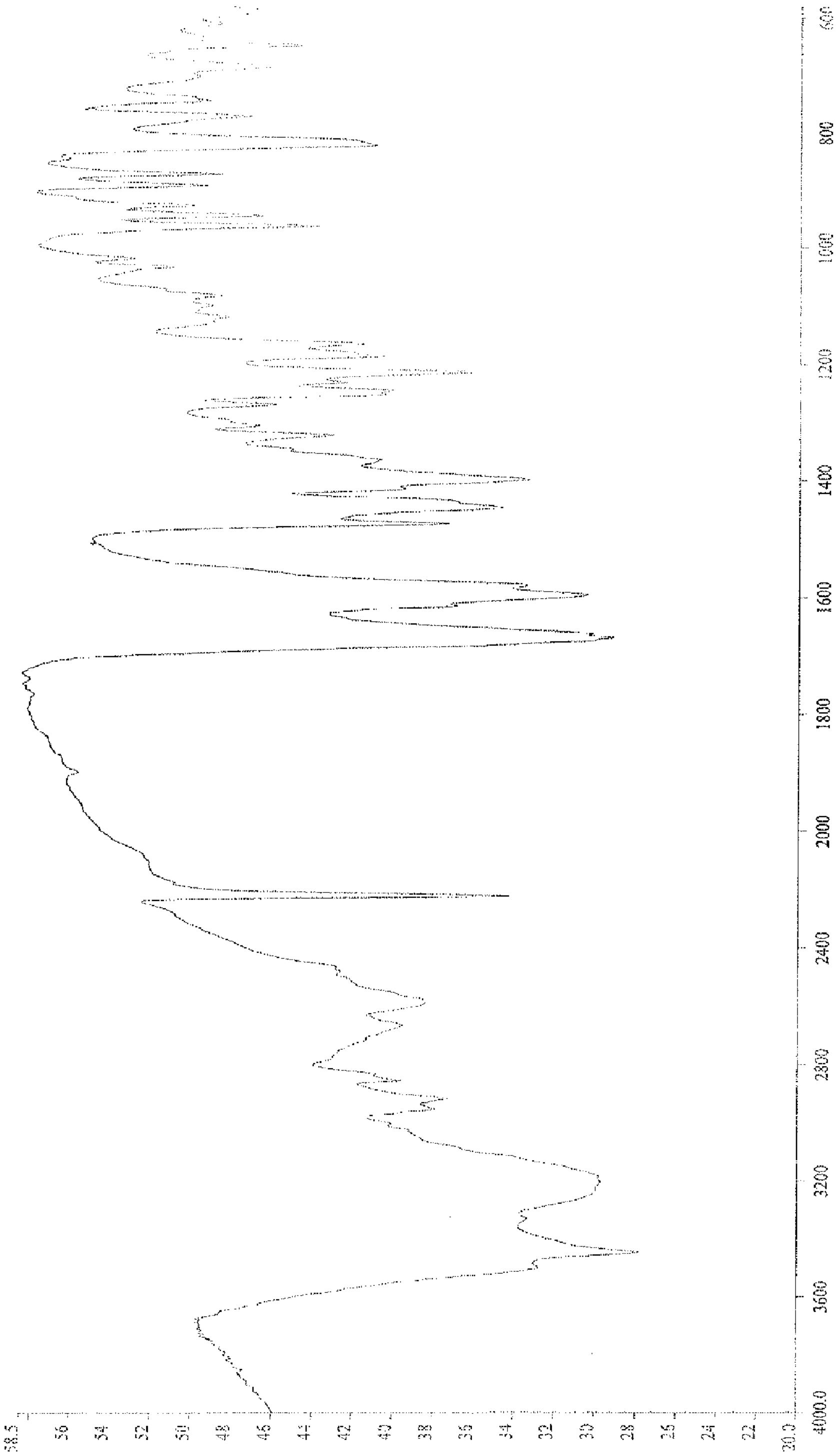
FIG. 19 is an illustration of an IR spectrum of crystalline form B of vilazodone hydrochloride.

The sixth aspect of the present application relates to crystalline form B of vilazodone hydrochloride that can be characterized by an IR spectrum substantially as illustrated in the pattern of FIG. 19.

Figure 23:
FIG. 23 is an illustration of SEM pattern of crystalline form B of vilazodone hydrochloride.

The seventh aspect of the present application relates to crystalline form B of vilazodone hydrochloride that can be characterized by a scanning electron microscopic pattern substantially as illustrated in FIG. 23.

The eighth aspect of the present application relates to a process for preparing crystalline form B of vilazodone hydrochloride, which comprises:

a) providing a mixture of vilazodone free base in suitable solvent or mixtures thereof;
b) combining hydrochloric acid with the mixture of step a); and
c) isolating crystalline form B of vilazodone hydrochloride.

In one of the embodiments of step a), any physical form of vilazodone free base may be utilized, which may be crystalline or amorphous, for providing the mixture of vilazodone free base in suitable solvent or mixtures thereof. In another embodiment of step a), any physical form of vilazodone free base may be utilized, which may be anhydrous or hydrate, for providing the mixture of vilazodone free base in suitable solvent or mixtures thereof. The water content of hydrated vilazodone free base may vary from about 2.0% to about 10.0% w/w, more preferably from about 3.0% to about 8.0% w/w.

Vilazodone free base is mixed with a suitable solvent at any suitable temperature range, specifically at about 0° C. to about 50° C. and more specifically at about 25° C. to about 35° C. The mixture may optionally be cooled at about 0° C. to about −30° C., specifically at about −5° C. to about −20° C. and most specifically at about −10° C. to about −15° C.

Specifically, the suitable solvent includes but not limited to an alcoholic solvent, water and mixture thereof. The alcoholic solvent which includes, but not limited to $C_1$-$C_6$ branched or linear aliphatic alcohols such as methanol, ethanol, propanol, n-butanol, isopropanol, tert-butanol. More specifically, the solvent is methanol.

In one embodiment of step a), the seed crystals of form B of vilazodone hydrochloride is optionally added to the mixture of vilazodone free base and suitable solvent. When the seed crystals are added, they are added in a quantity from about 0.1% w/w to about 50% w/w over the weight of free base. Specifically, the seed crystals are added in a quantity from about 0.5% to about 20% w/w and more specifically the seed crystals are added in a quantity from about 1% to about 10% w/w.

The hydrochloric acid used in step b) may include but not limited to aqueous hydrochloric acid of any suitable strength or hydrochloric acid dissolved in any suitable solvent. Specifically, hydrogen chloride gas is passed through methanol to produce methanolic hydrochloric acid which is used in step b).

In embodiments of step b), mode of addition of step a) mixture with hydrochloric acid can be achieved by adding the hydrochloric acid solution in a suitable solvent to the mixture of step a) or reverse mode of addition can also be employed. The addition may be slow or at once while maintaining a temperature of about −30° C. to about 30° C. Specifically, the hydrochloric acid solution may be added slowly to the mixture of step a) at a temperature of about −20° C. to about −5° C. More specifically, the hydrochloric acid solution may be added slowly to the mixture of step a) at a temperature of about −10° C. to about −15° C. After complete addition, the mixture is stirred for about 30 minutes to about 5 hours at the same temperature. Specifically, the mixture is stirred for about 45 minutes to about 3 hours at the same temperature and more specifically the mixture is stirred for about 1 hour to about 2 hours at the same temperature.

The strength of hydrochloric acid solution in a suitable solvent is from about 3% w/w to about 30% w/w. Specifically, the strength of hydrochloric acid solution in a suitable solvent is from about 5% w/w to about 20% w/w. Hydrochloric acid solution in a suitable solvent can be prepared by purging of dry hydrogen chloride gas in a suitable solvent or mixtures thereof by the methods known in the prior art or by mixing the hydrochloric acid with suitable solvent or mixtures thereof. The suitable solvent includes but not limited to alcoholic solvent, water and mixture thereof. The alcoholic solvent includes but not limited to $C_1$-$C_6$ branched or linear aliphatic alcohols such as methanol, ethanol, propanol, n-butanol, isopropanol, tert-butanol. Specifically, the solvent is methanol. The hydrochloric acid solution in a suitable solvent may contain water. Water, if present, may vary from about 0.5% to 10.0% w/w, more specifically from about 1.0% to about 5.0% w/w.

In embodiments of step c), isolating crystalline form B of vilazodone hydrochloride may optionally involve one or more methods known in the art including removal of solvent by techniques known in the art e.g. evaporation, distillation, filtration of isolated solid and the like. Suitable temperatures for isolation may be less than about 25° C., less than about 10° C., or any other suitable temperatures. Filtration can be achieved by any means known in the art. Specifically, filtration can be achieved by using Buchner funnel or pressure nutsch filter (PNF) or jacketed agitated nutsch filter drier (ANFD). While using jacketed ANFD equipment, the temperature of jacket may be maintained at about −20° C. to about 5° C. by circulating brine solution. After the filtration, the wet solid is washed with cold alcoholic solvent and suck-dried for about 30 minutes to about 3 hours. In case of filtration by PNF, the suck-drying is achieved by applying a positive pressure of dry air or nitrogen. In case of filtration by jacketed ANFD, the suck-drying is achieved by applying vacuum while maintaining the atmospheric pressure by supplying dry air or nitrogen. In case of filtration by Buchner funnel, the suck-drying is achieved by applying a vacuum. Specifically, the solid is washed with cold methanol and suck-dried for about 1 hour to about 3 hours. In an embodiment, the filtration of solid may be achieved using ANFD. After the suck-drying, the solid is optionally humidified with humid air of relative humidity of about 10% to about 95% for about 30 minutes to about 2 days. Specifically, the solid is optionally humidified with humid air of relative humidity of about 30% to about 70% for about 1 hour to about 40 hours.

The solid obtained from step c) may be collected using techniques such as by scraping, or by shaking the container, or other techniques specific to the equipment used. Optionally, the collected material is dried. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. and most specifically less than about 40° C. The drying may be carried out for any time period required for obtaining a desired product quality, such as from about 5 minutes to about 24 hours, or longer.

In one embodiment, the humidification and the drying step can be performed either sequentially or simultaneously. Specifically, crystalline form B of vilazodone hydrochloride may be filtered by ANFD and subjected to humidification in humidification chamber with a humid air having relative humidity of about 30% to about 70% for about 1 hour to about 40 hours followed by drying using any of an air tray dryer, vacuum tray dryer, fluidized bed dryer, spin flash dryer, flash dryer, and the like. More specifically, crystalline form B of vilazodone hydrochloride may be filtered by ANFD and subjected to simultaneous humidification and drying by supplying humid air having relative humidity of about 30% to about 70% in air tray dryer or fluidized bed dryer for about 1 hour to about 40 hours.

The obtained crystalline form B of vilazodone hydrochloride may optionally be subjected to a particle size reduction procedure to produce desired particle sizes and distributions. Milling or micronization may be performed before drying, or after the completion of drying of crystalline form B of vilazodone hydrochloride. Equipment that may be used for particle size reduction includes but not limited to ball mill, roller mill, hammer mill, and jet mill.

The particle size analysis may be done by any suitable instrument. In an embodiment, the particle size of crystalline form B of vilazodone hydrochloride obtained by the process of the present application may be analyzed by Malvern instrument using known methods in the art.

The particle size of the crystalline form B of vilazodone hydrochloride as obtained by a process as described above is as follows:

D(0.1): about 1-7 μm

D(0.5): about 5-15 μm

D(0.9): about 12-25 μm.

The crystalline form B of vilazodone hydrochloride may contain water and typically the water content of crystalline form B of vilazodone hydrochloride may vary from about 3.0% to about 15.0% w/w, more preferably from about 4.0% to about 10.0% w/w, and most preferably from about 6% to about 8% w/w.

It is observed that the said variation of water in the crystalline form B of vilazodone hydrochloride may not affect the stability and PXRD pattern which is in accordance with any of the figures mentioned in the present application that are directed to crystalline form B of vilazodone hydrochloride.

The HPLC purity of form B of vilazodone hydrochloride obtained by the process of the present application may be more than about 95%. Specifically, the HPLC purity of form B of vilazodone hydrochloride obtained by the process of the present application may be more than about 98%. More specifically, the HPLC purity of form B of vilazodone hydrochloride obtained by the process of the present application may be more than about 99%.

A suitable packaging and storing condition is essential for any active ingredient to ensure its polymorphic as well as chemical stability for longer period. Hence, one embodiment of the present application relates to a suitable packaging and storing condition which is required for polymorphic as well as chemical stability of crystalline form B of vilazodone hydrochloride.

The ninth aspect of the present application relates to a process for packaging and storing of crystalline form B of vilazodone hydrochloride comprises the following steps:

a) placing crystalline form B of vilazodone hydrochloride in a clear polyethylene bag tied with a thread,
b) placing the primary packing containing crystalline form B of vilazodone hydrochloride inside a black colour polyethylene bag containing silica gel and sealing it,
c) placing the above double polyethylene bag inside a triple laminated bag containing silica gel and
d) placing the sealed triple laminated bag inside a closed high density polyethylene (HDPE) container and storing at room temperature.

Optionally, all the polyethylene bags are purged with nitrogen before use.

The tenth aspect of the present application relates to a pharmaceutically acceptable dosage form comprising crystalline form B of vilazodone hydrochloride and one or more pharmaceutically acceptable excipients.

The eleventh aspect of the present application relates to crystalline form C of vilazodone hydrochloride characterized by its powder X-ray diffraction (PXRD) pattern having peaks at about 10.50, 14.20 and 20.20±0.2 degrees 2θ. In embodiments, the present application relates to crystalline form C of vilazodone hydrochloride characterized by its PXRD pattern having an additional peak located at about 9.06±0.2 degrees 2θ.

Figure 6:
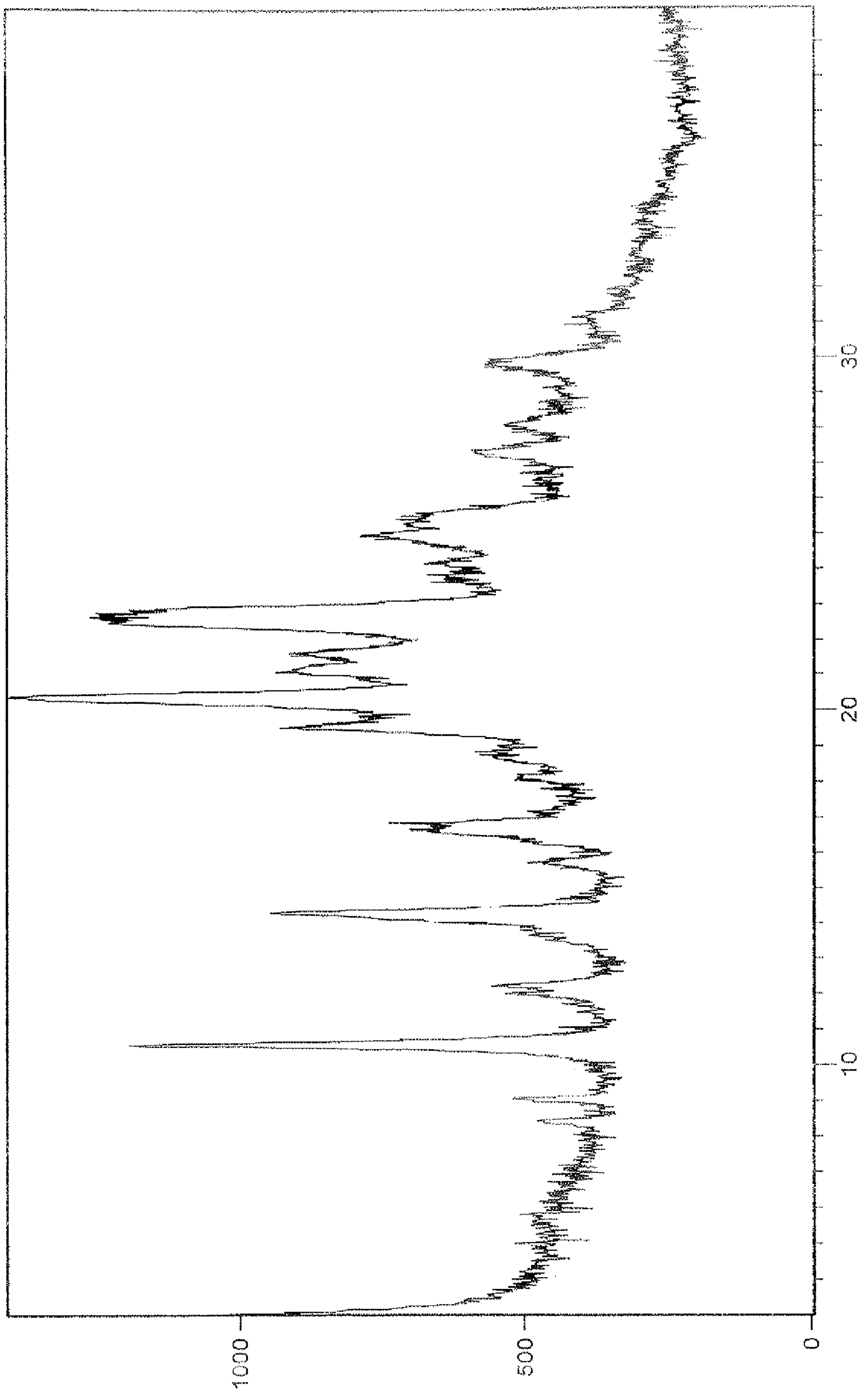
Figure 7:
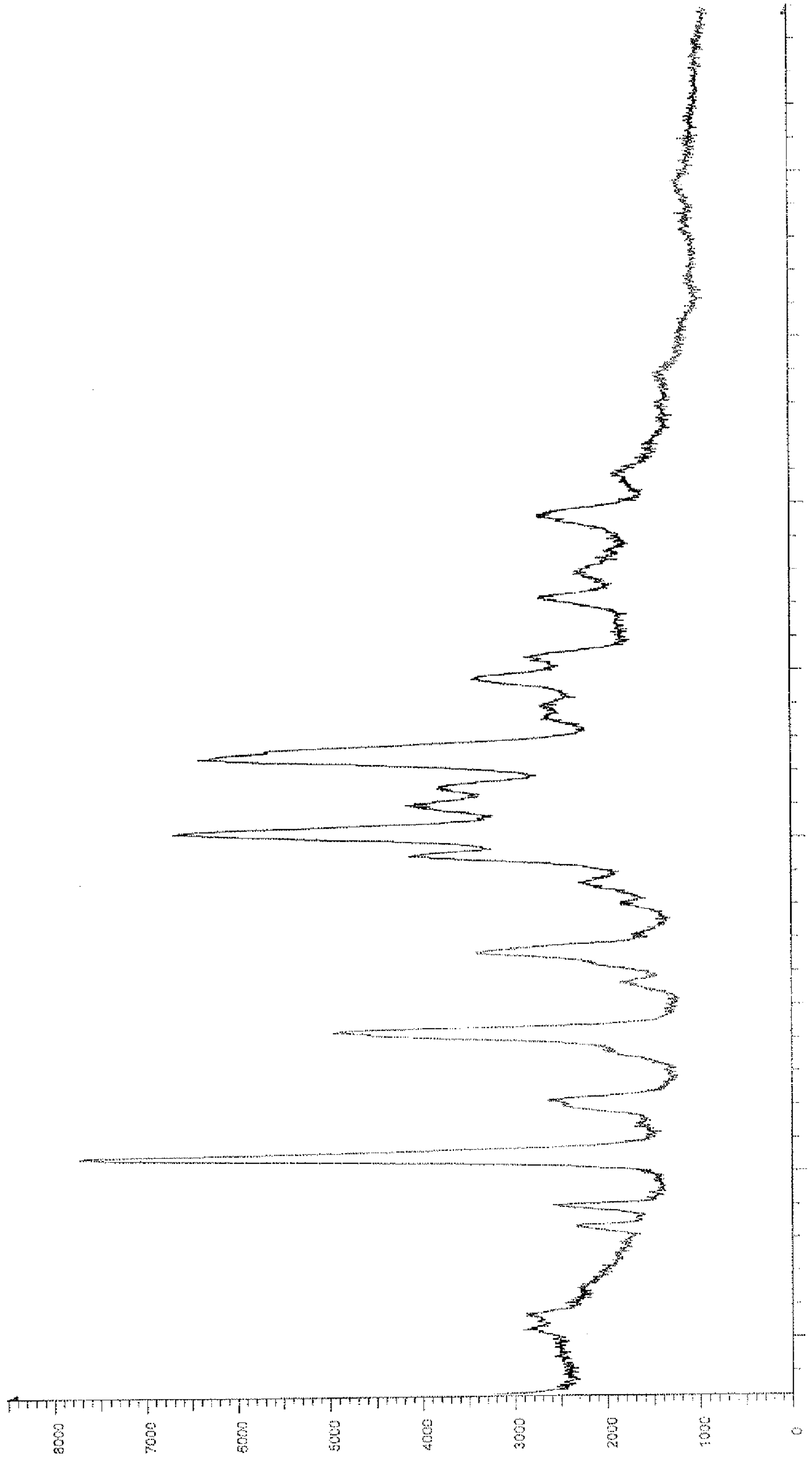
FIG. 7 is an illustration of a PXRD pattern of crystalline form C of vilazodone hydrochloride as obtained from example 2b.
Figure 8:
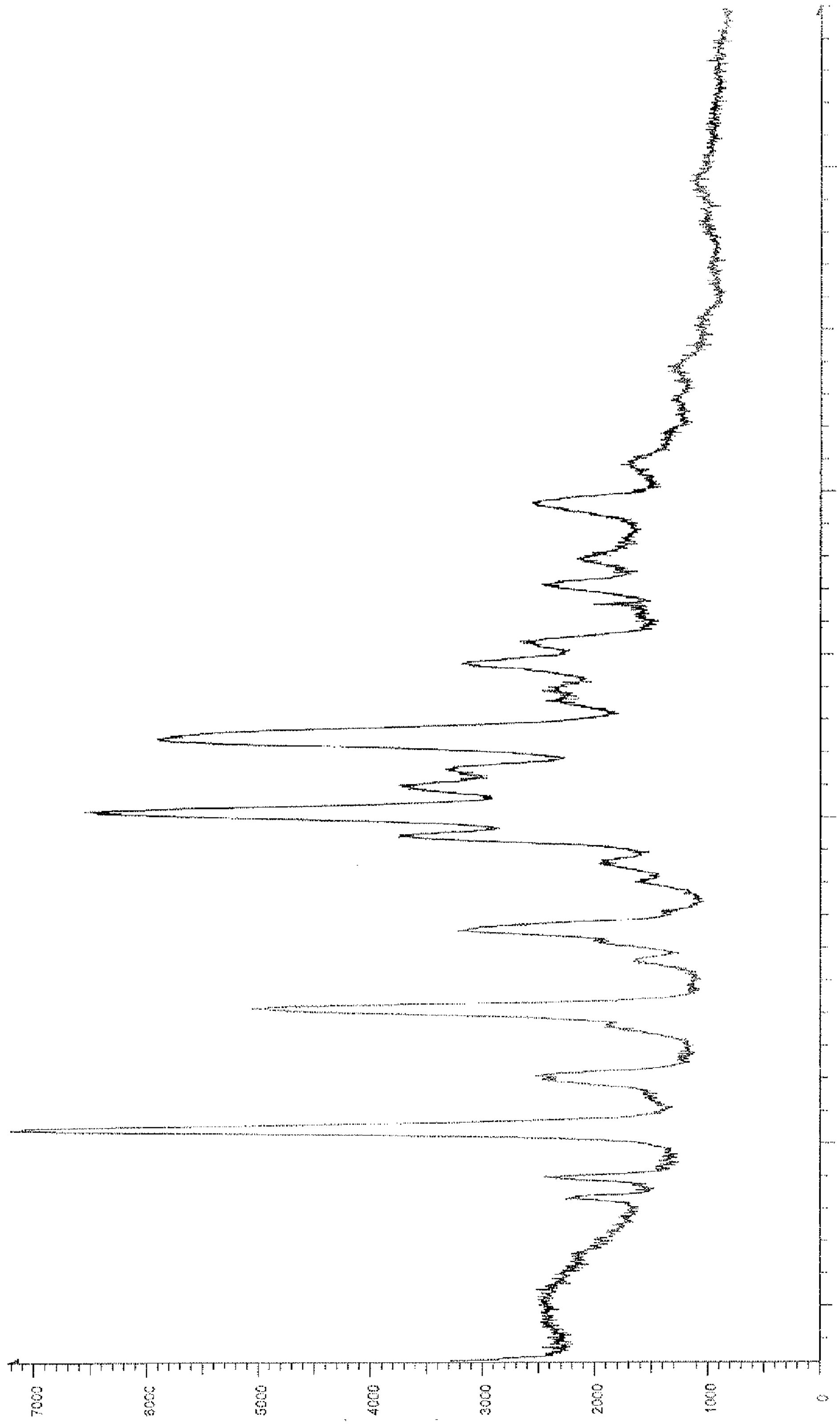
FIG. 8 is an illustration of a PXRD pattern of crystalline form C of vilazodone hydrochloride as obtained from example 2c.

The twelfth aspect of the present application relates to crystalline form C of vilazodone hydrochloride that can be characterized by a PXRD pattern having peaks located substantially as illustrated in the pattern of FIG. 6 or FIG. 7 or FIG. 8.

The thirteenth aspect of the present application relates to process for preparing crystalline form C of vilazodone hydrochloride by drying the crystalline form B of vilazodone hydrochloride with a suitable drying technique.

The crystalline form C of vilazodone hydrochloride characterized by its powder X-ray diffraction (PXRD) pattern having peaks at about 10.50, 14.20 and 20.20±0.2 degrees 2θ which may have an additional peak located at about 9.06±0.2 degrees 2θ, can be prepared by drying the crystalline form B of vilazodone hydrochloride characterized by its PXRD pattern having peaks at about 7.10, 14.96, 17.31 and 21.64±0.2 degrees 2θ and additional peaks located at about 19.63, 22.40, 22.99, 25.91 and 26.72±0.2 degrees 2θ and additional peaks located at about 12.10 and 12.66±0.2 degrees 2θ with a suitable drying technique, preferably air tray dryer (ATD) or vacuum tray dryer (VTD). Drying can also be suitably carried out in an air oven, or using a fluidized bed drier, spin flash dryer, flash dryer and the like, and drying equipment selection is well within the ordinary skill in the art and it is also within the scope of the present application.

The drying may be carried out at atmospheric pressure or above, or under reduced pressures, at temperatures less than about 120° C., less than about 100° C., less than about 90° C., or any other suitable temperatures. The drying may be carried out for any time period required for obtaining the desired crystalline form C of vilazodone hydrochloride characterized by its powder X-ray diffraction (PXRD) pattern having peaks at about 10.50, 14.20 and 20.20±0.2 degrees 2θ which may have an additional peak located at about 9.06±0.2 degrees 2θ from crystalline form B of vilazodone hydrochloride characterized by its PXRD pattern having peaks at about 7.10, 14.96, 17.31 and 21.64±0.2 degrees 2θ and additional peaks located at about 19.63, 22.40, 22.99, 25.91 and 26.72±0.2 degrees 2θ and additional peaks located at about 12.10 and 12.66±0.2 degrees 2θ, such as from about 5 minutes to about 24 hours, or longer.

The obtained crystalline form C may optionally be subjected to a particle size reduction procedure to produce desired particle sizes and distributions. Milling or micronization may be performed before drying, or after the completion of drying of the crystalline form C. Equipment that may be used for particle size reduction include, without limitation thereto, ball, roller, and hammer mills, and jet mills.

The above crystalline form C of vilazodone hydrochloride may contain water and typically the water content in crystalline form C of vilazodone hydrochloride may vary from 3.0% to 15.0% w/w, more preferably 4.0% to 10.0% w/w.

It is observed that the said variation of water in the vilazodone hydrochloride crystalline form C may not affect the stability and PXRD pattern of the crystalline form C in accordance with any of the figures mentioned in the present application that are directed to crystalline form C of vilazodone hydrochloride.

The fourteenth aspect of the present application relates to a pharmaceutically acceptable dosage form comprising crystalline form C of vilazodone hydrochloride and one or more pharmaceutically acceptable excipients.

The fifteenth aspect of the present application relates to solvates of vilazodone hydrochloride with solvents selected from the group consisting of halogenated hydrocarbons, aliphatic esters, aliphatic amides, dimethyl sulfoxide, N-methyl-2-pyrrolidone and mixtures thereof.

The sixteenth aspect of the present application relates to crystalline vilazodone hydrochloride form D characterized by its powder X-ray diffraction (PXRD) pattern having peaks at about 13.39, 13.67, 16.00, 21.22 and 24.61±0.2 degrees 2θ. In embodiments, the present application relates to crystalline vilazodone hydrochloride form D characterized by its PXRD pattern having additional peaks located at about 5.53, 9.60, 10.54 and 11.09±0.2 degrees 2θ.

Figure 9:
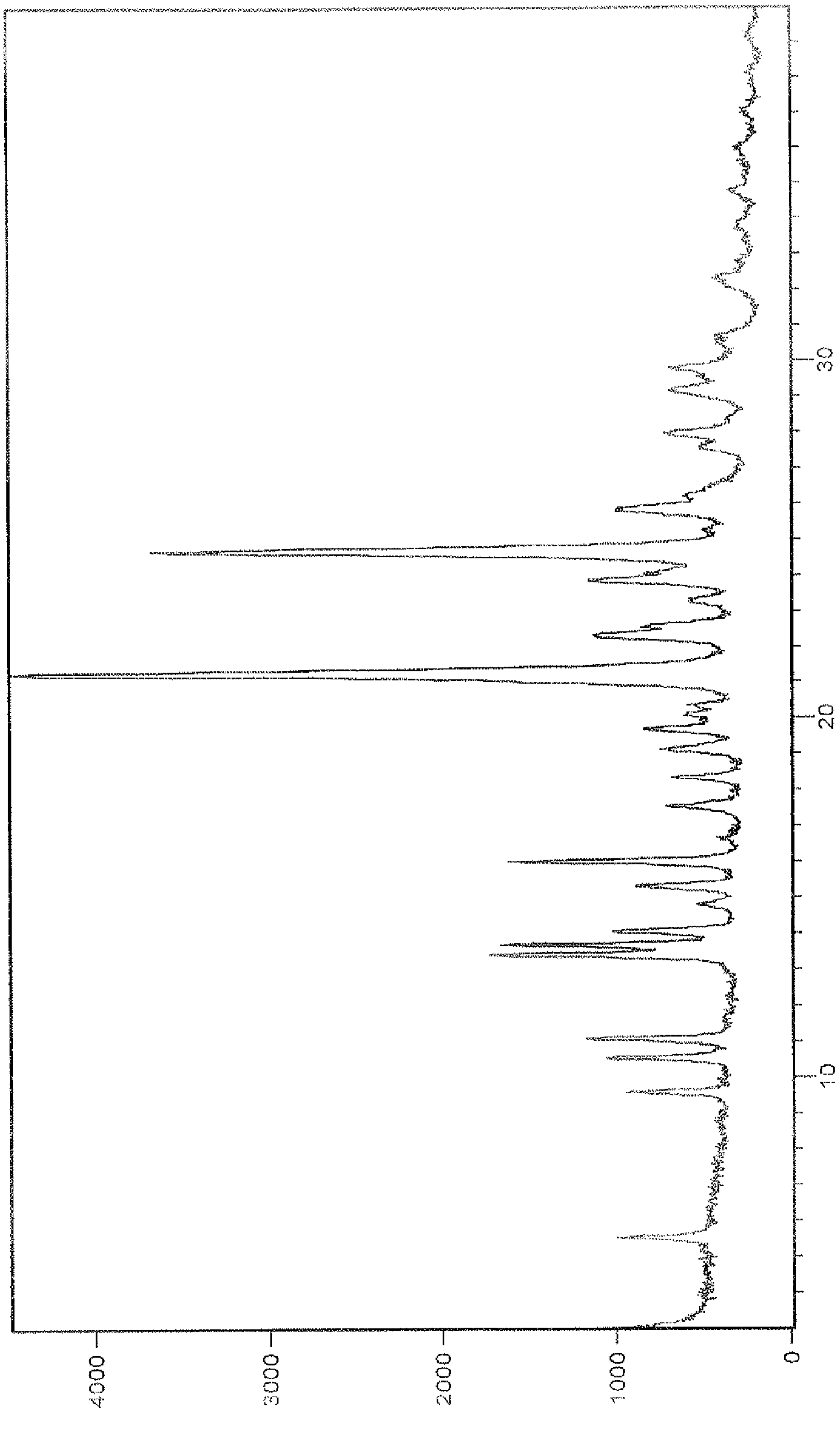
FIG. 9 is an illustration of a PXRD pattern of crystalline vilazodone hydrochloride form D.

The seventeenth aspect of the present application relates to crystalline vilazodone hydrochloride form D that can be characterized by a PXRD pattern having peaks located substantially as illustrated in the pattern of FIG. 9.

The above crystalline form D of vilazodone hydrochloride is a mixed solvate of dimethyl sulfoxide and ethyl acetate. Preferably, the crystalline form D of vilazodone hydrochloride contains dimethyl sulfoxide content from about 1.0% to 15.0% w/w, more preferably 2.0% to 10.0% w/w whereas ethyl acetate content may vary from 1.0% to 10.0% w/w, more preferably 2.0% to 8.0% w/w.

The eighteenth aspect of the present application relates to process for preparing crystalline vilazodone hydrochloride form D, which comprises:

a) providing a solution of vilazodone hydrochloride in dimethyl sulfoxide solvent;

b) combining ethyl acetate with the solution of step a); and c) isolating crystalline vilazodone hydrochloride form D.

The nineteenth aspect of the present application relates to a pharmaceutically acceptable dosage form comprising crystalline form D of vilazodone hydrochloride and one or more pharmaceutically acceptable excipients.

The twentieth aspect of the present application relates to crystalline vilazodone hydrochloride form E characterized by its powder X-ray diffraction (PXRD) pattern having peaks at about 10.62, 16.18 and 21.42±0.2 degrees 2θ. In embodiments, the present application relates to crystalline vilazodone hydrochloride form E characterized by its PXRD pattern having additional peaks located at about 5.55, 9.54 and 11.06±0.2 degrees 2θ.

Figure 10:
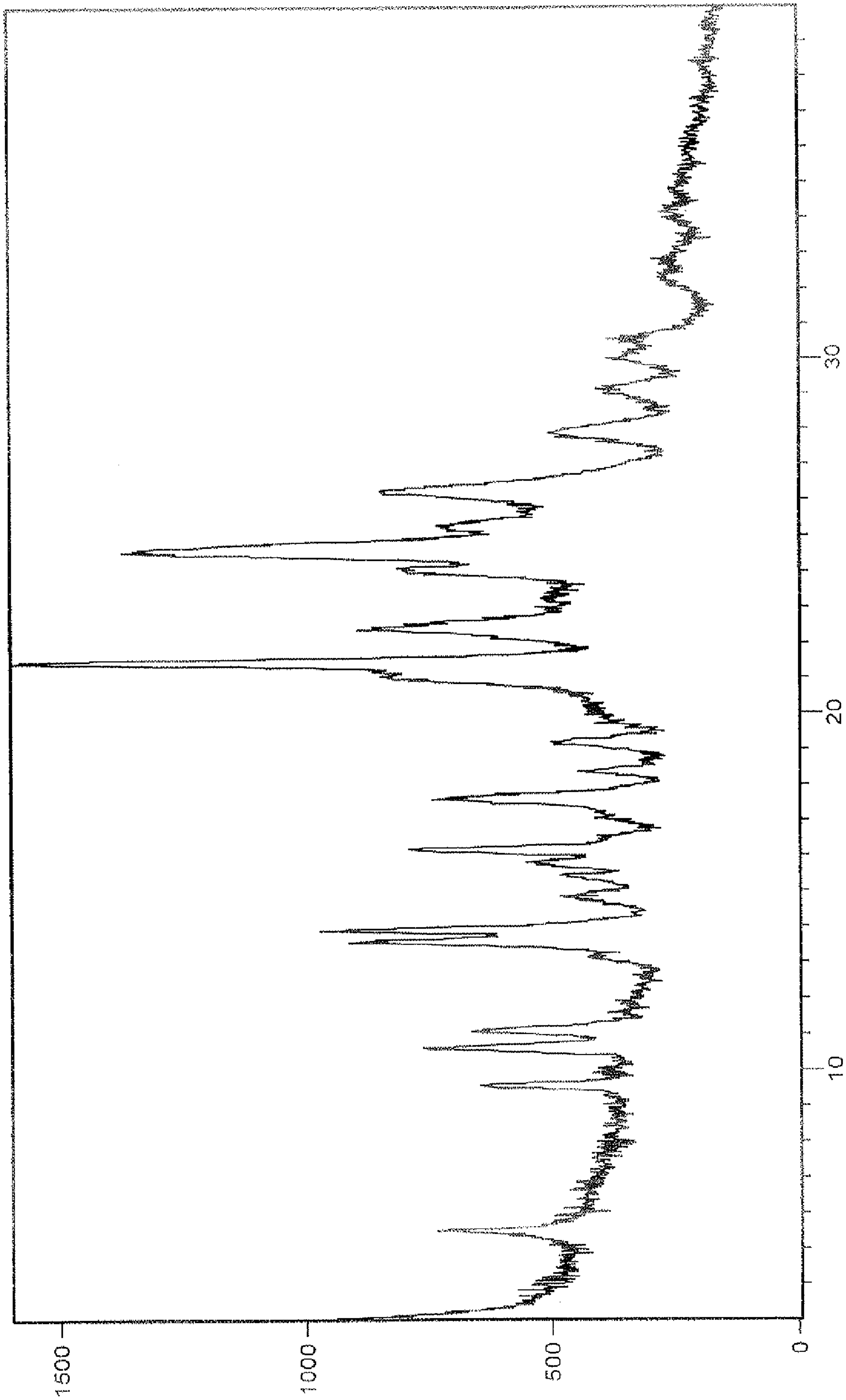
FIG. 10 is an illustration of a PXRD pattern of crystalline vilazodone hydrochloride form E.

The twenty first aspect of the present application relates to crystalline vilazodone hydrochloride form E that can be characterized by a PXRD pattern having peaks located substantially as illustrated in the pattern of FIG. 10.

The above crystalline form E of vilazodone hydrochloride is a mixed solvate of N-methyl-2-pyrrolidone and dichloromethane. Preferably, the crystalline form E of vilazodone hydrochloride contains N-methyl-2-pyrrolidone content from about 1.0% to 10.0% w/w, more preferably 2.0% to 8.0% w/w whereas dichloromethane content may vary from 1.0% to 10.0% w/w, more preferably 2.0% to 8.0% w/w.

The twenty second aspect of the present application relates to process for preparing crystalline vilazodone hydrochloride form E, which comprises:

a) providing a solution of vilazodone hydrochloride in N-methyl-2-pyrrolidone solvent;

b) combining dichloromethane with the solution of step a); and c) isolating crystalline vilazodone hydrochloride form E.

The twenty third aspect of the present application relates to a pharmaceutically acceptable dosage form comprising crystalline form E of vilazodone hydrochloride and one or more pharmaceutically acceptable excipients.

The twenty fourth aspect of the present application relates to crystalline vilazodone hydrochloride form F characterized by its powder X-ray diffraction (PXRD) pattern having peaks at about 13.45, 13.73, 21.24 and 24.85±0.2 degrees 2θ. In embodiments, the present application relates to crystalline vilazodone hydrochloride form F characterized by its PXRD pattern having additional peaks located at about 10.65, 11.07 and 16.07±0.2 degrees 2θ. Still in other embodiments, the present application relates to crystalline vilazodone hydrochloride form F characterized by its PXRD pattern having additional peaks located at about 5.55, 9.61 and 15.31±0.2 degrees 2θ.

Figure 11:
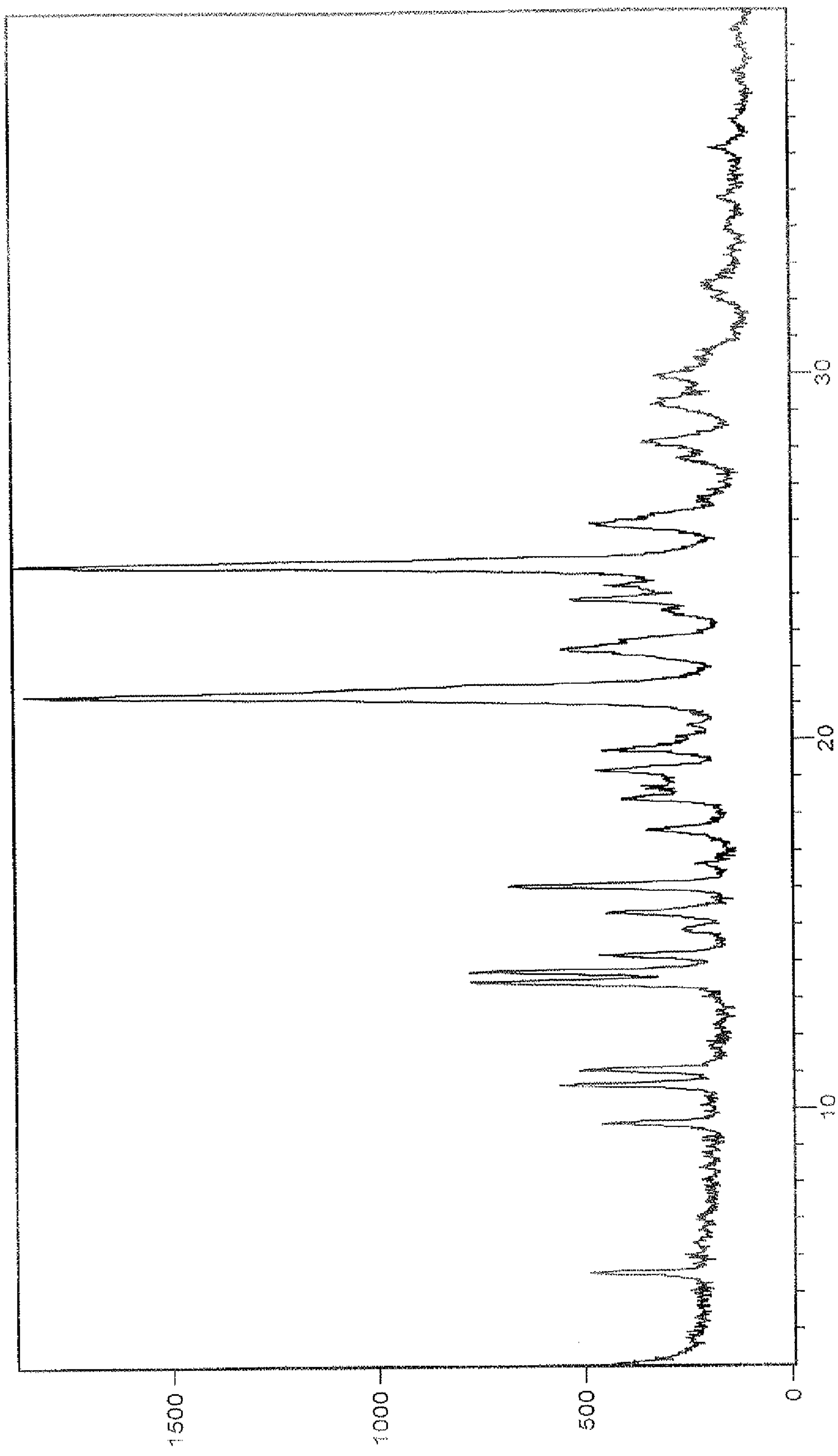
FIG. 11 is an illustration of a PXRD pattern of crystalline vilazodone hydrochloride form F.

The twenty fifth aspect of the present application relates to crystalline vilazodone hydrochloride form F that can be characterized by a PXRD pattern having peaks located substantially as illustrated in the pattern of FIG. 11.

The above crystalline form F of vilazodone hydrochloride is a mixed solvate of N,N-dimethylformamide and ethyl acetate. Preferably, the crystalline form F of vilazodone hydrochloride contains N,N-dimethylformamide content from about 1.0% to 8.0% w/w, more preferably 2.0% to 6.0% w/w whereas ethyl acetate content may vary from 1.0% to 10.0% w/w, more preferably 2.0% to 8.0% w/w.

The twenty sixth aspect of the present application relates to process for preparing crystalline vilazodone hydrochloride form F, which comprises:

a) providing a solution of vilazodone hydrochloride in N,N-dimethylformamide solvent;

b) combining ethyl acetate with the solution of step a); and c) isolating crystalline vilazodone hydrochloride form F.

The twenty seventh aspect of the present application relates to a pharmaceutically acceptable dosage form comprising crystalline form F of vilazodone hydrochloride and one or more pharmaceutically acceptable excipients.

The crystalline vilazodone hydrochloride forms D, E and F is a complex of variable stoichiometry formed by a solute (in this application, a compound of formula (I)) and solvents. Such solvents for the purpose of the present application may not interfere with the biological activity of the solute and moreover the solvents are within the permissible limits, wherein solvents are dimethyl sulfoxide, ethyl acetate, N-methyl-2-pyrrolidone, dichloromethane, N,N-dimethylformamide and ethyl acetate.

The vilazodone hydrochloride crystalline forms D, E and F of the present application may contain water which may vary from about 0.05% to 10.0% w/w.

It is observed that the said variation of water and solvents in the vilazodone hydrochloride crystalline forms D, E and F may not affect the stability and PXRD pattern of the crystalline forms D, E and F in accordance with FIG. 9, FIG. 10 and FIG. 11 respectively.

In an aspect, the present application relates to a process for preparing crystalline form D or form E or form F of vilazodone hydrochloride, which comprises:

a) providing a solution of vilazodone hydrochloride in suitable solvent or mixtures thereof;

b) combining an antisolvent with the solution of step a); and c) isolating crystalline form D or form E or form F of vilazodone hydrochloride.

Preferably the suitable solvents which may be used include, but are not limited to halogenated hydrocarbons such as dichloromethane; aliphatic esters such as ethyl acetate; aliphatic amides such as N,N-dimethylformamide; dimethyl sulfoxide, N-methyl-2-pyrrolidone, water and mixtures thereof.

Preferably the suitable antisolvent which may be used include, but are not limited to esters or halogenated hydrocarbon solvent.

In the present application, vilazodone hydrochloride which is used as a starting material for preparing the crystalline form D or form E or form F may be prepared using methods known in the prior art. Alternatively, crystalline form B or crystalline form C or crystalline form G or crystalline form H or mixtures thereof of the present application can also be used for preparing the crystalline form D or form E or form F.

In embodiments of step a), providing a solution of vilazodone hydrochloride may include:

i) direct use of a reaction mixture containing vilazodone hydrochloride that is obtained in the course of its synthesis and that comprises one of the suitable solvents or mixtures thereof, or by combining one of the suitable solvents or mixtures thereof with the reaction mixture; or ii) dissolving vilazodone hydrochloride in one of the suitable solvents or mixtures thereof.

Specifically, the suitable solvents which may be used include, but are not limited to halogenated hydrocarbons such as dichloromethane; aliphatic esters such as ethyl acetate; aliphatic amides such as N,N-dimethylformamide; dimethyl sulfoxide, N-methyl-2-pyrrolidone, water and mixtures thereof.

In embodiments of step a), any physical form of vilazodone hydrochloride may be utilized for providing the solution of vilazodone hydrochloride. The dissolution temperatures may range from about ambient temperature to about the reflux temperature of the solvent, or less than about 100° C., less than about 80° C., less than about 60° C., or any other suitable temperatures, as long as a clear solution of vilazodone hydrochloride is obtained without affecting its quality. The solution may optionally be treated with carbon, flux-calcined diatomaceous earth (e.g., Hyflow™), or any other suitable material to remove color, insoluble materials, improve clarity of the solution, and/or remove impurities that are adsorbable on such material. Optionally, the solution obtained may be treated to remove any insoluble particles. The insoluble particles may be removed suitably by filtration, centrifugation, decantation, or any other suitable techniques under pressure or under reduced pressure. A solution may be filtered by passing through paper, glass fiber, cloth or other membrane material, or a bed of a clarifying agent such as Celite® or Hyflow. Depending upon the concentration and temperature of the solution and the equipment used, the filtration apparatus may optionally be preheated to avoid premature crystallization.

In embodiments of step a) and step b) suitable solvent: antisolvent combination can be selected from dimethyl sulfoxide:ethyl acetate, N-methyl-2-pyrrolidone:dichloromethane and N,N-dimethylformamide:ethyl acetate.

In embodiments of step b), combing the solution of step a) with anti-solvent may be carried out either by adding the solution obtained in step a) to the anti-solvent, or adding an anti-solvent to the solution obtained in step a), to effect a precipitation and both mode of additions are within the scope of the present application. Optionally, the combination with an anti-solvent may be carried out after concentrating the solution obtained in step a). The time taken for complete addition may depend over the reaction condition and it may vary from about 5 minutes to about 60 minutes.

The combined mixture may be further stirred for about 10 minutes to about 10 hours.

In embodiments of step c), isolating crystalline form D or form E or form F of vilazodone hydrochloride may optionally involve one or more methods including removal of solvent by techniques known in the art e.g. evaporation, distillation, filtration of precipitated solid and the like; cooling; concentrating the mass; adding seed crystals to induce crystallization; and the like. Stirring or other alternate methods such as shaking, agitation, and the like, may also be employed for the isolation. Suitable temperatures for isolation may be less than about 40° C., less than about 30° C., or any other suitable temperatures.

The solid obtained from step c) may be collected using techniques such as by scraping, or by shaking the container, or other techniques specific to the equipment used. The isolated solid may be optionally further dried to afford crystalline forms D or E or F of vilazodone hydrochloride.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, at temperatures less than about 100° C., less than about 80° C., less than about 60° C., or any other suitable temperatures. The drying may be carried out for any time period required for obtaining a desired product quality, such as from about 5 minutes to about 24 hours, or longer.

The obtained crystalline forms D, E or F may optionally be subjected to a particle size reduction procedure to produce desired particle sizes and distributions. Milling or micronization may be performed before drying, or after the completion of drying of the crystalline forms D, E or F. Equipment that may be used for particle size reduction include, without limitation thereto, ball, roller, and hammer mills, and jet mills.

The twenty eighth aspect of the present application relates to crystalline form G of vilazodone hydrochloride characterized by its powder X-ray diffraction (PXRD) pattern having peaks at about 10.71, 16.59, 20.58 and 22.27 and ±0.2 degrees 2θ. In embodiments, the present application relates to crystalline form G of vilazodone hydrochloride characterized by its PXRD pattern having additional peaks located at about 8.61, 21.33, 24.30 and 25.01±0.2 degrees 2θ. Still in other embodiments, the present application relates to crystalline form G of vilazodone hydrochloride characterized by its PXRD pattern having additional peaks located at about 15.41 and 19.40±0.2 degrees 2θ.

Figure 13:
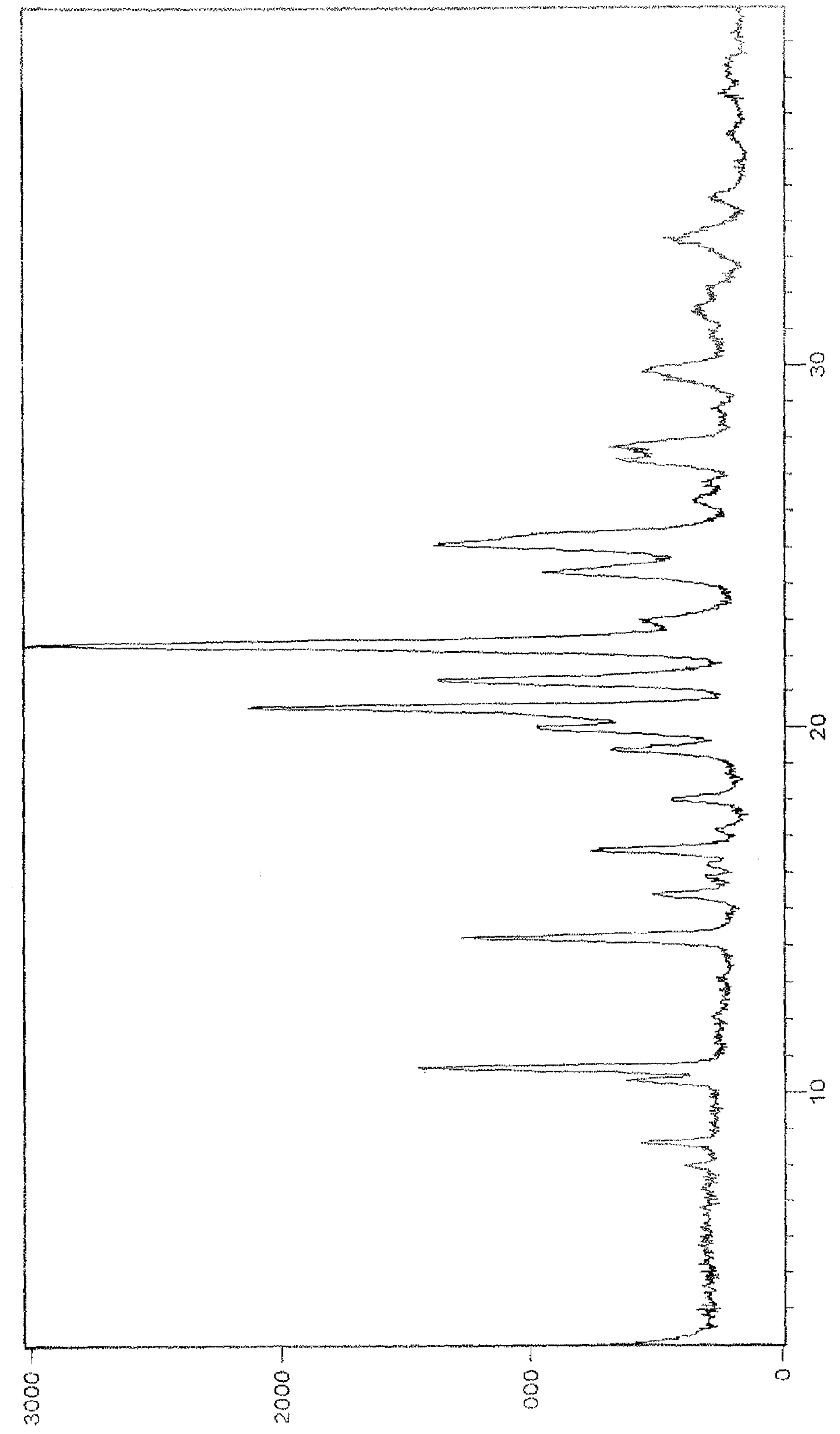
FIG. 13 is an illustration of a PXRD pattern of crystalline form G of vilazodone hydrochloride.

The twenty ninth aspect of the present application relates to crystalline form G of vilazodone hydrochloride that can be characterized by a PXRD pattern having peaks located substantially as illustrated in the pattern of FIG. 13.

The thirtieth aspect of the present application relates to a process for preparing crystalline form G of vilazodone hydrochloride, which comprises:

a) providing a mixture of vilazodone free base in suitable solvent or mixtures thereof;
b) combining hydrochloric acid with the mixture of step a); and
c) isolating crystalline form G of vilazodone hydrochloride.

In one of the embodiments of step a), any physical form of vilazodone free base may be utilized, which may be crystalline or amorphous, for providing the mixture of vilazodone free base in suitable solvent or mixtures thereof. In another embodiment of step a), any physical form of vilazodone free base may be utilized, which may be anhydrous or hydrate, for providing the mixture of vilazodone free base in suitable solvent or mixtures thereof. The water content of hydrated vilazodone free base may vary from about 2.0% to about 10.0% w/w, more preferably from about 3.0% to about 8.0% w/w.

Vilazodone free base is mixed with a suitable solvent at any suitable temperature range, specifically at about 0° C. to about 50° C. and more specifically at about 25° C. to about 35° C. The mixture may optionally be cooled at about 0° C. to about −30° C., specifically at about −5° C. to about −20° C. and most specifically at about −10° C. to about −15° C.

Specifically, the suitable solvent includes but not limited to an alcoholic solvent, water and mixture thereof. The alcoholic solvent which includes, but not limited to $C_1$-$C_6$ branched or linear aliphatic alcohols such as methanol, ethanol, propanol, n-butanol, isopropanol, tert-butanol. More specifically, the solvent is methanol.

In one embodiment of step a), crystalline vilazodone hydrochloride is optionally added to the mixture of vilazodone free base and suitable solvent as a seed material. The crystalline vilazodone hydrochloride added as a seed material may be any crystalline form of vilazodone hydrochloride as known in the prior art. In an embodiment, the crystalline vilazodone hydrochloride added as a seed material may be form B of vilazodone hydrochloride which is obtained by a process as disclosed in this application. When the seed crystals are added, they are added in a quantity from about 0.1% w/w to about 50% w/w over the weight of free base. Specifically, the seed crystals are added in a quantity from about 0.5% to about 20% w/w and more specifically the seed crystals are added in a quantity from about 1% to about 10% w/w.

In embodiments of step b), mode of addition of step a) mixture with hydrochloric acid can be achieved by adding the hydrochloric acid solution in a suitable solvent to the mixture of step a) or reverse mode of addition can also be employed. The addition may be slow or at once while maintaining a temperature of about −30° C. to about 30° C. Specifically, the hydrochloric acid solution may be added slowly to the mixture of step a) at a temperature of about −20° C. to about −5° C. More specifically, the hydrochloric acid solution may be added slowly to the mixture of step a) at a temperature of about −10° C. to about −15° C. After complete addition, the mixture is stirred for about 30 minutes to about 30 hours at the same temperature. Specifically, the mixture is stirred for about 45 minutes to about 4 hours at the same temperature and more specifically the mixture is stirred for about 1 hour to about 3 hours at the same temperature.

The strength of hydrochloric acid solution in a suitable solvent is from about 3% w/w to about 30% w/w. Specifically, the strength of hydrochloric acid solution in a suitable solvent is from about 5% w/w to about 20% w/w. Hydrochloric acid solution in a suitable solvent can be prepared by purging of dry hydrogen chloride gas in a suitable solvent or mixtures thereof by the methods known in the prior art or by mixing the hydrochloric acid with suitable solvent or mixtures thereof. The suitable solvent includes but not limited to alcoholic solvent, water and mixture thereof. The alcoholic solvent includes but not limited to $C_1$-$C_6$ branched or linear aliphatic alcohols such as methanol, ethanol, propanol, n-butanol, isopropanol, tert-butanol. Specifically, the solvent is methanol. The hydrochloric acid solution in a suitable solvent may contain water. Water, if present, may vary from about 0.5% to 10.0% w/w, more specifically from about 1.0% to about 5.0% w/w.

In embodiments of step c), isolating crystalline form G of vilazodone hydrochloride may optionally involve one or more methods known in the art including removal of solvent by techniques known in the art e.g. evaporation, distillation, filtration of isolated solid and the like. Suitable temperatures for isolation may be less than about 25° C., less than about 10° C., or any other suitable temperatures. Filtration can be achieved by any means known in the art. Specifically, filtration can be achieved by using Buchner funnel or pressure nutsch filter (PNF) or jacketed agitated nutsch filter drier (ANFD). While using jacketed ANFD equipment, the temperature of jacket may be maintained at about −20° C. to about 5° C. by circulating brine solution. After the filtration, the wet solid is washed with cold alcoholic solvent and suck-dried for sufficient time. In case of filtration by PNF, the suck-drying is achieved by applying a positive pressure of dry air or nitrogen. In case of filtration by jacketed ANFD, the suck-drying is achieved by applying vacuum while maintaining the atmospheric pressure by supplying dry air or nitrogen. In case of filtration by Buchner funnel, the suck-drying is achieved by applying a vacuum. Specifically, the solid is washed with cold methanol and suck-dried for about 5 minutes to about 3 hours. In an embodiment, the filtration of solid may be achieved using ANFD.

The solid obtained from step c) may be collected using techniques such as by scraping, or by shaking the container, or other techniques specific to the equipment used.

The thirty first aspect of the present application relates to a pharmaceutically acceptable dosage form comprising crystalline form G of vilazodone hydrochloride and one or more pharmaceutically acceptable excipients.

In an embodiment, the present application relates to a process for conversion of form G of vilazodone hydrochloride to any other crystalline form of vilazodone hydrochloride by any process known in the art.

The thirty second aspect of the present application relates to conversion of crystalline form G of vilazodone hydrochloride to crystalline form B of vilazodone hydrochloride by suitable technique. More specifically, form G of vilazodone hydrochloride may be converted to form B of vilazodone hydrochloride by a suitable humidification process. Form G of vilazodone hydrochloride may be humidified with humid air of relative humidity of about 10% to about 95% for about 30 minutes to about 2 days. Specifically, form G of vilazodone hydrochloride is humidified with humid air of relative humidity of about 30% to about 70% for about 1 hour to about 40 hours to provide form B of vilazodone hydrochloride.

The thirty third aspect of the present application relates to crystalline form H of vilazodone hydrochloride characterized by its powder X-ray diffraction (PXRD) pattern having peaks at about 19.72, 20.92, 25.25 and 26.26±0.2 degrees 2θ. In embodiments, the present application relates to crystalline form H of vilazodone hydrochloride characterized by its PXRD pattern having additional peaks located at about 8.45, 12.46, 18.54 and 19.18±0.2 degrees 2θ. Still in other embodiments, the present application relates to crystalline form H of vilazodone hydrochloride characterized by its PXRD pattern having additional peaks located at about 13.08 and 16.25±0.2 degrees 2θ.

Figure 14:
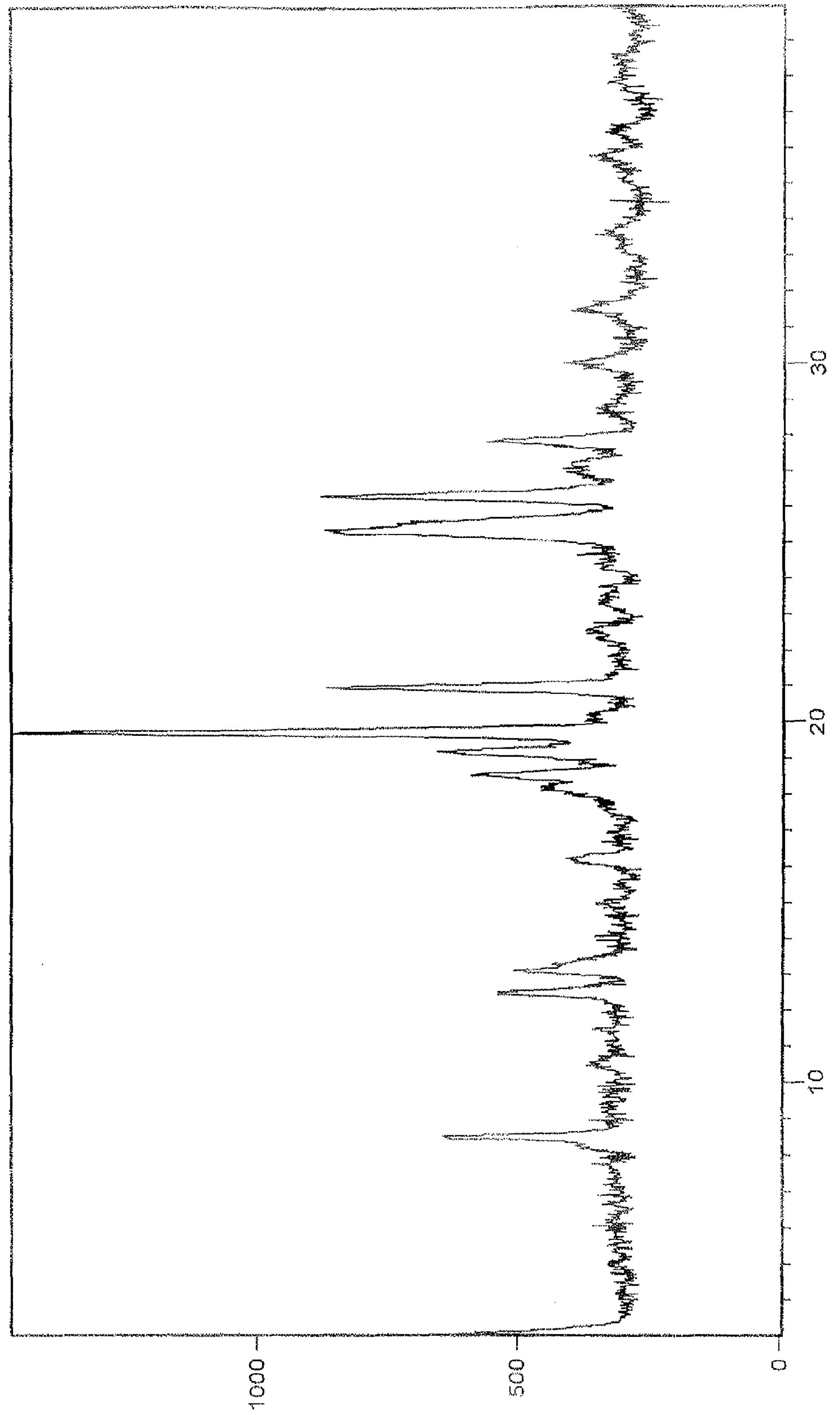
FIG. 14 is an illustration of a PXRD pattern of crystalline form H of vilazodone hydrochloride.

The thirty fourth aspect of the present application relates to crystalline form H of vilazodone hydrochloride that can be characterized by a PXRD pattern having peaks located substantially as illustrated in the pattern of FIG. 14.

Figure 15:
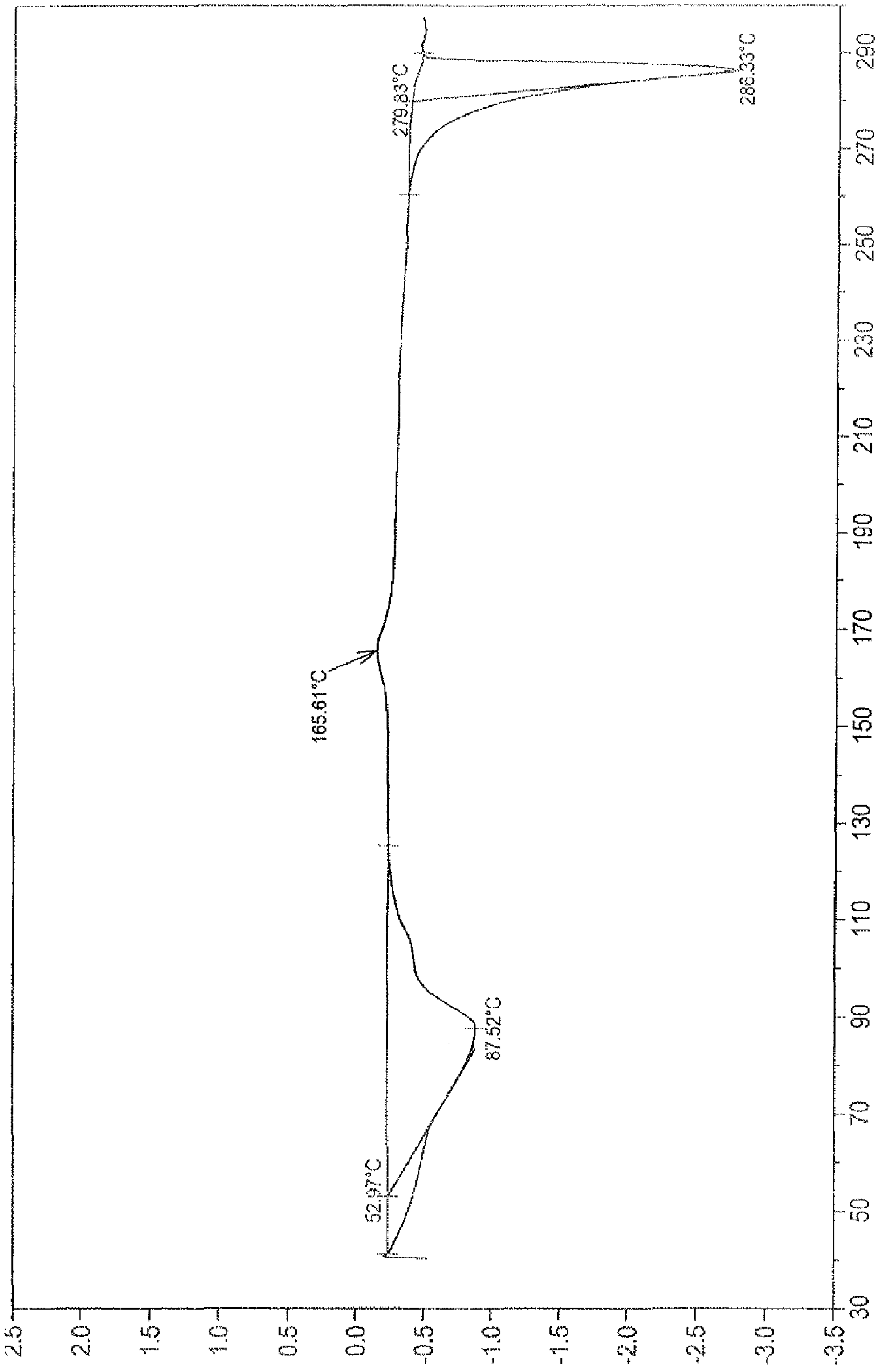
FIG. 15 is an illustration of a DSC thermogram of crystalline form H of vilazodone hydrochloride.

The thirty fifth aspect of the present application relates to crystalline form H of vilazodone hydrochloride that can be characterized by a DSC thermogram substantially as illustrated in the pattern of FIG. 15.

Figure 16:
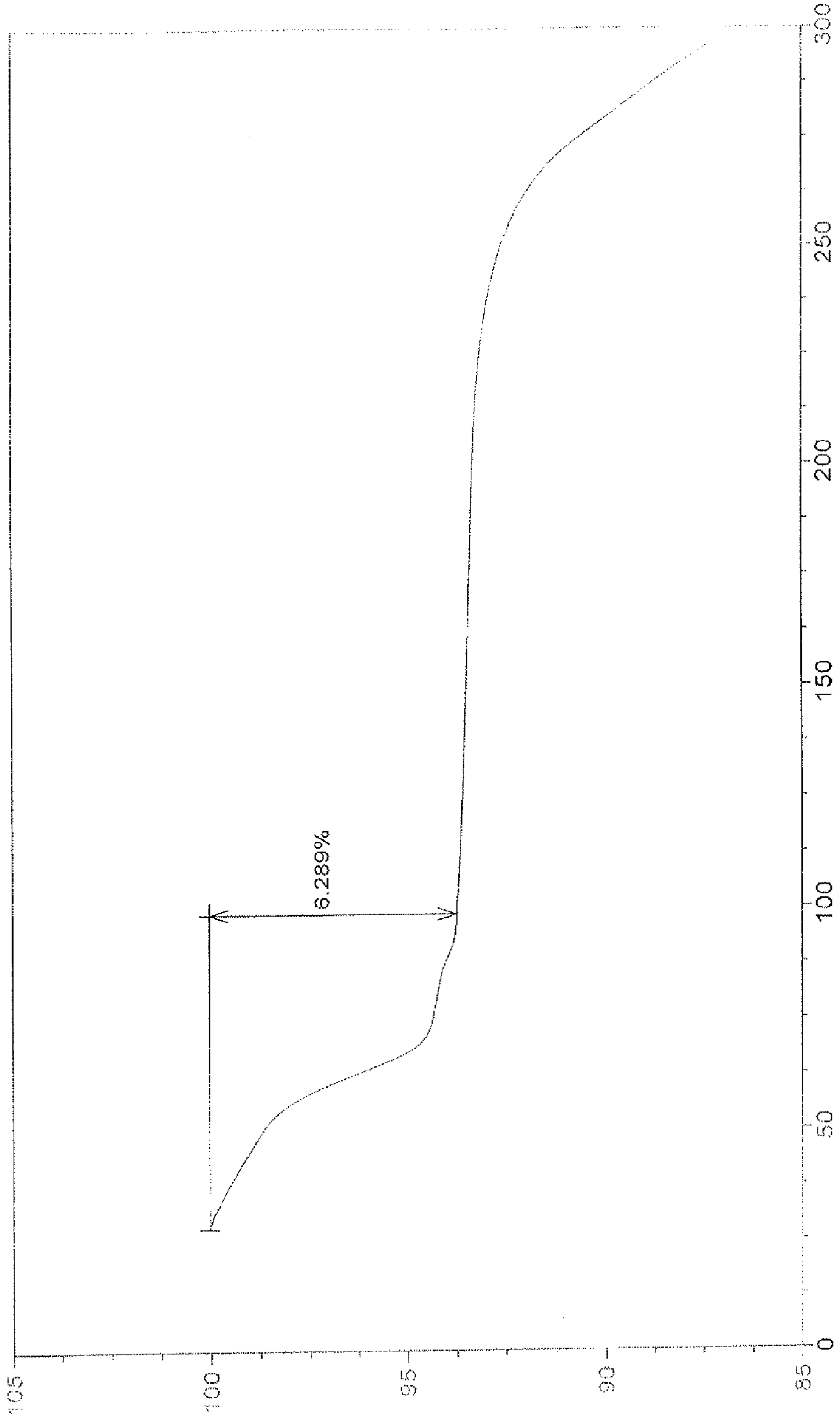
FIG. 16 is an illustration of a TGA thermogram of crystalline form H of vilazodone hydrochloride.

The thirty sixth aspect of the present application relates to crystalline form H of vilazodone hydrochloride that can be characterized by a TGA thermogram substantially as illustrated in the pattern of FIG. 16.

In another aspect, the crystalline form H of vilazodone hydrochloride contains methanol less than about 2000 ppm. Specifically, the crystalline form H of vilazodone hydrochloride contains methanol less than about 1500 ppm and more specifically the crystalline form H of vilazodone hydrochloride contains methanol less than about 1000 ppm.

In yet another aspect, moisture content of form H of vilazodone hydrochloride is up to about 8.0% w/w. Specifically, the moisture content of form H of vilazodone hydrochloride is from about 5.5% to about 7.5% w/w and more specifically moisture content of form H of vilazodone hydrochloride is from about 6.0% to about 7.3% w/w.

The thirty seventh aspect of the present application relates to a process for preparing crystalline form H of vilazodone hydrochloride, which comprises:

a) providing a mixture of vilazodone free base in suitable solvent or mixtures thereof;
b) combining hydrochloric acid with the mixture of step a);
c) isolating crystalline vilazodone hydrochloride; and
d) stirring crystalline vilazodone hydrochloride as obtained in step c) in water; and
e) isolating crystalline form H of vilazodone hydrochloride.

In one of the embodiments of step a), any physical form of vilazodone free base may be utilized, which may be crystalline or amorphous, for providing the mixture of vilazodone free base in suitable solvent or mixtures thereof.

In another embodiment of step a), any physical form of vilazodone free base may be utilized, which may be anhydrous or hydrate, for providing the mixture of vilazodone free base in suitable solvent or mixtures thereof. The water content of hydrated vilazodone free base may vary from about 2.0% to about 10.0% w/w, more preferably from about 3.0% to about 8.0% w/w.

Vilazodone free base is mixed with a suitable solvent at any suitable temperature range, specifically at about 0° C. to about 50° C. and more specifically at about 25° C. to about 35° C. The mixture may optionally be cooled at about 0° C. to about −30° C., specifically at about −5° C. to about −20° C. and most specifically at about −10° C. to about −15° C.

Specifically, the suitable solvent includes but not limited to an alcoholic solvent, water and mixture thereof. The alcoholic solvent which includes, but not limited to $C_1$-$C_6$ branched or linear aliphatic alcohols such as methanol, ethanol, propanol, n-butanol, isopropanol, tert-butanol. More specifically, the solvent is methanol.

In one embodiment of step a), the seed crystals of form B of vilazodone hydrochloride is optionally added to the mixture of vilazodone free base and suitable solvent. The crystalline form B of vilazodone hydrochloride is obtained by a process as disclosed in this application. When the seed crystals are added, they are added in a quantity from about 0.1% w/w to about 50% w/w over the weight of free base. Specifically, the seed crystals are added in a quantity from about 0.5% to about 20% w/w and more specifically the seed crystals are added in a quantity from about 1% to about 10% w/w.

In embodiments of step b), mode of addition of step a) mixture with hydrochloric acid can be achieved by adding the hydrochloric acid solution in a suitable solvent to the mixture of step a) or reverse mode of addition can also be employed. The addition may be slow or at once while maintaining a temperature of about −30° C. to about 30° C. After complete addition, the mixture is stirred for about 30 minutes to about 30 hours at the same temperature. Specifically, the mixture is stirred for about 1 hour to about 15 hours at the same temperature.

The strength of hydrochloric acid solution in a suitable solvent is from about 3% w/w to about 30% w/w. Specifically, the strength of hydrochloric acid solution in a suitable solvent is from about 5% w/w to about 20% w/w. Hydrochloric acid solution in a suitable solvent can be prepared by purging of dry hydrogen chloride gas in a suitable solvent or mixtures thereof by the methods known in the prior art or by mixing the hydrochloric acid with suitable solvent or mixtures thereof. The suitable solvent includes but not limited to alcoholic solvent, water and mixture thereof. The alcoholic solvent includes but not limited to $C_1$-$C_6$ branched or linear aliphatic alcohols such as methanol, ethanol, propanol, n-butanol, isopropanol, tert-butanol. Specifically, the solvent is methanol. The hydrochloric acid solution in a suitable solvent may contain water. Water, if present, may vary from about 0.5% to 10.0% w/w, more specifically from about 1.0% to about 5.0% w/w.

In embodiments of step c), isolating crystalline form of vilazodone hydrochloride may optionally involve one or more methods known in the art including removal of solvent by techniques known in the art e.g. evaporation, distillation, filtration of isolated solid and the like. Specifically, crystalline form of vilazodone hydrochloride of step c) may be isolated by filtration. Filtration can be achieved by any means known in the art. Suitable temperatures for isolation may be less than about 25° C., less than about 10° C., or any other suitable temperatures. The crystalline form of vilazodone hydrochloride isolated in step c) may be any crystalline form known in the art. In one embodiment, the crystalline form of vilazodone hydrochloride isolated in step c) is form B of vilazodone hydrochloride.

The crystalline form of vilazodone hydrochloride, isolated in step c) is optionally dried for about 30 minutes to about 5 hours and specifically for about 1 hour to about 2 hours. Drying may suitably be carried out in an air oven, using a fluidized bed drier, spin flash dryer, flash dryer and the like, and drying equipment selection is well within the scope of a person having ordinary skill in the art and it is also within the scope of the present application.

The crystalline form of vilazodone hydrochloride, isolated in step c) is stirred in water for suitable time until the reaction mass shows complete conversion to form H of vilazodone hydrochloride. Specifically, the crystalline form of vilazodone hydrochloride, isolated in step c) is stirred in water from about 10 hours to 15 days. More specifically, the crystalline form of vilazodone hydrochloride, isolated in step c) is stirred in water from about 15 hours to 12 days.

In embodiments of step e), isolating crystalline form H of vilazodone hydrochloride may optionally involve one or more methods known in the art including removal of solvent by techniques known in the art e.g. evaporation, distillation, filtration of isolated solid and the like. Specifically, crystalline form H of vilazodone hydrochloride may be isolated by filtration. Filtration can be achieved by any means known in the art. Suitable temperatures for isolation may be less than about 25° C., less than about 10° C., or any other suitable temperatures.

The crystalline form H of vilazodone hydrochloride, isolated in step e) is optionally dried for about 30 minutes to about 30 hours; specifically for about 45 minutes to about 5 hours and more specifically from about 1 hour to about 2 hours. Drying may suitably be carried out in an air oven, using a fluidized bed drier, spin flash dryer, flash dryer and the like, and drying equipment selection is well within the scope of a person having ordinary skill in the art and it is also within the scope of the present application.

The DSC thermogram of form H of vilazodone hydrochloride of the present application shows a dehydration process between about 30° C. and about 100° C. The DSC measurement gives a phase transition between about 130° C. and about 190° C.

The thirty eighth aspect of the present application relates to a pharmaceutically acceptable dosage form comprising crystalline form H of vilazodone hydrochloride and one or more pharmaceutically acceptable excipients.

The thirty ninth aspect of the present application relates to amorphous solid dispersion of vilazodone hydrochloride with a pharmaceutically acceptable carrier.

In embodiments, the present application provides amorphous solid dispersion of vilazodone hydrochloride with a polyvinylpyrrolidone (PVP). Still in other embodiments, the present application provides amorphous solid dispersion of vilazodone hydrochloride with hydroxypropyl methylcellulose (HPMC).

The ratio of vilazodone hydrochloride with a pharmaceutically acceptable carrier in amorphous solid dispersion can be about 5:95 and 95:5, or between about 10:90 and 90:10, or between about 25:75 and 75:25, by weight, including, but not limited to, about 5% w/w to about 95% w/w, or about 20% w/w to about 80% w/w, or about 70% w/w to about 30% w/w, or about 50% w/w to about 50% w/w, or about 95% w/w to about 5% w/w, or about 75% w/w to about 25% w/w, or about 60% w/w to about 40% w/w.

Figure 12:
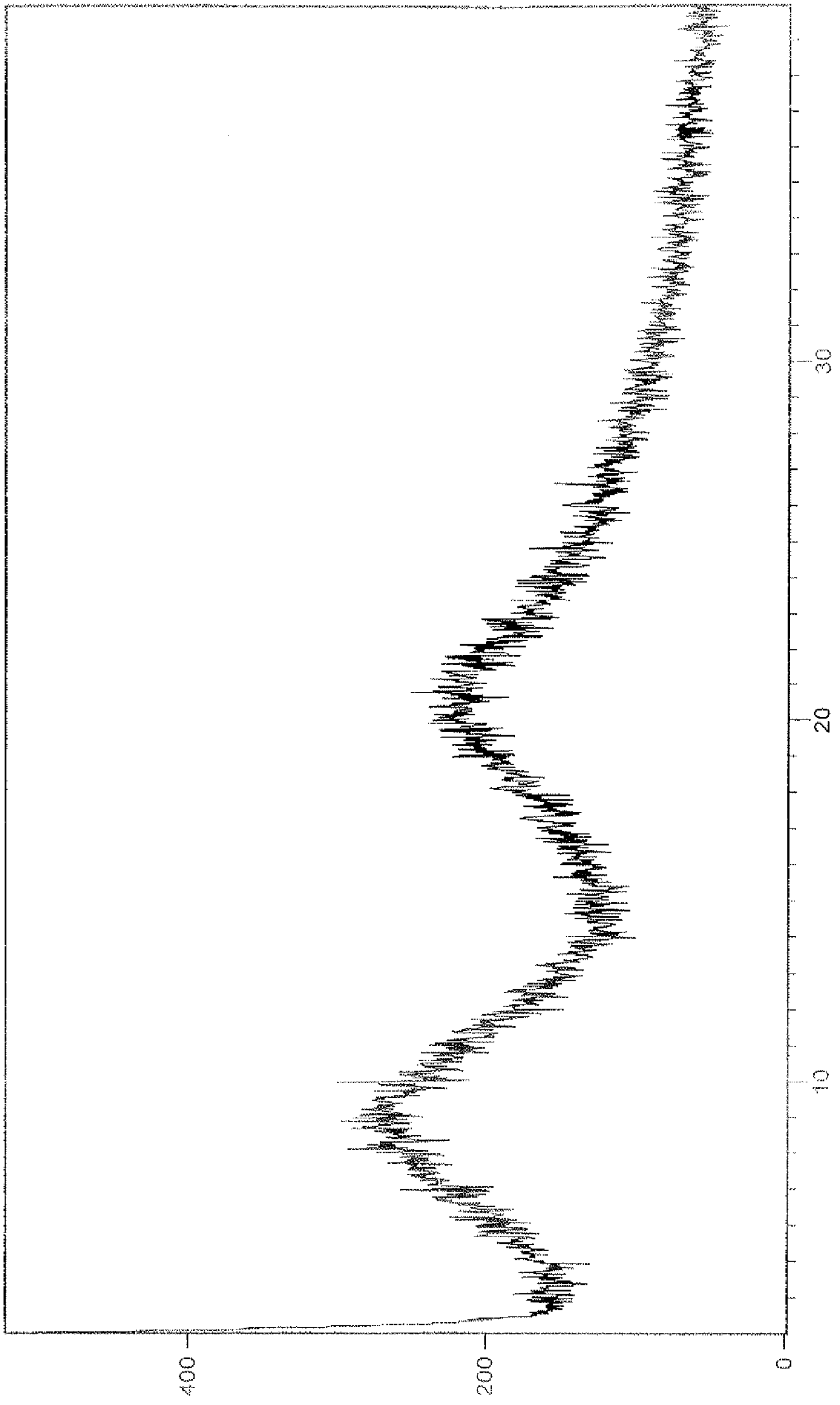
FIG. 12 is an illustration of a PXRD pattern of amorphous solid dispersion of vilazodone hydrochloride with a pharmaceutically acceptable carrier such as polyvinylpyrrolidone (PVP) or hydroxypropyl methylcellulose (HPMC).

The fortieth aspect of the present application relates to amorphous solid dispersion of vilazodone hydrochloride with a pharmaceutically acceptable carrier such as polyvinylpyrrolidone (PVP) or hydroxypropyl methylcellulose (HPMC) that can be characterized by a PXRD pattern substantially as illustrated in the pattern of FIG. 12.

The forty first aspect of the present application relates to process for preparing amorphous solid dispersion of vilazodone hydrochloride with a pharmaceutically acceptable carrier, which comprises:

a) providing a mixture of vilazodone hydrochloride and pharmaceutically acceptable carrier in suitable solvent or mixtures thereof;

b) heating the mixture to obtain a clear solution; and c) isolating amorphous solid dispersion of vilazodone hydrochloride with a pharmaceutically acceptable carrier.

In the present application, vilazodone hydrochloride which is used as a starting material for preparing the amorphous solid dispersion may be prepared using methods known in the prior art. Alternatively, crystalline form B or crystalline form C or crystalline form G or crystalline form H or mixtures thereof of the present application can also be used for preparing amorphous solid dispersion.

In embodiments of step a), providing a mixture of vilazodone hydrochloride may include:

i) direct use of a reaction mixture containing vilazodone hydrochloride that is obtained in the course of its synthesis and that comprises one of the suitable solvents or mixtures thereof, or by combining one of the suitable solvents or mixtures thereof and a pharmaceutically acceptable carrier with the reaction mixture; or ii) mixing the vilazodone hydrochloride and a pharmaceutical acceptable carrier in one of the suitable solvents or mixtures thereof.

In embodiments of step a) and step b), any physical form of vilazodone hydrochloride may be utilized for providing the mixture of vilazodone hydrochloride and a pharmaceutically acceptable carrier in suitable solvent or mixtures thereof. The mixture is further heated to afford clear solution. The dissolution temperatures may range from about ambient temperature to about the reflux temperature of the solvent, or less than about 120° C., less than about 100° C., less than about 80° C., or any other suitable temperatures, as long as a clear solution is obtained without affecting the quality. The solution may optionally be treated with carbon, flux-calcined diatomaceous earth (e.g., Hyflow™), or any other suitable material to remove color, insoluble materials, improve clarity of the solution, and/or remove impurities that are adsorbable on such material. Optionally, the solution obtained may be treated to remove any insoluble particles. The insoluble particles may be removed suitably by filtration, centrifugation, decantation, or any other suitable techniques under pressure or under reduced pressure. A solution may be filtered by passing through paper, glass fiber, cloth or other membrane material, or a bed of a clarifying agent such as Celite® or Hyflow. Depending upon the concentration and temperature of the solution and the equipment used, the filtration apparatus may optionally be preheated to avoid premature crystallization.

The pharmaceutically acceptable carriers which may be used include, but are not limited to pharmaceutical hydrophilic carriers such as polyvinylpyrrolidone (homopolymers, also called "povidone," or copolymers of N-vinylpyrrolidone), gums, cellulose derivatives (including hydroxypropyl methylcellulose, hydroxypropyl cellulose and others), cyclodextrins, gelatins, hypromellose phthalate, sugars, polyhydric alcohols. The use of mixtures of more than one of the pharmaceutical carriers to provide desired release profiles or for the enhancement of stability is within the scope of this application. Also, all viscosity grades, molecular weights, commercially available products, their copolymers, mixtures are all within the scope of this application without limitation.

These lists of solvents and pharmaceutically acceptable carriers are merely representative of those that can be used, and the lists are not intended to be exhaustive or limiting. Generally, the more volatile solvents are preferred to reduce the energy requirements for subsequent solvent removal.

In embodiments of step c), isolating amorphous solid dispersion of vilazodone hydrochloride may optionally involve one or more methods including removal of solvent by techniques known in the art e.g. evaporation, distillation, filtration of precipitated solid and the like cooling; concentrating the mass; adding seed crystals to induce crystallization; and the like. Stirring or other alternate methods such as shaking, agitation, and the like, may also be employed for the isolation. Distillation of the solvent may be conducted at atmospheric pressure or above, or under reduced pressures and at a temperatures less than about 120° C., less than about 100° C., less than about 90° C., or any other suitable temperatures. Any temperature and vacuum conditions can be used as long as there is no increase in the impurity levels of the product due to decomposition, etc.

Suitable techniques which can be used for the distillation include, without limitation thereto, distillation using a rotational evaporator device such as a Buchi Rotavapor, spray drying, agitated thin film drying ("ATFD"), and the like.

Generally, techniques providing a rapid solvent removal can be utilized to provide the desired amorphous solid dispersion of vilazodone hydrochloride.

The solid obtained from step c) may be collected using techniques such as by scraping, or by shaking the container, or other techniques specific to the equipment used. The isolated solid may be optionally further dried to afford amorphous solid dispersion of vilazodone hydrochloride.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, at temperatures less than about 120° C., less than about 100° C., less than about 80° C., or any other suitable temperatures. The drying may be carried out for any time period required for obtaining a desired product quality, such as from about 5 minutes to about 24 hours, or longer.

The obtained amorphous solid dispersions may optionally be subjected to a particle size reduction procedure to produce desired particle sizes and distributions. Milling or micronization may be performed before drying, or after the completion of drying of the amorphous solid dispersions. Equipment that may be used for particle size reduction include, without limitation thereto, ball, roller, and hammer mills, and jet mills.

The forty second aspect of the present application relates to a pharmaceutically acceptable dosage form comprising amorphous solid dispersion of vilazodone hydrochloride and one or more pharmaceutically acceptable excipients.

The forty third aspect of the present application relates to amorphous solid dispersion of vilazodone hydrochloride with a polyvinylpyrrolidone (PVP).

The forty fourth aspect of the present application relates to process for preparing amorphous solid dispersion of vilazodone hydrochloride with polyvinylpyrrolidone (PVP), which comprises:

a) providing a mixture of vilazodone hydrochloride and polyvinylpyrrolidone (PVP) in suitable solvent or mixtures thereof;
b) heating the mixture to obtain a clear solution; and
c) isolating amorphous solid dispersion of vilazodone hydrochloride with polyvinylpyrrolidone (PVP).

The forty fifth aspect of the present application relates to a pharmaceutically acceptable dosage form comprising amorphous solid dispersion of vilazodone hydrochloride with PVP and one or more pharmaceutically acceptable excipients.

The forty sixth aspect of the present application relates to amorphous solid dispersion of vilazodone hydrochloride with hydroxypropyl methylcellulose (HPMC).

The forty seventh aspect of the present application relates to process for preparing amorphous solid dispersion of vilazodone hydrochloride with hydroxypropyl methylcellulose (HPMC), which comprises:
a) providing a mixture of vilazodone hydrochloride and hydroxypropyl methylcellulose (HPMC) in suitable solvent or mixtures thereof;
b) heating the mixture to obtain a clear solution; and
c) isolating amorphous solid dispersion of vilazodone hydrochloride with hydroxypropyl methylcellulose (HPMC).

The forty eighth aspect of the present application relates to a pharmaceutically acceptable dosage form comprising amorphous solid dispersion of vilazodone hydrochloride with HPMC and one or more pharmaceutically acceptable excipients.

The forty ninth aspect of the present application relates to pure amorphous form of vilazodone hydrochloride.

Figure 20:
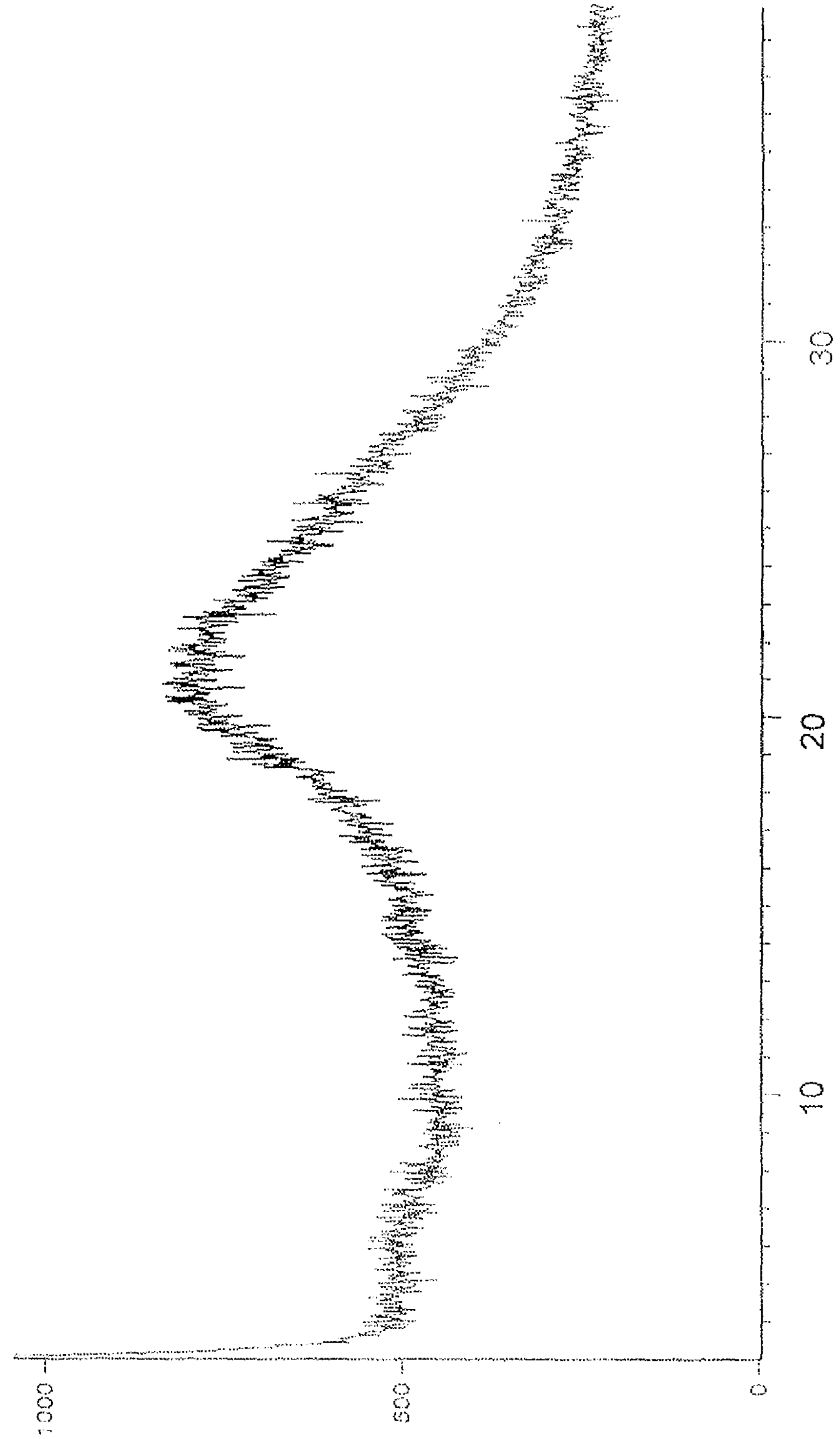
FIG. 20 is an illustration of a PXRD pattern of amorphous form of vilazodone hydrochloride.

The fiftieth aspect of the present application relates to pure amorphous form of vilazodone hydrochloride which may be characterized by a PXRD pattern substantially as illustrated in FIG. 20.

The pure amorphous form of vilazodone hydrochloride of the present application may contain water. The water content of pure amorphous form of vilazodone hydrochloride may vary from about 4.0% w/w to about 8.0% w/w. Specifically, the water content of pure amorphous form of vilazodone hydrochloride may vary from about 5.0% w/w to 7.0% w/w and more specifically the water content of pure amorphous form of vilazodone hydrochloride may vary from about 5.2% w/w to 6.0% w/w.

It is surprisingly found that the said variation of water in pure amorphous form of vilazodone hydrochloride does not affect the stability and PXRD pattern of pure amorphous form which is in accordance with FIG. 20.

The fifty first aspect of the present application relates to process for preparing pure amorphous form of vilazodone hydrochloride comprising:
a) subjecting known crystalline form of vilazodone hydrochloride to ball milling; and
b) isolating pure amorphous form of vilazodone hydrochloride.

Any known crystalline form of vilazodone hydrochloride or mixture thereof may be used as starting material for preparing pure amorphous form of vilazodone hydrochloride. Specifically, pure amorphous form of vilazodone hydrochloride may be prepared in accordance to the present application from a crystalline form III or IV or V or VI or VII or VIII or IX or B or C or D or E or F or G or H of vilazodone hydrochloride. Specifically, pure amorphous form of vilazodone hydrochloride may be prepared from a crystalline form IV or B or C of vilazodone hydrochloride. More specifically, pure amorphous form of vilazodone hydrochloride may be prepared from a crystalline form B or C of vilazodone hydrochloride. Crystalline forms of vilazodone hydrochloride may be prepared by processes known in the prior references or by the process disclosed in this application.

A crystalline form of vilazodone hydrochloride is charged into a ball-milling vessel and milled for about 30 minutes to about 10 hour at about 50 rpm to about 500 rpm. Specifically, a crystalline form of vilazodone hydrochloride is subjected to ball-milling for about 1 hour to about 5 hours at about 200 rpm to about 400 rpm. More specifically, a crystalline form of vilazodone hydrochloride is subjected to ball-milling for about 2 hours to about 4 hours at about 250 rpm to about 350 rpm.

The resulting solid may be collected using techniques such as by scraping, or by shaking the container, or other techniques specific to the equipment used. The isolated solid may be optionally further dried to afford pure amorphous form of vilazodone hydrochloride.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 5 minutes to about 24 hours, or longer.

The dried product may optionally be subjected to a particle size reduction procedure to produce desired particle sizes and distributions. Milling or micronization may be performed before drying, or after the completion of drying of the product. Equipment that may be used for particle size reduction includes but not limited to ball mill, roller mill, hammer mill, and jet mill.

The fifty second aspect of the present application relates to process for preparing pure amorphous form of vilazodone hydrochloride comprising:
a) dissolving crystalline vilazodone hydrochloride in a suitable solvent or mixture thereof;
b) optionally filtering the undissolved particles;
c) removing the solvent from the filtrate of step b) by any suitable technique; and
d) drying the product at suitable temperature.

Any known crystalline form of vilazodone hydrochloride or mixture thereof may be used as starting material for preparing pure amorphous form of vilazodone hydrochloride. Specifically, pure amorphous form of vilazodone hydrochloride may be prepared in accordance to the present application from a crystalline form III or IV or V or VI or VII or VIII or IX or B or C or D or E or F or G or H of vilazodone hydrochloride. Specifically, pure amorphous form of vilazodone hydrochloride may be prepared from a crystalline form IV or B or C of vilazodone hydrochloride. More specifically, pure amorphous form of vilazodone hydrochloride may be prepared from a crystalline form B or C of vilazodone hydrochloride. Crystalline forms of vilazodone hydrochloride may be prepared by processes known in the prior references or by the process disclosed in this application.

Suitable solvents for dissolving vilazodone hydrochloride include, but are not limited to dimethylformamide; dimethylacetamide; dimethyl sulphoxide; ketones such as acetone, ethyl methyl ketone, 2-butanone, methyl isobutyl ketone; ethers such as tetrahydrofuran, dioxane; esters such as ethyl acetate, isopropyl acetate; nitriles such as acetonitrile, propionitrile; hydrocarbons such as toluene, xylene, hexane, heptane; halogenated hydrocarbons such as dichloromethane; alcohols such as methanol, ethanol, propanol, isopropanol; water; or mixtures thereof. Specifically, the solvent is selected from a group of dimethylformamide; dimethylacetamide; dimethyl sulphoxide; alcohols such as methanol, ethanol, propanol, isopropanol; water; and mixtures thereof. More specifically, the solvent is selected from a group of dimethylformamide; methanol; ethanol; isopropanol; tert-butanol; water and mixture thereof. Most specifically, the solvent is selected from a group of dimethylformamide; methanol; water and mixture thereof.

Suitable techniques that may be used for the removal of solvent include but are not limited to rotational distillation using a device such as Buchi Rotavapor, spray drying, agitated thin film drying ("ATFD"), freeze drying (lyophilization) and the like, optionally under reduced pressure. It has been surprisingly found that when a solution comprising vilazodone hydrochloride is subjected to spray-drying or freeze-drying technique, pure amorphous form of vilazodone hydrochloride is obtained.

The resulting solid may be collected using techniques such as by scraping, or by shaking the container, or other techniques specific to the equipment used. The isolated solid may be optionally further dried to afford pure amorphous form of vilazodone hydrochloride.

Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 5 minutes to about 24 hours, or longer.

The dried product may optionally be subjected to a particle size reduction procedure to produce desired particle sizes and distributions. Milling or micronization may be performed before drying, or after the completion of drying of the product. Equipment that may be used for particle size reduction includes but not limited to ball mill, roller mill, hammer mill, and jet mill.

The amorphous vilazodone hydrochloride that is substantially free of any crystalline form is hereby referred to as 'pure amorphous' vilazodone hydrochloride. Pure amorphous form of vilazodone hydrochloride does not contain more than about 10% of any crystalline form of vilazodone hydrochloride. Specifically, pure amorphous vilazodone hydrochloride does not contain more than about 5% of any crystalline form of vilazodone hydrochloride. More specifically, pure amorphous vilazodone hydrochloride does not contain more than about 3% of any crystalline form of vilazodone hydrochloride. Most specifically, pure amorphous vilazodone hydrochloride does not contain more than about 1% of any crystalline form of vilazodone hydrochloride. FIG. 20 illustrates an XRPD pattern of pure amorphous form of vilazodone hydrochloride obtained by a process of example 10b.

The fifty third aspect of the present application relates to a pharmaceutically acceptable dosage form comprising pure amorphous vilazodone hydrochloride and one or more pharmaceutically acceptable excipients.

The fifty fourth aspect of the present application relates to a process for preparing vilazodone free base comprising the condensation of 5-(piperazin-1-yl)benzofuran-2-carboxamide with 3-(4-chlorobutyl)-1H-indole-5-carbonitrile in a suitable solvent in presence of a base and an additive selected from a group of an ionic additive, a phase transfer catalyst and mixture thereof.

Suitable solvents for the condensation reaction include, but not limited to dimethylformamide; dimethylacetamide; dimethyl sulphoxide; ketones such as acetone, ethyl methyl ketone, 2-butanone, methyl isobutyl ketone; ethers such as tetrahydrofuran, dioxane; esters such as ethyl acetate, isopropyl acetate; nitriles such as acetonitrile, propionitrile; hydrocarbons such as toluene, xylene; halogenated hydrocarbons such as dichloromethane; alcohols such as methanol, ethanol, propanol, isopropanol; water; mixtures thereof. Specifically, the solvent is selected from a group of dimethylformamide; dimethylacetamide; dimethyl sulphoxide; nitriles such as acetonitrile; water; and mixtures thereof. More specifically, the solvent is selected from a group of dimethylformamide; dimethyl sulphoxide; acetonitrile; water and mixture thereof. Most specifically, the solvent is selected from a group of dimethylformamide; water and mixture thereof.

Suitable base for the condensation reaction include, but not limited to diisopropylethylamine; diisopropylmethylamine; triethylamine; potassium salts such as potassium carbonate, potassium bicarbonate; sodium salts such as sodium carbonate, sodium bicarbonate; 1,4-diazabicyclo[2.2.2]octane (DABCO); 8-diazabicyclo[5.4.0]-undec-7-ene (DBU); pyridine. Specifically, the base is selected from a group of diisopropylethylamine; diisopropylmethylamine; triethylamine; sodium bicarbonate; sodium carbonate; potassium carbonate and potassium bicarbonate. More specifically, the base is selected from a group of diisopropylethylamine, sodium bicarbonate and sodium carbonate.

It has been observed that both reaction temperature and reaction time of the condensation reaction between 5-(piperazin-1-yl)benzofuran-2-carboxamide and 3-(4-chlorobutyl)-1H-indole-5-carbonitrile may be substantially minimized by the addition of an additive selected from a group of an ionic additive, a phase transfer catalyst and mixture thereof. Thus, addition of an additive makes the condensation reaction effective in terms of both energy and cost.

Ionic additive includes, but not limited to sodium salts such as sodium iodide, sodium sulfate, sodium chloride; potassium salts such as potassium iodide, potassium sulfate, potassium chloride; mixtures thereof. Specifically, the ionic additive is selected from a group of sodium iodide, sodium sulfate and potassium iodide. More specifically, the ionic additive is selected from a group of sodium iodide and sodium sulfate. Phase transfer catalyst includes, but not limited to tetrabutylammonium bromide, tetrabutylammonium iodide, tetrabutylammonium chloride, tetraethylammonium tetrafluoroborate, triphenylphosphonium chloride, benzyltrimethylammonium chloride and hexadecyltributylphosphonium bromide. Specifically, the phase transfer catalyst is selected from a group of tetrabutylammonium bromide, tetrabutylammonium iodide and tetrabutylammonium chloride. More specifically, the phase transfer catalyst is tetrabutylammonium bromide.

One embodiment of the present application relates to condensation reaction between 5-(piperazin-1-yl)benzofuran-2-carboxamide and 3-(4-chlorobutyl)-1H-indole-5-carbonitrile in DMF in presence of a base and an ionic additive at a temperature of about 50° C. to about 150° C. for a period of about 30 minutes to about 5 hours. Specifically, the condensation reaction between 5-(piperazin-1-yl) benzofuran-2-carboxamide and 3-(4-chlorobutyl)-1H-indole-5-carbonitrile in DMF in presence of sodium bicarbonate and sodium iodide at a temperature of about 80°

C. to about 130° C. for a period of about 45 minutes to about 3 hours. More specifically, the condensation reaction between 5-(piperazin-1-yl)benzofuran-2-carboxamide and 3-(4-chlorobutyl)-1H-indole-5-carbonitrile in DMF in presence of sodium bicarbonate and sodium iodide at a temperature of about 110° C. to about 115° C. for a period of about 1 hour to about 2 hours.

Another embodiment of the present application relates to condensation reaction between 5-(piperazin-1-yl)benzofuran-2-carboxamide and 3-(4-chlorobutyl)-1H-indole-5-carbonitrile in DMF in presence of a base, an ionic additive and a phase transfer catalyst at a temperature of about 50° C. to about 150° C. for a period of about 30 minutes to about 5 hours. Specifically, the condensation reaction between 5-(piperazin-1-yl)benzofuran-2-carboxamide and 3-(4-chlorobutyl)-1H-indole-5-carbonitrile in DMF in presence of sodium bicarbonate, sodium iodide and tetrabutylaamonium bromide at a temperature of about 70° C. to about 130° C. for a period of about 45 minutes to about 3 hours. More specifically, the condensation reaction between 5-(piperazin-1-yl)benzofuran-2-carboxamide and 3-(4-chlorobutyl)-1H-indole-5-carbonitrile in DMF in presence of sodium bicarbonate, sodium iodide and tetrabutylaamonium bromide at a temperature of about 100° C. to about 120° C. for a period of about 1 hour to about 2 hours.

Yet another embodiment of the present application relates to condensation reaction between 5-(piperazin-1-yl)benzofuran-2-carboxamide and 3-(4-chlorobutyl)-1H-indole-5-carbonitrile in DMF in presence of a base and a phase transfer catalyst at a temperature of about 50° C. to about 150° C. for a period of about 1 hour to about 6 hours. Specifically, the condensation reaction between 5-(piperazin-1-yl)benzofuran-2-carboxamide and 3-(4-chlorobutyl)-1H-indole-5-carbonitrile in DMF in presence of sodium bicarbonate and tetrabutylammonium bromide at a temperature of about 80° C. to about 130° C. for a period of about 2 hours to about 5 hours. More specifically, the condensation reaction between 5-(piperazin-1-yl)benzofuran-2-carboxamide and 3-(4-chlorobutyl)-1H-indole-5-carbonitrile in DMF in presence of sodium bicarbonate and tetrabutylammonium bromide at a temperature of about 110° C. to about 120° C. for a period of about 4 hours.

Still another embodiment of the present application relates to condensation reaction between 5-(piperazin-1-yl)benzofuran-2-carboxamide and 3-(4-chlorobutyl)-1H-indole-5-carbonitrile in water in presence of a base and an ionic additive at a temperature of about 50° C. to about 150° C. for a period of about 5 hour to about 12 hours. Specifically, the condensation reaction between 5-(piperazin-1-yl)benzofuran-2-carboxamide and 3-(4-chlorobutyl)-1H-indole-5-carbonitrile in water in presence of sodium bicarbonate and sodium sulfate at a temperature of about 70° C. to about 120° C. for a period of about 6 hours to about 11 hours. More specifically, the condensation reaction between 5-(piperazin-1-yl)benzofuran-2-carboxamide and 3-(4-chlorobutyl)-1H-indole-5-carbonitrile in water in presence of sodium bicarbonate and sodium sulfate at a temperature of about 90° C. to about 100° C. for a period of about 9 hours to about 10 hours.

Another embodiment of the present application relates to condensation reaction between 5-(piperazin-1-yl)benzofuran-2-carboxamide and 3-(4-chlorobutyl)-1H-indole-5-carbonitrile in water in presence of a base and an ionic additive at a temperature of about 50° C. to about 150° C. for a period of about 6 hours to about 14 hours. Specifically, the condensation reaction between 5-(piperazin-1-yl)benzofuran-2-carboxamide and 3-(4-chlorobutyl)-1H-indole-5-carbonitrile in water in presence of sodium carbonate and sodium iodide at a temperature of about 70° C. to about 120° C. for a period of about 8 hours to about 12 hours. More specifically, the condensation reaction between 5-(piperazin-1-yl)benzofuran-2-carboxamide and 3-(4-chlorobutyl)-1H-indole-5-carbonitrile in water in presence of sodium carbonate and sodium iodide at a temperature of about 80° C. to about 90° C. for a period of about 10 hours to about 11 hours.

Isolation and purification of the vilazodone free base prepared by a method described above can be effected by any suitable separation or purification procedure such as, filtration, centrifugation, extraction, acid-base treatment, crystallization, conventional isolation and refining means such as concentration, concentration under reduced pressure, solvent-extraction, crystallization, phase-transfer chromatography, column chromatography, or by a combination of these procedures. Specifically, vilazodone free base is isolated by filtration technique and dried. Drying may be suitably carried out using any of an air tray dryer, vacuum tray dryer, fluidized bed dryer, spin flash dryer, flash dryer, and the like. The drying may be carried out at atmospheric pressure or above, or under reduced pressures, specifically at temperatures less than about 80° C. and more specifically less than about 60° C. The drying may be carried out for any time period required for obtaining a desired product quality, such as from about 5 minutes to about 24 hours, or longer.

The dried product may optionally be subjected to a particle size reduction procedure to produce desired particle sizes and distributions. Milling or micronization may be performed before drying, or after the completion of drying of the product. Equipment that may be used for particle size reduction includes but not limited to ball mill, roller mill, hammer mill, and jet mill.

The starting materials, 5-(piperazin-1-yl)benzofuran-2-carboxamide and 3-(4-chlorobutyl)-1H-indole-5-carbonitrile may be prepared by any known methodology as disclosed in prior art references. Alternatively, 3-(4-chlorobutyl)-1H-indole-5-carbonitrile may be prepared by a process as disclosed in the present application.

The fifty fifth aspect of the present application relates to a crystalline form of vilazodone free base (hereinafter designated as form I) which may be characterized by X-ray powder diffraction (PXRD) pattern having peaks at about 5.8, 18.6 and 20.8±0.2 degrees 2θ. The form I of vilazodone free base may be characterized by PXRD pattern substantially as illustrated in FIG. 21.

Form I of vilazodone free base of the present application may contain water. The water content of form I of vilazodone free base may vary from about 4.0% w/w to about 6.0% w/w. Specifically, the water content of crystalline form I of vilazodone free base may vary from about 4.5% w/w to 5.2% w/w and more specifically the water content of crystalline form I of vilazodone free base may vary from about 4.7% w/w to 5.0% w/w.

Figure 21:
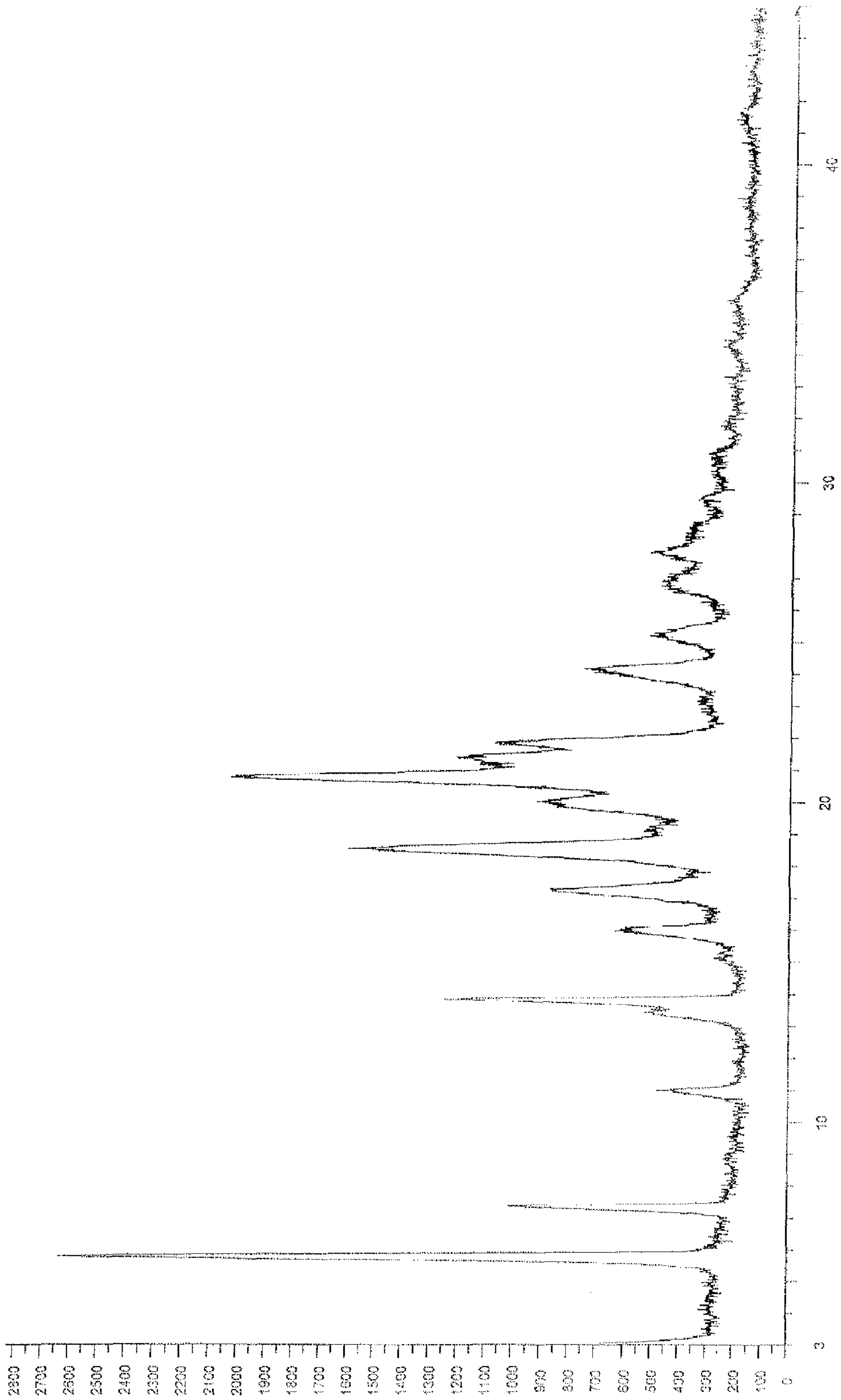
FIG. 21 is an illustration of a PXRD pattern of crystalline form I of vilazodone free base.

It is found that the said variation of water in form I of vilazodone free base does not affect the stability and PXRD pattern of form I which is in accordance with FIG. 21.

One embodiment of the present application relates to Form I of vilazodone free base of the present application may be characterized by its powder X-ray diffraction (PXRD) pattern having peaks at about 5.8, 18.6 and 20.8±0.2 degrees 2θ. One specific embodiment of the present application relates to form I of vilazodone free base which may be characterized by a PXRD pattern having peaks at about 5.8, 13.8, 18.6, 20.8, 21.4 and 21.9±0.2 degrees 2θ. Another specific embodiment of the present application relates to form I of vilazodone free base which may be characterized by a PXRD pattern having peaks at about 5.8, 7.3, 13.8, 17.2, 18.6, 20.0, 20.8, 21.4, 21.9 and 24.2±0.2 degrees 2θ. Form I of vilazodone free base may be characterized by a PXRD pattern substantially as illustrated in FIG. 21.

Figure 22:
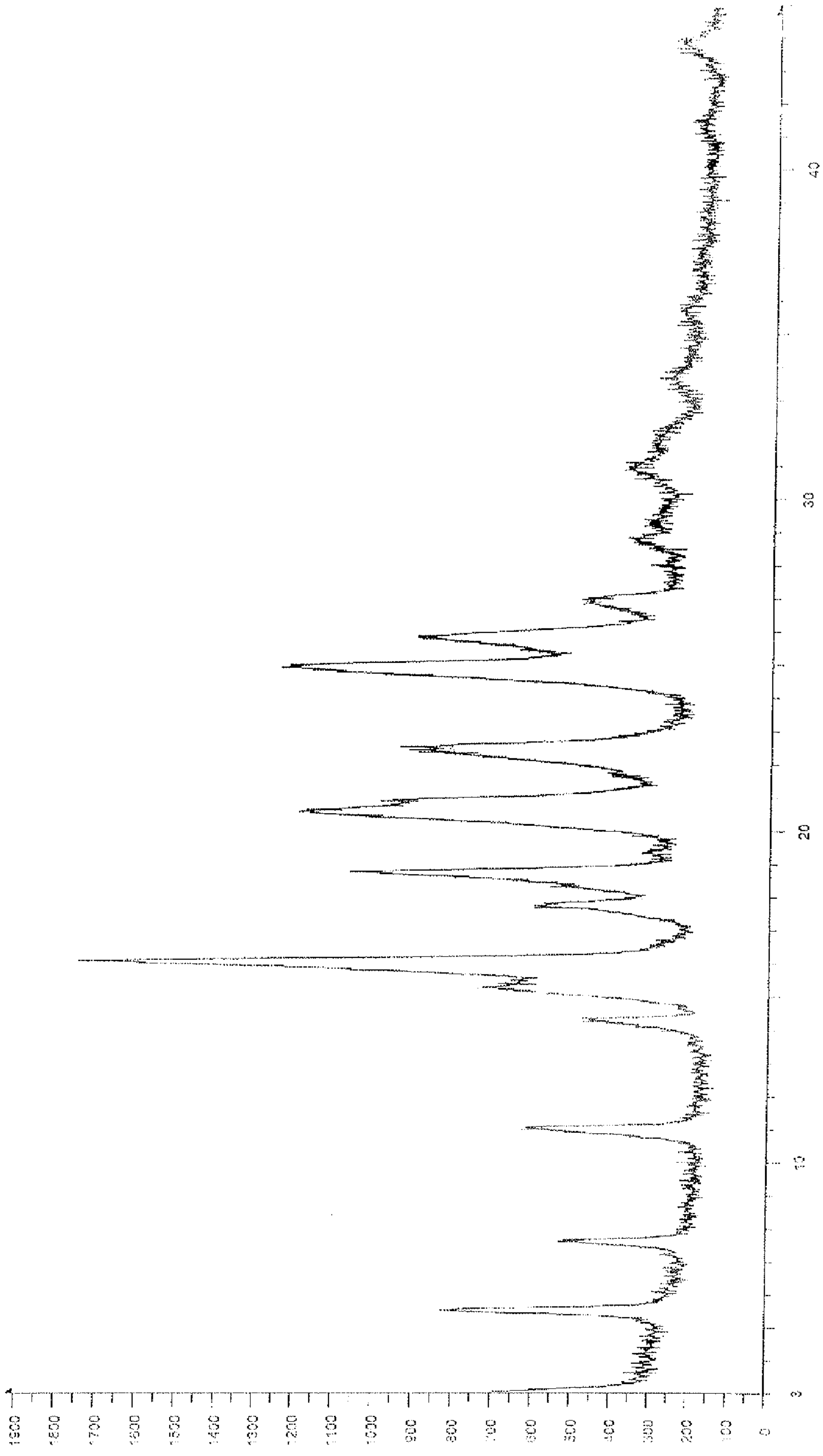
FIG. 22 is an illustration of a PXRD pattern of a crystalline form II of vilazodone free base obtained by the prior art process of reference example 1.

Vilazodone free base when prepared by a process as taught in the US'916 patent produces a crystalline form (hereinafter designated as form II) which is different than form I of vilazodone free base as obtained by the process of the present application. The process as disclosed in the US'916 patent has been followed in reference example 1 and the vilazodone free base obtained by the process has been characterized by PXRD. FIG. 22 denotes the PXRD pattern of form II of vilazodone free base as obtained by the process of reference example 1.

Vilazodone free base obtained by a process as described in the present application may optionally be purified by crystallizing or slurrying in a suitable organic solvent, including but not limited to dimethylformamide; dimethyl sulphoxide; ketones such as acetone, ethyl methyl ketone, butanone; ethers such as tetrahydrofuran, 2-methyl tetrahydrofuran, dioxane; esters such as ethyl acetate, isopropyl acetate; nitriles such as acetonitrile, propionitrile; hydrocarbons such as toluene, xylene; halogenated hydrocarbons such as dichloromethane, chloroform; alcohols such as methanol, ethanol, n-propanol, isopropanol, n-butanol, isobutanol, tert-butanol; water; mixtures thereof.

The pure vilazodone free base obtained by the process as described in the present application may be converted to pharmaceutically acceptable salts, specifically vilazodone hydrochloride by any process as disclosed in prior art references.

The fifty sixth aspect of the present application relates to the use of crystalline form I of vilazodone free base as an intermediate for the preparation of vilazodone hydrochloride. Specifically, the present application relates to a process for preparation of crystalline form B or C or D or E or F or G or H or amorphous solid dispersion with PVP or HPMC of vilazodone hydrochloride or pure amorphous vilazodone hydrochloride or mixtures thereof using crystalline form I of vilazodone free base.

The fifty seventh aspect of the present application relates to a process for preparing 3-(4-chlorobutanoyl)-1H-indole-5-carbonitrile by treating 5-cyano indole with 4-chlorobuyryl chloride in presence of titanium tetrachloride.

5-Cyano indole may be dissolved in a non-polar solvent including but not limited to hydrocarbon like hexanes, heptanes, toluene; halogenated hydrocarbons like dichloromethane, chloroform, carbon tetrachloride; ethers like diethyl ether, diisopropyl ether, methyl tert-butyl ether, tetrahydrofuran. The solution is cooled to a temperature of about −50° C. to about 15° C. Specifically, the solution is cooled to −20° C. to 10° C. and more specifically the solution is cooled to about 0° C. to about 5° C. and titanium tetrachloride is added to the solution. The reaction mass is stirred for about 30 minutes to about 1 hour and specifically for about 45 minutes. To the reaction mass, 4-chlorobutyryl chloride is added and the reaction mass is stirred for about 1 hour to about 10 hours at about 15° C. to about 50° C. Specifically, the reaction mass is stirred for about 5 hours at about 30° C. The reaction is then quenched by the addition of water and the resulting solid is filtered to provide 3-(4-chlorobutanoyl)-1H-indole-5-carbonitrile. The solid, obtained thus may optionally be purified. The solid is dissolved in a polar aprotic organic solvent selected from a group of dimethyl formamide, dimethyl sulfoxide and dimethyl acetamide. The resulting solution is filtered preferably through celite and water is added to the filtrate. The solid is collected by filtration and dried to afford 3-(4-chlorobutanoyl)-1H-indole-5-carbonitrile.

One embodiment of the present application relates to the use of 3-(4-chlorobutanoyl)-1H-indole-5-carbonitrile, prepared by a process described above for the preparation of vilazodone hydrochloride.

The fifty eighth aspect of the present application relates to a process for preparing 3-(4-chlorobutyl)-1H-indole-5-carbonitrile by reducing 3-(4-chlorobutanoyl)-1H-indole-5-carbonitrile in presence of sodium borohydride and boron trifluoride etherate.

It is observed by the inventors of the present application that reduction of 3-(4-chlorobutanoyl)-1H-indole-5-carbonitrile by sodium borohydride is feasible only when borane is generated in-situ because of the presence of cyano group in the starting material. To a solution of 3-(4-chlorobutanoyl)-1H-indole-5-carbonitrile in an organic solvent including but not limited to ethers like diethyl ether, diisopropyl ether, methyl tert-butyl ether, tetrahydrofuran; dimethyl formamide; dimethyl sulfoxide; halogenated hydrocarbons like dichloromethane, chloroform, carbon tetrachloride sodium borohydride and boron trifluoride etherate are added lot wise under nitrogen atmosphere until the completion of the reaction. The reaction is quenched by addition of water and extracted with an organic solvent which is immiscible with water. The product obtained thus may optionally be purified by techniques known in the art.

Another embodiment of the present application relates to the use of 3-(4-chlorobutyl)-1H-indole-5-carbonitrile, prepared by a process described above for the preparation of vilazodone hydrochloride.

The fifty ninth aspect of the present application relates to pharmaceutical compositions comprising crystalline form B or C or D or E or F or G or H or amorphous solid dispersion with a pharmaceutically acceptable carrier such as polyvinylpyrrolidone (PVP) or hydroxypropyl methylcellulose (HPMC) of vilazodone hydrochloride or pure amorphous vilazodoen hydrochloride or mixtures thereof, together with one or more pharmaceutically acceptable excipients.

Crystalline form B or form C or form D or form E or form F or form G or form H or amorphous solid dispersion of vilazodone hydrochloride or pure amorphous vilazodone hydrochloride or mixture thereof, together with one or more pharmaceutically acceptable excipients of the present application may be formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release, or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir or combination of matrix and reservoir systems. The compositions may be prepared using any one or more of techniques such as direct blending, dry granulation, wet granulation, and extrusion and spheronization. Compositions may be presented as uncoated, film coated, sugar coated, powder coated, enteric coated, and modified release coated.

Pharmaceutically acceptable excipients that are useful in the present application include, but are not limited to: diluents such as starches, pregelatinized starches, lactose, powdered celluloses, microcrystalline celluloses, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methyl celluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, or neutral surfactants; complex forming agents such as various grades of cyclodextrins and resins; and release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that are useful include, but are not limited to, film formers, plasticizers, colorants, flavoring agents, sweeteners, viscosity enhancers, preservatives, antioxidants, and the like.

In general, crystalline forms of drug substances may be characterized by diffraction techniques, such as e.g., X-ray powder diffraction, by spectroscopic methods, e.g., infrared and $^{13}C$ nuclear magnetic resonance spectroscopy, and by thermal techniques, e.g., differential scanning calorimetry and thermogravimetric analysis. Crystalline polymorphic forms of the present application are best characterized by the X-ray powder diffraction pattern determined in accordance with procedures that are known in the art. For a discussion of these techniques see J. Haleblian, J. Pharm. Sci. 1975 64:1269-1288, and J. Haleblian and W. McCrone, J. Pharm. Sci. 1969 58:911-929. Polymorphic forms of the present application can be further processed to modulate particle sizes. For example, the crystalline form B of vilazodone hydrochloride of the present application can be milled, to reduce average crystal size and/or to prepare a sample suitable for manipulation and formulation.

In general, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ±0.2°) of 19.6°" means "having a diffraction peak at a diffraction angle (2θ) of 19.4° to 19.8°". Although the intensities of peaks in the x-ray powder diffraction patterns of different batches of a compound may vary slightly, the peaks and the peak locations are characteristic for a specific polymorphic form. The relative intensities of the XRD peaks can vary depending on the sample preparation technique, crystal size distribution, various filters used, the sample mounting procedure, and the particular instrument employed. Moreover, instrument variation and other factors can affect the 2-theta values. Also, new peaks may be observed or existing peaks may disappear, depending on the type of the machine or the settings, for example, whether a Ni filter is used or not.

The PXRD conditions for the measurement of PXRD peaks of crystalline forms of vilazodone hydrochloride of the present application are as follows:

Range: 3° 2θ to 40° 2θ in conventional reflection mode
Instrument: PANalytical X-ray Diffractometer
Detector: X'celerator
Source: Copper K-alpha radiation (1.5418 Angstrom).

Differential Scanning Calorimetry (DSC) analysis of crystalline forms of vilazodone hydrochloride of the present application was carried out using a TA Q1000 DSC with a ramp of 10° C./minute up to 300° C.

TGA analysis of crystalline forms of vilazodone hydrochloride of the present application was carried out in a TGA Q500 instrument with a ramp of 10° C./minute up to 200° C.

IR spectrum of crystalline forms of vilazodone hydrochloride of the present application was taken in Perkin Elmer—Spectrum 100, FT-IR spectrometer. The sample was mixed with KBr, grinded and scanned from 4000 $cm^{-1}$ to 450 $cm^{-1}$.

Definitions

The following definitions are used in connection with the present application unless the context indicates otherwise.

The term "antisolvent" refers to a liquid that, when combined with a solution of vilazodone hydrochloride, reduces solubility of the vilazodone hydrochloride in the solution, causing crystallization or precipitation in some instances spontaneously, and in other instances with additional steps, such as seeding, cooling, scratching, and/or concentrating.

The terms "about," "general, 'generally," and the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

A name used herein to characterize a polymorphic form for example, hydrates, mixed solvates and amorphous solid dispersions should not be considered limiting with respect to any other substance possessing similar or identical physical and chemical characteristics, but rather it should be understood that these designations are mere identifiers that should be interpreted according to the characterization information also presented herein.

As used herein "polymorphs" refer to different crystalline forms of the same pure substance in which the molecules have different spatial arrangements of the molecules, atoms, and/or ions forming the crystal.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

Certain specific aspects and embodiments of the present application will be explained in greater detail with reference to the following examples, which are provided only for purposes of illustration and should not be construed as limiting the scope of the disclosure in any manner.

EXAMPLES

Example 1: Preparation of Crystalline Form B of Vilazodone Hydrochloride

Example 1a

Vilazodone free base (118 g) and methanol (2360 mL) were charged into a round bottom flask at ambient temperature. The resulting mixture was cooled to 4° C. and 10% w/w methanolic hydrochloric acid solution (236 mL) was slowly added, stirred the resulting solution at 0-5° C. for 30 minutes. The solid was collected by filtration and dried at 45-50° C. for 3.5 hours to afford the title compound.

Yield: 107.6 g;

Water Content: 8.46% w/w as measured by Karl Fischer method.

Figure 1:
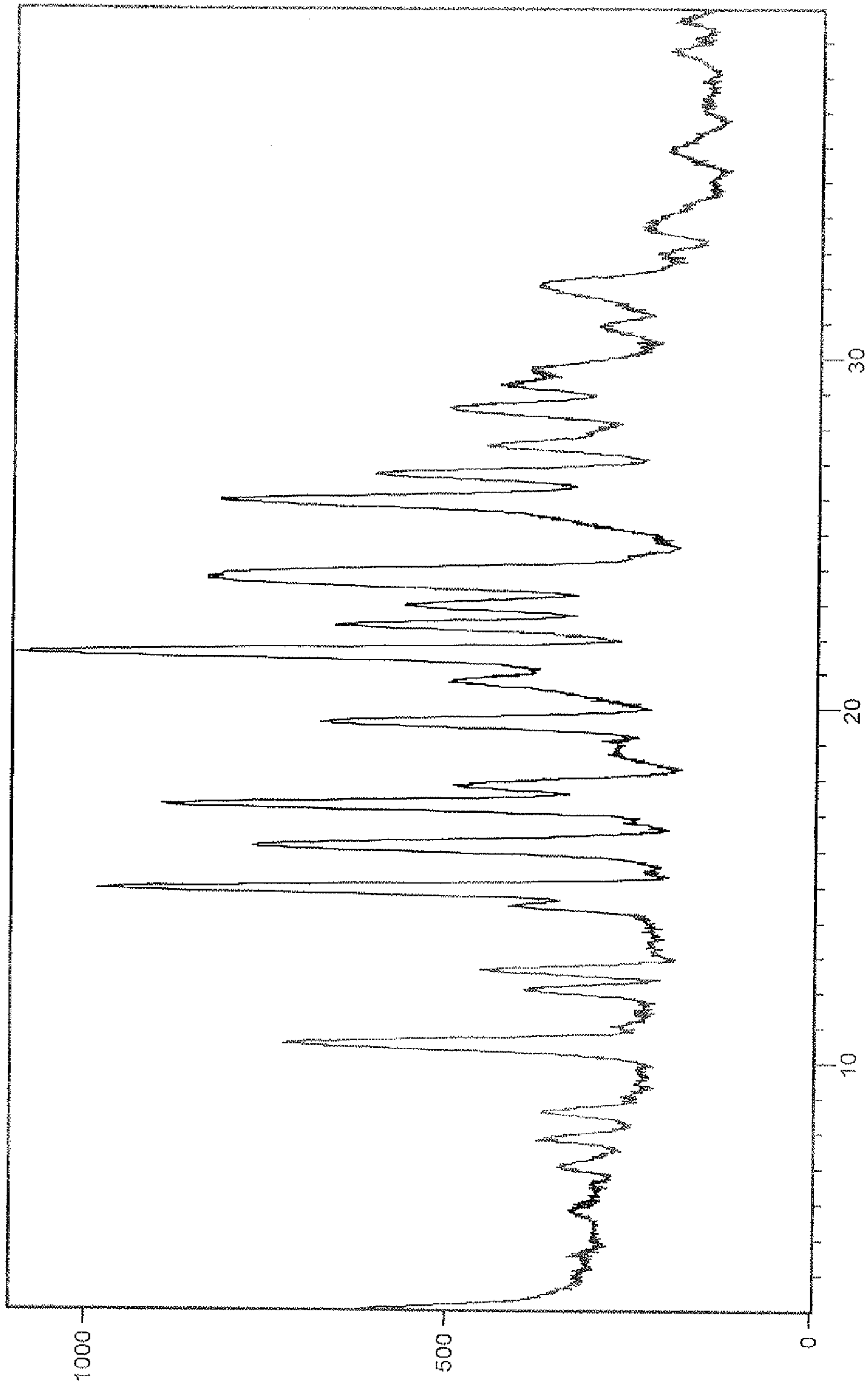

The PXRD pattern of crystalline Form B of vilazodone hydrochloride obtained is in accordance with FIG. 1.

Example 1b

Vilazodone free base (1.5 g) and methanol (30 mL) were charged into a round bottom flask at −10° C. 10% w/w Methanolic hydrochloric acid solution (3 mL) was slowly added to the resulting mixture at −10° C. and further stirred for 30 minutes. The solid was collected by filtration and dried at 45-50° C. for 30 minutes to afford the title compound.

Yield: 1.4 g

Water Content: 8.46% w/w as measured by Karl Fischer method.

Figure 2:
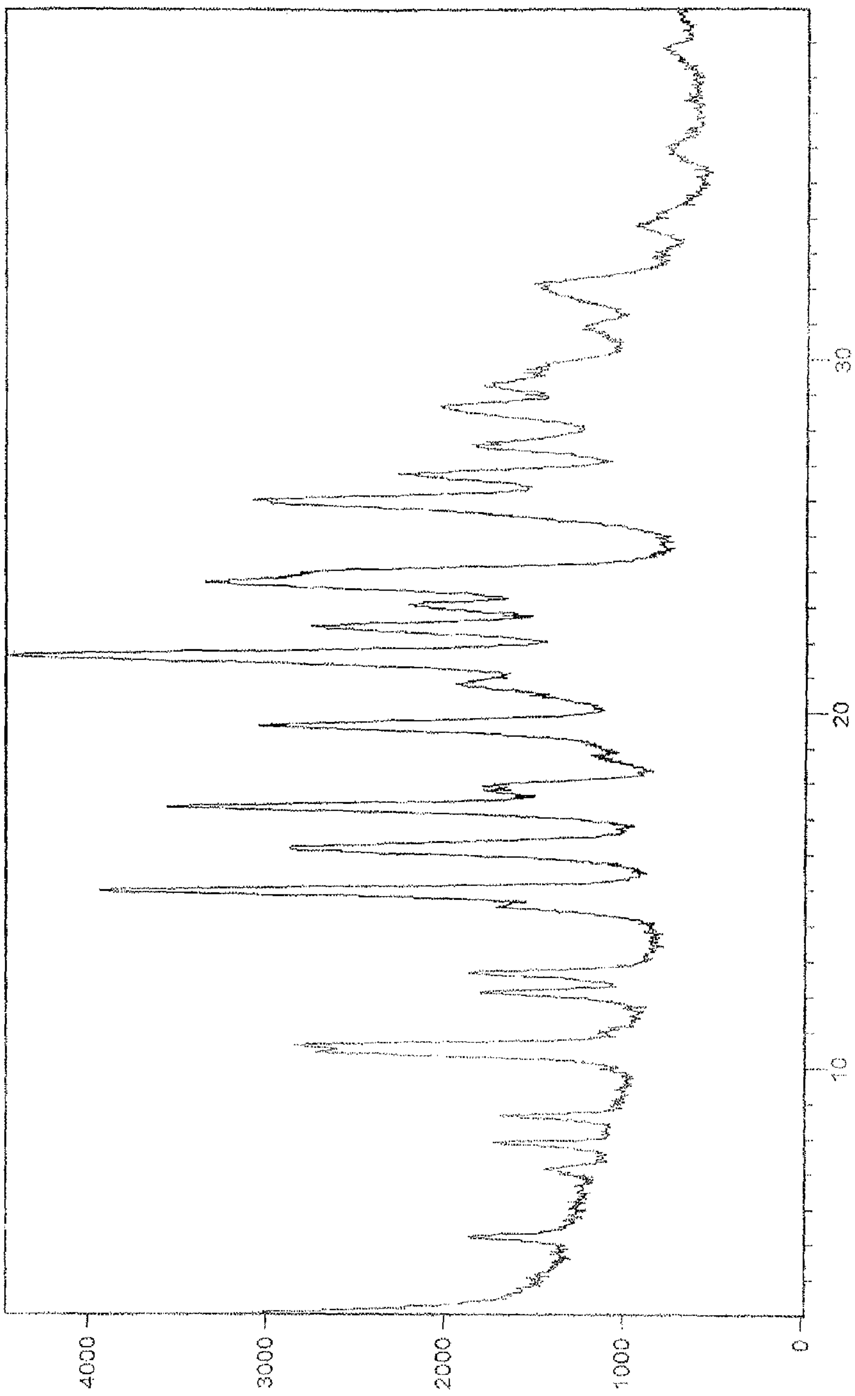
FIG. 2 is an illustration of a PXRD pattern of crystalline form B of vilazodone hydrochloride as obtained from example 1b.

The PXRD pattern of crystalline Form B of vilazodone hydrochloride obtained is in accordance with FIG. 2.

Example 1c

Vilazodone free base (1.5 g) and methanol (30 mL) were charged into a round bottom flask at −10° C. then added a seed of crystalline form B of vilazodone hydrochloride (150 mg) obtained from example 1b. 10% w/w Methanolic hydrochloric acid solution (3 mL) was slowly added to the resulting mixture at −10° C. and further stirred for 20 minutes. The solid was collected by filtration and dried at 45-50° C. for 30 minutes to afford the title compound.

Yield: 1.4 g

Water Content: 7.42% w/w as measured by Karl Fischer method.

Figure 3:
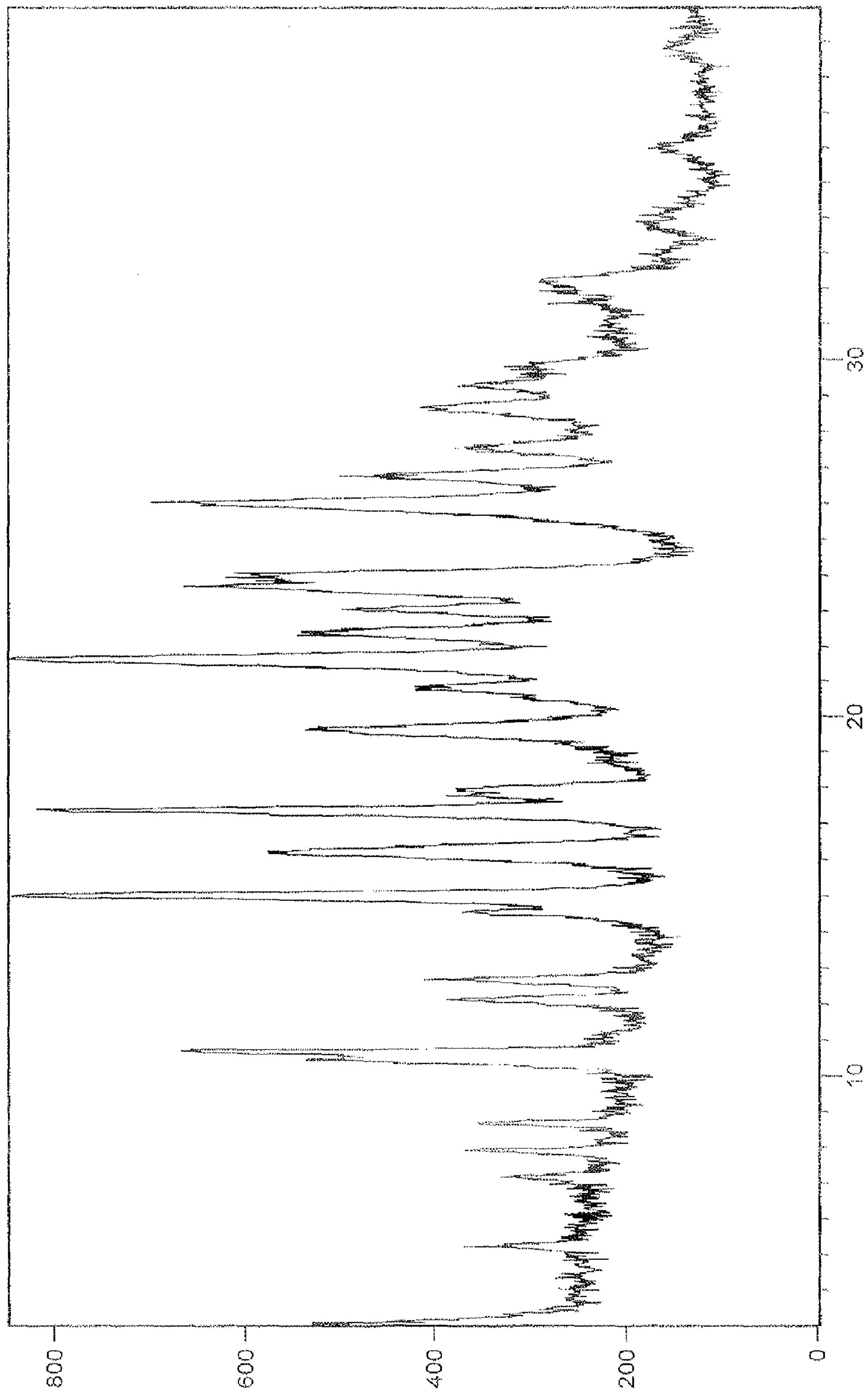
FIG. 3 is an illustration of a PXRD pattern of crystalline form B of vilazodone hydrochloride as obtained from example 1c.

The PXRD pattern of crystalline Form B of vilazodone hydrochloride obtained is in accordance with FIG. 3.

Example 1d

Vilazodone free base (200 mg) and methanol (4 mL) were charged into a round bottom flask at −4° C. 10% w/w Methanolic hydrochloric acid solution (0.4 mL) was slowly added to the resulting mixture at −4° C. and further stirred for 20 minutes. The solid was collected by filtration and dried at 45-50° C. for 30 minutes to afford the title compound.

Yield: 160 mg.

Figure 4:
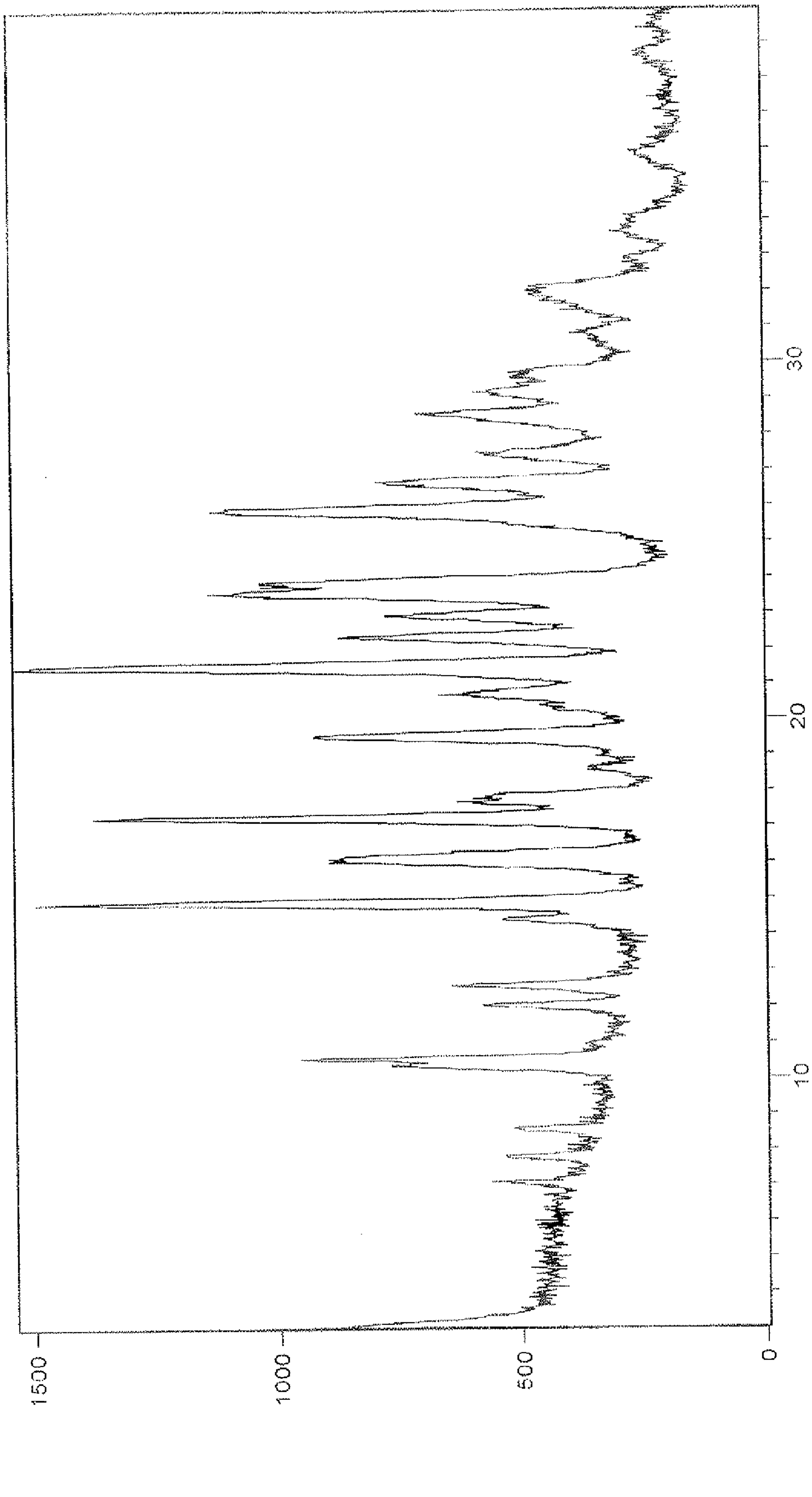
FIG. 4 is an illustration of a PXRD pattern of crystalline form B of vilazodone hydrochloride as obtained from example 1d.

The PXRD pattern of crystalline Form B of vilazodone hydrochloride obtained is in accordance with FIG. 4.

Example 1e

Vilazodone free base (0.5 g) and methanol (10 mL) were charged into a round bottom flask at −10° C. 10% w/w Methanolic hydrochloric acid solution (1 mL) was slowly added to the resulting mixture at −10° C. and further stirred for 20 minutes. The solid was collected by filtration and dried at 45-50° C. for 30 minutes to afford the title compound.

Yield: 4.2 mg

Water Content: 8.12% w/w as measured by Karl Fischer method.

Figure 5:
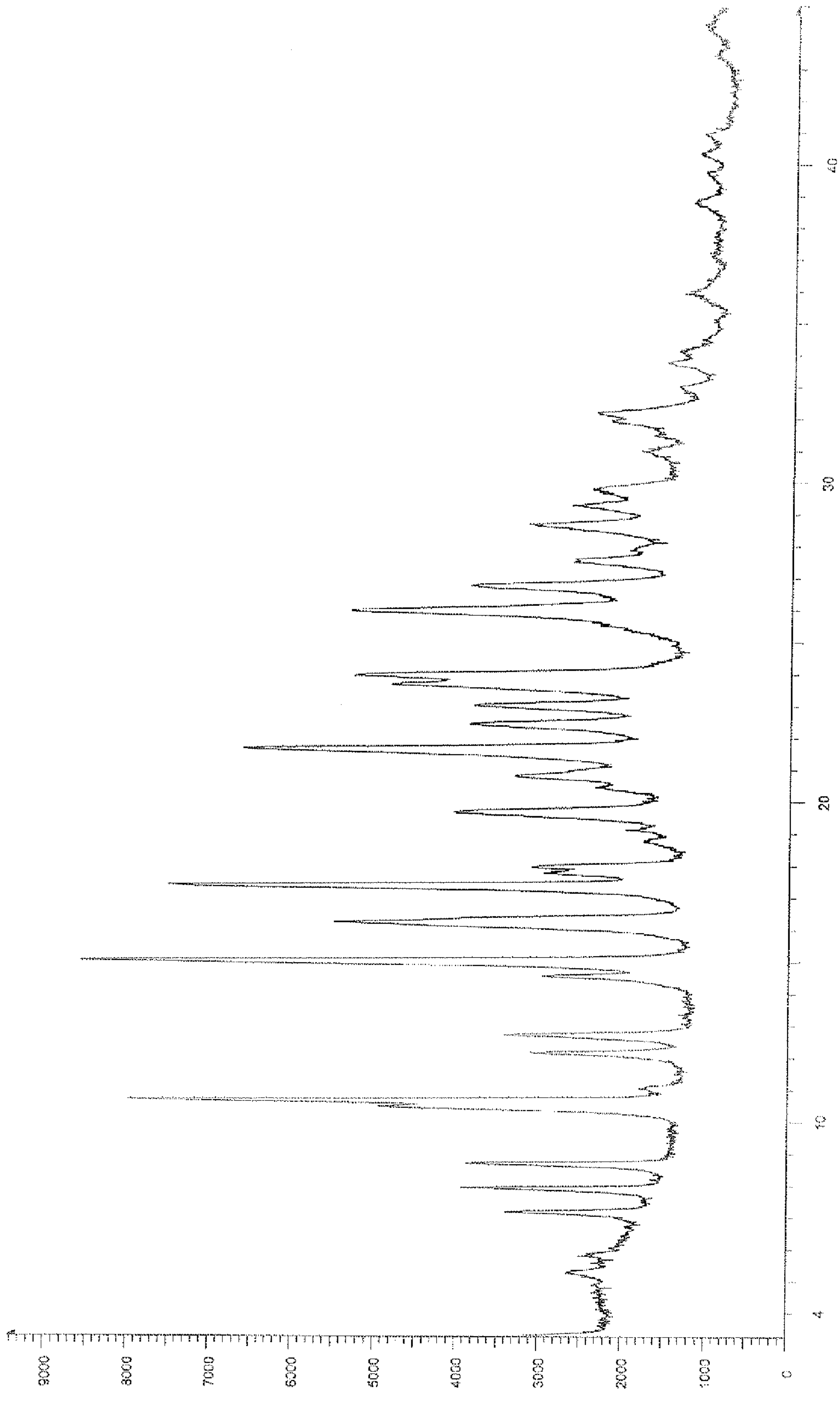
FIG. 5 is an illustration of a PXRD pattern of crystalline form B of vilazodone hydrochloride as obtained from example 1e.

The PXRD pattern of crystalline Form B of vilazodone hydrochloride obtained is in accordance with FIG. 5.

Example 1f

Vilazodone free base (50 g) was added to methanol (1000 mL) at about 25-30° C. and the mixture was cooled to −10° C. to −15° C. Crystalline Form B of vilazodone hydrochloride (5 g) was added to the above mixture as a seeding material. Methanolic hydrochloric acid (Assay: 16% w/w, 28.4 g) was added drop wise to the above mixture maintaining at the same temperature. The reaction mixture was stirred at −10° C. to −15° C. for 1 to 2 hours. The reaction mass was filtered in PNF (Pressure Nutsch Filter) in presence of nitrogen. The wet cake was washed with chilled methanol (100 mL) and suck dried under dry air or nitrogen for 1-2 hours. The wet material was humidified with humid air (RH 30-70%) for 4 hours and dried in air tray drier at 40-45° C. for 15 hours to afford constant weight of crystalline Form B of vilazodone hydrochloride.

Yield: 54 g (84%)

Purity by HPLC: 99.66%

Water Content: 7.59% w/w

Example 1g

Vilazodone free base (100 g) was added to methanol (2000 mL) at about 25-30° C. and the mixture was cooled to −10° C. to −15° C. Crystalline Form B of vilazodone hydrochloride (10 g) was added to the above mixture. Methanolic hydrochloric acid (Assay: 16% w/w, 56.4 g) was added drop wise to the above mixture maintaining the temperature. The reaction mixture was maintained at −10° C. to −15° C. for 1 to 2 hours. The reaction mass was filtered in ANFD (Agitated Nutsch Filter Drier) by maintaining the ANFD jacket temperature at −10° C. The wet cake was washed with chilled methanol (2×100 mL) and suck dried under vacuum maintaining atmospheric pressure by supplying dry air or nitrogen for 1-2 hours. The ANFD jacket temperature was raised to 25-30° C. and the wet material is humidified with humid air (RH 30-70%) for 3 hours. The material was dried for 15 hours at 40-45° C. to afford constant weight of crystalline Form B of vilazodone hydrochloride.

Yield: 116 g (90%)

Water Content: 7.69%

Example 1h

Vilazodone free base (50 g) was added to methanol (1000 mL) at about 25-30° C. and the mixture was cooled to −10°

C. to −15° C. Crystalline Form B of vilazodone hydrochloride (5 g) was added to the above mixture. Slowly, methanolic hydrochloric acid (Assay: 11.09% w/w, 41.9 g) was added to the above mixture maintaining the temperature. The reaction mixture was maintained at −10° C. to −15° C. for 1 to 2 hours. The reaction mass was filtered in Buchner funnel and was washed with chilled methanol (100 mL). The wet cake was suck dried under vacuum for 1-2 hours and then dried in air tray drier at 40-45° C. for 2 hours to afford constant weight of crystalline Form B of vilazodone hydrochloride.

Yield: 58 g (90%)

Purity by HPLC: 99.62%

Water Content: 7.37% w/w

Example 1i

Vilazodone free base (900 g) was added to methanol (13.5 L) at about 20-25° C. and the mixture was cooled to −10° C. to −17° C. Crystalline Form B of vilazodone hydrochloride (45 g) was added to the above mixture. A solution of methanolic hydrochloric acid (Assay: 9%, 908 g) was added slowly over a period of about 1 hour to the above mixture maintaining the temperature. After the addition was complete, the reaction mixture was stirred at −10° C. to −14° C. for about 1 hour. The reaction mixture was filtered by ANFD and the solid was washed with pre-chilled methanol (1.8 L). The solid was suck-dried for about 2 hours while maintaining the jacket temperature of ANFD at about −4° C. The ANFD jacket temperature was allowed to increase to 30° C. and the solid was unloaded from ANFD. The solid was dried in air tray drier at 25-35° C. for a period of about 40 hours maintaining the relative humidity of air at about 40%.

Yield: 978 g (99.5%)

Purity by HPLC: 99.81%

Water content: 7.45%

Particle Size:

D(0.1): 3 μm

D(0.5): 8.2 μm

D(0.9): 17.34 μm

Example 2: Preparation of Crystalline Form C of Vilazodone Hydrochloride

Example 2a

Vilazodone hydrochloride Form B (2 g) obtained from example 1a, was dried at 80° C. for 5 hours in air tray dryer (ATD) to afford the title compound.

Yield: 1.9 g

Water Content: 7.89% w/w.

The PXRD pattern of crystalline Form C of vilazodone hydrochloride obtained is in accordance with FIG. 6.

Example 2b

Vilazodone hydrochloride Form B (200 mg) obtained from example 1b, was dried at 80° C. for 1.5 hours in air tray dryer (ATD) to afford the title compound.

Yield: 190 mg

Water Content: 7.96% w/w.

The PXRD pattern of crystalline Form C of vilazodone hydrochloride obtained is in accordance with FIG. 7.

Example 2c

Vilazodone free base (1.0 g) and methanol (20 mL) were charged into a round bottom flask at −8° C. 10% w/w Methanolic hydrochloric acid solution (2 mL) was slowly added to the resulting mixture at −8° C. and further stirred for 20 minutes. The solid was collected by filtration and dried at 45-50° C. for 30 minutes to afford the Form B of vilazodone hydrochloride having PXRD pattern is in accordance with FIG. 2.

Vilazodone hydrochloride Form B obtained above was dried at 80° C. for 1 hour in air tray dryer (ATD) to afford the title compound.

Water Content: 8.09% w/w.

The PXRD pattern of crystalline Form C of vilazodone hydrochloride obtained is in accordance with FIG. 8.

Example 3: Preparation of Crystalline Vilazodone Hydrochloride Form D

A clear solution of vilazodone hydrochloride (2 g) in dimethyl sulfoxide (30 mL) was added to ethyl acetate (150 mL) at ambient temperature, the resulted mixture was stirred at the same temperature for 30 minutes. The solid was collected by filtration under reduced pressure and dried in a vacuum tray drier (VTD) at 50° C. for 35 minutes to afford the title compound.

Yield: 1.8 g

The PXRD pattern of vilazodone hydrochloride Form D obtained is in accordance with FIG. 9.

Example 4: Preparation of Crystalline Vilazodone Hydrochloride Form E

A clear solution of vilazodone hydrochloride (2 g) in N-methyl-2-pyrrolidone (24 mL) was added to dichloromethane (150 mL) at ambient temperature, the resulted mixture was stirred at the same temperature for 25 minutes. The solid was collected by filtration under reduced pressure and dried in a vacuum tray drier (VTD) at 50° C. for 40 minutes to afford the title compound.

Yield: 1.7 g

The PXRD pattern of vilazodone hydrochloride Form E obtained is in accordance with FIG. 10.

Example 5: Preparation of Crystalline Vilazodone Hydrochloride Form F

A clear solution of vilazodone hydrochloride (2 g) in N,N-dimethylformamide (50 mL) was added to ethyl acetate (150 mL) at ambient temperature, the resulted mixture was stirred at the same temperature for 25 minutes. The solid was collected by filtration under reduced pressure and dried in a vacuum tray drier (VTD) at 50° C. for 30 minutes to afford the title compound.

Yield: 1.87 g

The PXRD pattern of vilazodone hydrochloride Form F obtained is in accordance with FIG. 11.

Example 6: Preparation of Amorphous Solid Dispersion of Vilazodone Hydrochloride with Polyvinylpyrrolidone (PVP)

Vilazodone hydrochloride (100 mg), methanol (60 mL) and polyvinylpyrrolidone (PVP) (100 mg) were charged into a round bottom flask at ambient temperature. The resulting mixture was heated and stirred for 25 minutes at 60° C. The resulting solution was filtered and the filtrate was distilled off under reduced pressure at 75-80° C. to afford the title compound.

Yield: 70 mg

The PXRD pattern of amorphous solid dispersion of vilazodone hydrochloride with polyvinylpyrrolidone (PVP) obtained is in accordance with FIG. 12.

Example 7: Preparation of Amorphous Solid Dispersion of Vilazodone Hydrochloride with Hydroxypropyl Methylcellulose (HPMC)

Vilazodone hydrochloride (100 mg), methanol (100 mL) and hydroxypropyl methylcellulose (HPMC) (100 mg) were charged into a round bottom flask at ambient temperature. The resulting mixture was heated and stirred for 25 minutes at 60° C. The resulting solution was filtered and the filtrate was distilled off under reduced pressure at 75-80° C. to afford the title compound.

Yield: 150 mg

The PXRD pattern of amorphous solid dispersion of vilazodone hydrochloride with hydroxypropyl methylcellulose (HPMC) obtained is in accordance with FIG. 12.

Example 8: Preparation of Crystalline Form G of Vilazodone Hydrochloride

Example 8a

Vilazodone free base (50 g) was added to methanol (1000 mL) at about 25-30° C. and the mixture was cooled to −10° C. to −15° C. Crystalline Form B of vilazodone hydrochloride (5 g) was added to the above mixture as a seeding material. Methanolic hydrochloric acid (Assay: 16% w/w, 28.4 g) was added drop wise to the above mixture maintaining at the same temperature. The reaction mixture was stirred at −10° C. to −15° C. for 1 to 2 hours. The reaction mass was filtered in PNF (Pressure Nutsch Filter) in presence of nitrogen. The wet cake was washed with chilled methanol (100 mL) and suck dried for 1-2 hours to afford form G of vilazodone hydrochloride.

Example 8b

Vilazodone free base (50 g) was added to methanol (1000 mL) at about 25-30° C. and the mixture was cooled to −10° C. to −15° C. Crystalline Form B of vilazodone hydrochloride (5 g) was added to the above mixture as a seeding material. Methanolic hydrochloric acid (Assay: 16.01% w/w, 28.4 g) was added drop wise to the above mixture maintaining at the same temperature. The reaction mixture was stirred at −10° C. to −15° C. for 1 to 2 hours. The reaction mass was filtered in PNF (Pressure Nutsch Filter) in presence of nitrogen. The wet cake was washed with chilled methanol (100 mL) and suck dried for 1-2 hours to provide form G of vilazodone hydrochloride.

Example 8c

Vilazodone free base (100 g) was added to methanol (2000 mL) at about 25-30° C. and the mixture was cooled to −15° C. to −20° C. Crystalline Form B of vilazodone hydrochloride (10 g) was added to the above mixture as a seeding material. Methanolic hydrochloric acid (Assay: 16% w/w, 56.4 g) was added drop wise to the above mixture maintaining at the same temperature. The reaction mixture was stirred at −10° C. to −15° C. for 1 to 2 hours. The reaction mass was filtered in ANFD (Agitated Nutsch Filter Drier) by maintaining the ANFD jacket temperature at −10° C. The wet cake was washed with chilled methanol (200 mL) and suck dried under vacuum maintaining atmospheric pressure by supplying dry air or nitrogen for 1-2 hours to afford form G of vilazodone hydrochloride.

Example 8d

Vilazodone free base (5 g) was added to methanol (100 mL) at about 25-30° C. and the mixture was cooled to −15° C. to −20° C. Crystalline Form IV of vilazodone hydrochloride (0.25 g) was added to the above mixture as a seeding material. Methanolic hydrochloric acid (Assay: 16% w/w, 2.84 g) was added drop wise to the above mixture maintaining at the same temperature. The reaction mixture was stirred at −10° C. to −15° C. for 3 hours. The reaction mass was filtered in PNF (Pressure Nutsch Filter) in presence of nitrogen. The wet cake was washed with chilled methanol (10 mL) and suck dried for 10-15 minutes to provide form G of vilazodone hydrochloride.

Example 8e

Vilazodone free base (5 g) was added to methanol (100 mL) at about 25-30° C. and the mixture was cooled to −15° C. to −20° C. Crystalline Form V of vilazodone hydrochloride (0.25 g) was added to the above mixture as a seeding material. Methanolic hydrochloric acid (Assay: 16% w/w, 2.84 g) was added drop wise to the above mixture maintaining at the same temperature. The reaction mixture was stirred at −10° C. to −15° C. for 2 hours. The reaction mass was filtered in PNF (Pressure Nutsch Filter) in presence of nitrogen. The wet cake was washed with chilled methanol (10 mL) and suck dried for 10-15 minutes to afford form G of vilazodone hydrochloride.

Example 8f

Vilazodone free base (5 g) was added to methanol (100 mL) at about 25-30° C. and the mixture was cooled to −15° C. to −20° C. Methanolic hydrochloric acid (Assay: 16% w/w, 2.84 g) was added drop wise to the above mixture maintaining at the same temperature. The reaction mixture was stirred at −10° C. to −15° C. for 2 hours. The reaction mass was filtered in PNF (Pressure Nutsch Filter) in presence of nitrogen. The wet cake was washed with chilled methanol (10 mL) and suck dried for 10-15 minutes to provide form G of vilazodone hydrochloride.

Example 8g

Vilazodone free base (25 g) was added to methanol (500 mL) at about 25-30° C. and the mixture was cooled to −15° C. to −20° C. Crystalline Form B of vilazodone hydrochloride (2.5 g) was added to the above mixture as a seeding material. Methanolic hydrochloric acid (Assay: 10% w/w, 57.5 mL) was added drop wise to the above mixture maintaining at the same temperature. The reaction mixture was stirred at −10° C. to −15° C. for 2 hours. The reaction mass was filtered and suck-dried for 30 minutes to afford form G of vilazodone hydrochloride.

Example 8h

Vilazodone free base (500 g) was added to methanol (7.5 L) at about 27-30° C. and the mixture was cooled to about −10° C. to −15° C. Crystalline Form B of vilazodone hydrochloride (25 g) was added to the above mixture as a seeding material. Methanolic hydrochloric acid (Assay: 5.97% w/w, 790 g) was added drop wise to the above mixture maintaining at the same temperature. The reaction mixture was stirred at −10° C. to −15° C. for about 2 hours. The reaction mass was filtered in ANFD and washed with methanol (1 L). The wet cake was suck-dried maintaining the ANFD jacket temperature between about −2 and −5° C. for about 3 hours to afford form G of vilazodone hydrochloride.

Example 9: Preparation of Crystalline Form H of Vilazodone Hydrochloride

Example 9a

Vilazodone free base (5 g) was added to methanol (100 mL) at about 25-30° C. and the mixture was cooled to −10° C. to −15° C. Crystalline Form B of vilazodone hydrochloride (0.5 g) was added to the above mixture as a seeding material. Methanolic hydrochloric acid (Assay: 11.3% w/w, 2.62 g) was added drop wise to the above mixture maintaining at the same temperature. The reaction mixture was stirred at −10° C. to −15° C. for 1 to 2 hours. The reaction mass was filtered Buchner funnel and washed with water (20 mL). The wet cake was suck-dried under atmospheric RH for about 3 hours and dried in air tray drier at 40° C. for 1-2 hours. The crystalline vilazodone hydrochloride obtained after drying was stirred in water (90 mL) overnight and filtered to afford form H of vilazodone hydrochloride.

Methanol Content: 78 ppm

Water Content: 6.04% w/w

Example 9b

Vilazodone free base (50 g) was added to methanol (100 mL) at about 25-30° C. Crystalline Form B of vilazodone hydrochloride (0.5 g) was added to the above mixture as a seeding material. Methanolic hydrochloric acid (Assay: 11.3% w/w, 3.54 g) was added drop wise to the above mixture maintaining at the same temperature. The reaction mixture was stirred for overnight. The reaction mass was filtered in Buchner funnel and suck-dried under atmospheric RH for about 3 hours and dried in air tray drier at 40° C. for 1-2 hours. The dried material was stirred in water (100 mL) for 12 days and filtered to afford form H of vilazodone hydrochloride.

Methanol Content: 907 ppm

Water Content: 7.36% w/w

Example 10: Preparation of Pure Amorphous Form of Vilazodone Hydrochloride

Example 10a

Crystalline Form B of vilazodone hydrochloride (2.5 g) was charged in a ball-milling vessel. The material is milled for about 2 hours at about 300 rpm. The product was unloaded from the vessel to afford the title compound.

Yield: 2.10 g

Purity (by HPLC): 98.93%

Water content: 5.73% w/w

Example 10b

Crystalline Form C of vilazodone hydrochloride (2.5 g) was charged in a ball-milling vessel. The material is milled for about 2 hours at about 300 rpm. The product was unloaded from the vessel to afford the desired compound.

Yield: 2.10 g

Purity (by HPLC): 98.97%

Water content: 5.99% w/w

Example 10c

Crystalline Form C of vilazodone hydrochloride (5.0 g) was dissolved in a mixture of dimethylformamide (200 mL) and water (50 mL). The undissolved particles were filtered and the filtrate was spray dried at 165° C. The solid was collected and dried in a vacuum tray dryer at 45° C. for 3 hours to afford the title compound.

Yield: 2.8 g

Purity (by HPLC): 98.68%

Water content: 5.21% w/w

Example 11: Preparation of Form I of Vilazodone Free Base

Example 11a

To a solution of 3-(4-chlorobutyl)-1H-indole-5-carbonitrile (5 g) in DMF (15 mL), sodium iodide (1.61 g) was added and the reaction mass was stirred at about 26° C. for 10-15 minutes. Diisopropylethylamine (13.9 g) and 5-(piperazin-1-yl)benzofuran-2-carboxamide (6.3 g) was added to the reaction mass and heated to 110-115° C. for 4-6 hours. The reaction mass was then allowed to cool to 50-60° C. and water (75 mL) was added to the reaction mass slowly. The resulting precipitate was stirred for 30-45 minutes at about 30° C. The precipitate was filtered, washed with water (25 mL) and dried for 4-6 hours at 65-70° C. to afford the title compound.

Yield: 8.2 g (86.22%)

Purity (by HPLC): 95.63%

Water content: 4.89% w/w

Example 11 b

To a solution of 3-(4-chlorobutyl)-1H-indole-5-carbonitrile (5 g) in DMF (15 mL), sodium iodide (1.61 g) was added and the reaction mass was stirred at about 26° C. for 10-15 minutes. Diisopropylethylamine (13.9 g) and 5-(piperazin-1-yl)benzofuran-2-carboxamide (6.3 g) was added to the reaction mass and heated to 90-100° C. for 8 hours. The reaction mass was then allowed to cool to 50-60° C. and water (75 mL) was added to the reaction mass slowly. The resulting precipitate was stirred for 30-45 minutes at about 30° C. The precipitate was filtered, washed with water (25 mL) and dried for 4-6 hours at 60-65° C. to afford the desired compound.

Yield: 8.4 g (88.32%)

Purity (by HPLC): 95.24%

Water content: 5.08% w/w

Example 11c

To a solution of 3-(4-chlorobutyl)-1H-indole-5-carbonitrile (25 g) in DMF (75 mL), sodium iodide (8 g) was added and the reaction mass was stirred at about 25-30° C. for 10-15 minutes. Sodium bicarbonate (35.9 g) and 5-(piperazin-1-yl)benzofuran-2-carboxamide (29 g) was added to the reaction mass and heated to 110-115° C. for 1 hour and 10 minutes. The reaction mass was then allowed to cool to 50-60° C. and water (375 mL) was added to the reaction mass slowly. The resulting precipitate was stirred for 45-60 minutes at about 30° C. The precipitate was filtered, washed with water (2×50 mL) and dried for 4-6 hours at 50-60° C. under vacuum to afford the title compound.

Yield: 44.5 g (93.7%)

Purity (by HPLC): 96.55%

Example 11d

To a solution of 3-(4-chlorobutyl)-1H-indole-5-carbonitrile (2.5 g) in DMF (10 mL), tetrabutylammonium bromide (0.68 g) was added and the reaction mass was stirred at about 25-30° C. for 20 minutes. Sodium bicarbonate (3.59 g) and 5-(piperazin-1-yl)benzofuran-2-carboxamide (2.9 g) was added to the reaction mass and heated to 110-115° C. for 4 hours. The reaction mass was then allowed to cool to 60° C. and water (37.5 mL) was added to the reaction mass slowly. The resulting precipitate was stirred for 60 minutes at about 30° C. The precipitate was filtered, washed with water (10 mL) and dried for 4-6 hours at 50-60° C. under vacuum to afford the title compound.

Yield: 4.4 g (93.6%)

Purity (by HPLC): 93.62%

Example 11e

To a solution of 3-(4-chlorobutyl)-1H-indole-5-carbonitrile (2.5 g) in DMF (10 mL), sodium iodide (0.8 g) was added and the reaction mass was stirred at about 25-30° C. for 15 minutes. Sodium bicarbonate (3.61 g), 5-(piperazin-1-yl)benzofuran-2-carboxamide (3 g) and tetrabutylammonium bromide (0.51 g) was added to the reaction mass and heated to 110-115° C. for 1 hour and 15 minutes. The reaction mass was then allowed to cool to 60° C. and water (37.5 mL) was added to the reaction mass slowly. The resulting precipitate was stirred for 60 minutes at about 30° C. The precipitate was filtered, washed with water (10 mL) and dried for 5-6 hours at 60° C. under vacuum to afford the desired compound.

Yield: 4.5 g (95.7%)

Purity (by HPLC): 97.39%

Example 11f

A heterogeneous mixture of 3-(4-chlorobutyl)-1H-indole-5-carbonitrile (3 g), 5-(piperazin-1-yl)benzofuran-2-carboxamide (3.8 g) and sodium bicarbonate (2.1 g) in water (30 mL), sodium sulfate (11 g) was added. The reaction mass was heated to 95-100° C. for a period of 9-10 hours. The reaction mass was then allowed to cool to room temperature and water (30 mL) was added. The solid was filtered, washed with water (15 mL) and dried at about 60° C. for 6 hours to afford the desired product.

Yield: 5.2 g (91.2%)

Purity (by HPLC): 89.49%

Example 11g

A mixture of 3-(4-chlorobutyl)-1H-indole-5-carbonitrile (5 g), 5-(piperazin-1-yl)benzofuran-2-carboxamide (6.3 g) and water (50 mL) was stirred for 5-10 minutes at 27° C. Sodium bicarbonate (3.62 g) and sodium iodide (1.6 g) was added to the reaction mass and heated to 85-90° C. for 13 hours. The reaction mass was then allowed to cool to room temperature and water (50 mL) was added. The solid was filtered, washed with water (25 mL) and dried at about 60° C. for 6 hours to afford the title compound.

Yield: 8.52 g (89.5%)

Purity (by HPLC): 92.68%

Water content: 4.72% w/w

Example 11h

A mixture of 3-(4-chlorobutyl)-1H-indole-5-carbonitrile (3 g), 5-(piperazin-1-yl)benzofuran-2-carboxamide (3.8 g) and water (30 mL) was stirred for 5-10 minutes at 27° C. Sodium carbonate (2.74 g) and sodium iodide (0.96 g) was added to the reaction mass and heated to 85-90° C. for about 11 hours. The reaction mass was then allowed to cool to room temperature. Water (15 mL) and methanol (15 mL) was added to the reaction mass. The solid was filtered, washed with water (15 mL) and dried at about 55° C. for 4 hours to afford the title compound.

Yield: 5.3 g (92.98%)

Purity (by HPLC): 94.02%.

Example 11i

A mixture of 3-(4-chlorobutyl)-1H-indole-5-carbonitrile (2 g), 5-(piperazin-1-yl)benzofuran-2-carboxamide (2.53 g) and water (10 mL) was stirred for 5-10 minutes at 27° C. Sodium carbonate (1.82 g) was added to the reaction mass and heated to 80-85° C. for about 18 hours. The reaction mass was then allowed to cool to room temperature and water (20 mL) was added. The solid was filtered and dried at about 60° C. for 6 hours to afford the title compound.

Yield: 3.35 g (88.15%)

Purity (by HPLC): 82.24%.

Example 12: Preparation of 3-(4-chlorobutanoyl)indole-5-carbonitrile

To a solution of 5-cyano indole (100 g) in dichloromethane (4 L) titanium tetrachloride (214 g) was added at 0-5° C. under nitrogen atmosphere. The resulting mixture was stirred for 45 minutes and then 4-chlorobutyryl chloride (168.8 g) was added to the mixture drop wise. The reaction mass was stirred at room temperature for 5 hours and again cooled to 0-5° C. The reaction mass is quenched by ice-cold water (2 L) and stirred for 4 hours. The resulting solid material was filtered, washed with water (300 mL). Water (1 L) was added to the wet material and the pH of the reaction mass was adjusted to 7.0 with aqueous solution of sodium bicarbonate (3% w/v). The reaction mass was stirred for 10-15 minutes at room temperature, filtered, washed with water and dried to provide the desired compound.

Yield: 120 g (69%)

Purity (by HPLC): 91.96%.

Example 13: Preparation of 3-(4-chlorobutyl)indole-5-carbonitrile

To a solution of 3-(4-chlorobutanoyl)indole-5-carbonitrile (100 g) in tetrahydrofuran (3.5 L), sodium borohydride (7.68 g) and boron trifluoride etherate (115.04 g) was added under nitrogen atmosphere. The reaction mass was stirred for 30 minutes at room temperature. Another lot of sodium borohydride (3.84 g) and boron trifluoride etherate (57.52 g) was added to the reaction mass. The reaction mass was again stirred for 30 minutes at room temperature. A third lot of sodium borohydride (3.84 g) and boron trifluoride etherate (57.52 g) was added to the reaction mass and the reaction mass again stirred for another 30 minutes. The reaction was completed after 30 minutes of the addition of fourth lot of sodium borohydride (3.84 g) and boron trifluoride etherate (57.52 g). The reaction mass was slowly poured in ice-water (2 L) and extracted with ethyl acetate (2×2 L). The combined organic layer was washed with sodium bicarbonate solution (2×2 L), water (2 L), brine (1 L), dried over anhydrous sodium sulfate (100 g) and concentrated under reduced pressure at a temperature less than about 50° C. to afford a crude material. The crude material is diluted with dichloromethane (2450 mL) and hexane (4550 mL) and stirred for 30 minutes. Silica gel (15 g) was added to the above solution and then filtered through hyflow. Hyflow bed was washed with 35% dichloromethane in hexane (1 L). The organic layer was concentrated under reduced pressure at a temperature less than about 50° C. and diluted with hexane (1 L). The solution was stirred at room temperature for 10 minutes and the precipitated solid was filtered and dried at room temperature to provide the desired compound.

Yield: 62 g (66%)

Purity (by HPLC): 98.2%.

Example 14: Conversion of Form G to Form B of Vilazodone Hydrochloride

Form G of vilazodone hydrochloride as prepared in example 8h (20 g) was taken in a petri-dish with uniform thickness. The petri-dish was kept in humidification chamber at about 34° C. at RH about 52%. The material was humidified for about 24 hours to provide form B of vilazodone hydrochloride.

Example 15: Purification of Vilazodone Free Base

Example 15a

Vilazodone free base (3 g) was charged in DMF (12 mL) at room temperature. To the above mixture, ethyl acetate (36 mL) and water (12 mL) was added and the reaction mixture was stirred for about 3 hours at room temperature. The solid was filtered and washed with ethyl acetate (6 mL). The solid was dried for about 11 hours at 55° C. to afford pure vilazodone free base.

Yield: 2.6 g (86.6%)

Purity by HPLC: 99.48%

Example 15b

Vilazodone free base (30 g) was charged in DMF (120 mL) at room temperature. To the above mixture, triethylamine (90 mL) was added. Slowly, water (60 mL) was added to the above reaction mixture. The reaction mixture was stirred for 1 hour at room temperature, filtered, washed with water (150 mL) and suck-dried for 10 minutes. The wet solid was charged into DMF (50 mL). To the above reaction mixture, water (90 mL) and isopropyl acetate (60 mL) was added and stirred at room temperature for 1 hour. The solid was filtered, washed with isopropyl acetate (360 mL) and dried in vacuum oven for 2 hours at 60° C. The dried compound was again charged in DMF (90 mL) and isopropyl acetate (125 mL). Carbon powder (9 g) was added to the reaction mixture and stirred for 15 minutes. The solid was filtered, washed with DMF (75 mL) and isopropyl acetate (150 mL). To the mother liquor, isopropyl acetate (100 mL) was added followed by water (49 mL). The reaction mixture was stirred at room temperature for 1 hour, filtered, washed with isopropyl acetate (50 mL) and dried to provide pure vilazodone free base.

Yield: 20.5 g (68%)

Purity by HPLC: 99.20%

Reference Example 1: Preparation of Vilazodone Free Base Form II

To a solution of 5-(1-piperazinyl)benzofuran-2-carboxamide (1.3 g) in methanol (152.9 mL), sodium cyanoborohydride (0.84 g) was added at 20° C. and stirred for 5-10 minutes. A solution of 3-(4-oxobutyl)-1H-indole-5-carbonitrile (1.83 g) in methanol (38 mL) was added over a period of 15 minutes. The reaction mass was stirred at 20° C. for about 18 hours and then cooled to 10° C. for 6 hours. The precipitated solid was filtered, washed with water (10 mL), methanol (10 mL) and dried under vacuum.

Yield: 1.76 g (75.21%).

We claim:

1. Crystalline form G of vilazodone hydrochloride characterized by powder X-ray diffraction (PXRD) pattern having peaks at about 10.71, 16.59, 20.58 and 22.27±0.2 degrees 2θ.

2. Process for preparing crystalline form G of vilazodone hydrochloride of claim 1, which comprises:

a) providing a mixture of vilazodone free base in methanol;

b) combining hydrochloric acid with the mixture of step a); and c) isolating crystalline form G of vilazodone hydrochloride.

3. Pharmaceutically acceptable dosage form comprising crystalline vilazodone hydrochloride of claim 1 and one or more pharmaceutically acceptable excipients.

4. Crystalline form G of vilazodone hydrochloride of claim 1, characterized by powder X-ray diffraction (PXRD) pattern having additional peaks at about 8.61, 21.33, 24.30 and 25.01±0.2 degrees 2θ.

5. Crystalline form G of vilazodone hydrochloride of claim 1, characterized by powder X-ray diffraction (PXRD) pattern having additional peaks at about 15.41 and 19.40±0.2 degrees 2θ.

* * * * *